(12) United States Patent
Maharbiz et al.

(10) Patent No.: US 10,300,310 B2
(45) Date of Patent: May 28, 2019

(54) IMPLANTS USING ULTRASONIC BACKSCATTER FOR SENSING PHYSIOLOGICAL CONDITIONS

(71) Applicant: The Regents of the University of California, Oakland, CA (US)

(72) Inventors: Michel M. Maharbiz, El Cerrito, CA (US); Jose M. Carmena, Berkeley, CA (US); Mekhail Anwar, San Francisco, CA (US); Burak A. Ozilgen, Berkeley, CA (US); Dongjin Seo, Albany, NY (US); Federica Fava, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/141,930

(22) Filed: Sep. 25, 2018

(65) Prior Publication Data

US 2019/0022428 A1    Jan. 24, 2019

Related U.S. Application Data

(63) Continuation of application No. 15/702,301, filed on Sep. 12, 2017, now Pat. No. 10,118,054, which is a
(Continued)

(51) Int. Cl.
*A61N 1/00* (2006.01)
*A61N 7/02* (2006.01)
(Continued)

(52) U.S. Cl.
CPC .............. *A61N 7/02* (2013.01); *A61B 5/0031* (2013.01); *A61B 5/076* (2013.01); *A61B 5/686* (2013.01);
(Continued)

(58) Field of Classification Search
CPC ...... A61N 7/02; A61N 1/3605; A61N 1/3787; A61N 1/37205; A61N 1/0534;
(Continued)

(56) References Cited

U.S. PATENT DOCUMENTS 2,830,274 A    4/1958  Rosen et al.
5,749,909 A    5/1998  Schroeppel et al.
(Continued)

FOREIGN PATENT DOCUMENTS

EP      2162185 B1    7/2015
WO   WO/2007/050657 A1    5/2007
(Continued)

OTHER PUBLICATIONS

U.S. Office Action dated Jan. 10, 2018 issued in U.S. Appl. No. 15/702,301.
(Continued)

*Primary Examiner* — Elmer M Chao
(74) *Attorney, Agent, or Firm* — Tom Hunter; Weaver Austin Villeneuve & Sampson LLP

(57) ABSTRACT

Described herein is an implantable device having a sensor configured to detect an amount of an analyte, a pH, a temperature, strain, or a pressure; and an ultrasonic transducer with a length of about 5 mm or less in the longest dimension, configured to receive current modulated based on the analyte amount, the pH, the temperature, or the pressure detected by the sensor, and emit an ultrasonic backscatter based on the received current. The implantable device can be implanted in a subject, such as an animal or a plant. Also described herein are systems including one or more implantable devices and an interrogator comprising one or more ultrasonic transducers configured to transmit ultrasonic waves to the one or more implantable devices or receive ultrasonic backscatter from the one or more implant-
(Continued)

able devices. Also described are methods of detecting an amount of an analyte, a pH, a temperature, a strain, or a pressure.

30 Claims, 24 Drawing Sheets

Related U.S. Application Data continuation of application No. PCT/US2017/041257, filed on Jul. 7, 2017.

(60) Provisional application No. 62/359,672, filed on Jul. 7, 2016.

(51) Int. Cl.
| | | |
|---|---|---|
| *A61N 1/372* | (2006.01) | |
| *A61N 1/36* | (2006.01) | |
| *A61B 5/07* | (2006.01) | |
| *A61B 5/00* | (2006.01) | |
| *A61N 1/378* | (2006.01) | |
| *G01N 27/327* | (2006.01) | |
| *B06B 1/06* | (2006.01) | |
| *A61B 8/08* | (2006.01) | |
| *A61N 5/10* | (2006.01) | |
| *A61N 1/05* | (2006.01) | |
| *A61B 6/00* | (2006.01) | |
| *A61N 7/00* | (2006.01) | |
| *H02J 7/02* | (2016.01) | |
| *H02J 50/15* | (2016.01) | |
| *A61M 39/02* | (2006.01) | |
| *H02J 50/90* | (2016.01) | |

(52) U.S. Cl.
CPC .......... *A61B 8/0808* (2013.01); *A61N 1/3605* (2013.01); *A61N 1/3787* (2013.01); *A61N 1/37205* (2013.01); *B06B 1/06* (2013.01); *G01N 27/327* (2013.01); *A61B 5/4836* (2013.01); *A61B 6/4258* (2013.01); *A61B 8/085* (2013.01); *A61B 8/0875* (2013.01); *A61B 8/48* (2013.01); *A61B 2505/05* (2013.01); *A61B 2560/0219* (2013.01); *A61B 2562/028* (2013.01); *A61B 2562/12* (2013.01); *A61M 39/0208* (2013.01); *A61M 2205/04* (2013.01); *A61M 2205/825* (2013.01); *A61N 1/0534* (2013.01); *A61N 5/1071* (2013.01); *A61N 2005/1087* (2013.01); *A61N 2007/0021* (2013.01); *H02J 7/025* (2013.01); *H02J 50/15* (2016.02); *H02J 50/90* (2016.02)

(58) Field of Classification Search
CPC .... A61N 2007/0021; A61N 2005/1087; A61N 5/1071; A61B 8/0808; A61B 8/48; A61B 8/0875; A61B 8/085; A61B 5/686; A61B 5/076; A61B 5/0031; A61B 5/4836; A61B 2505/05; A61B 2560/0219; A61B 6/4258; G01N 27/327; B06B 1/06; A61M 39/0208; A61M 2205/04; H02J 50/15; H02J 50/90
See application file for complete search history.

(56) References Cited

U.S. PATENT DOCUMENTS

| | | |
|---|---|---|
| 6,170,488 B1 | 1/2001 | Spillman, Jr. et al. |
| 6,200,265 B1 | 3/2001 | Walsh et al. |
| 6,628,989 B1 | 9/2003 | Penner et al. |
| 6,654,638 B1 | 11/2003 | Sweeney |
| 7,024,248 B2 | 4/2006 | Penner et al. |
| 7,479,112 B2 | 1/2009 | Sweeney et al. |
| 7,616,990 B2 | 11/2009 | Chavan et al. |
| 7,634,318 B2 | 12/2009 | Tran et al. |
| 7,757,565 B2 | 7/2010 | Chakrabartty |
| 7,848,815 B2 | 12/2010 | Brisken et al. |
| 7,890,173 B2 | 2/2011 | Brisken et al. |
| 7,899,542 B2 | 3/2011 | Cowan et al. |
| 7,953,493 B2 | 5/2011 | Fowler et al. |
| 8,078,283 B2 | 12/2011 | Cowan et al. |
| 8,082,041 B1 | 12/2011 | Radziemski |
| 8,480,585 B2 | 7/2013 | Slayton et al. |
| 8,494,637 B2 | 7/2013 | Cowan et al. |
| 8,494,639 B2 | 7/2013 | Cowan et al. |
| 8,494,642 B2 | 7/2013 | Cowan et al. |
| 8,494,643 B2 | 7/2013 | Cowan et al. |
| 8,494,644 B2 | 7/2013 | Cowan et al. |
| 8,634,908 B2 | 1/2014 | Cowan |
| 8,718,773 B2 | 5/2014 | Willis et al. |
| 8,874,233 B2 | 10/2014 | Mclaughlin et al. |
| 8,934,972 B2 | 1/2015 | Penner |
| 9,364,362 B2 | 6/2016 | Berkcan et al. |
| 9,452,286 B2 | 9/2016 | Cowan et al. |
| 9,544,068 B2 | 1/2017 | Arbabian et al. |
| 9,802,055 B2 | 10/2017 | Reinke et al. |
| 2005/0049492 A1 | 3/2005 | Sweeney et al. |
| 2005/0152946 A1 | 7/2005 | Hunter et al. |
| 2007/0293912 A1 | 12/2007 | Cowan et al. |
| 2009/0018403 A1 | 1/2009 | Black et al. |
| 2010/0268078 A1 | 10/2010 | Scarantino et al. |
| 2013/0062527 A1 | 3/2013 | Hyde et al. |
| 2013/0178915 A1 | 7/2013 | Radziemski et al. |
| 2014/0253435 A1 | 9/2014 | Boser et al. |
| 2014/0336474 A1 | 11/2014 | Arbabian et al. |
| 2015/0112233 A1 | 4/2015 | Towe et al. |
| 2016/0000590 A1 | 1/2016 | Boyden et al. |
| 2016/0007893 A1 | 1/2016 | Roberts |
| 2017/0117753 A1 | 4/2017 | Charthad et al. |
| 2017/0125892 A1 | 5/2017 | Arbabian et al. |
| 2017/0197082 A1 | 7/2017 | Pang et al. |
| 2018/0085605 A1 | 3/2018 | Maharbiz et al. |

FOREIGN PATENT DOCUMENTS

| | | |
|---|---|---|
| WO | WO/2007/090159 A1 | 8/2007 |
| WO | WO/2012/057868 A1 | 5/2012 |
| WO | WO/2015/142842 A2 | 9/2015 |
| WO | WO/2018/009905 A2 | 1/2018 |
| WO | WO/2018/009908 A1 | 1/2018 |
| WO | WO/2018/009910 A1 | 1/2018 |
| WO | WO/2018/009911 A1 | 1/2018 |
| WO | WO/2018/009912 A1 | 1/2018 |

OTHER PUBLICATIONS

U.S. Final Office Action dated Jul. 27, 2018 , 2018 issued in U.S. Appl. No. 15/702,301.
U.S. Notice of Allowance dated Aug. 24, 2018 issued in U.S. Appl. No. 15/702,301.
PCT International Search Report and Written Opinion dated Jan. 2, 2018 issued in PCT/US2017/041257.
PCT International Search Report and Written Opinion dated Nov. 15, 2017 issued in PCT/US2017/041260.
PCT International Search Report and Written Opinion dated Nov. 13, 2017 issued in PCT/US2017/041263.
PCT International Search Report and Written Opinion dated Sep. 20, 2017 issued in PCT/US2017/041262.
PCT International Search Report and Written Opinion dated Nov. 2, 2017 issued in PCT/US2017/041264.
Afroz et al., "Implantable Sic Based RF Antenna Biosensor for Continuous Glucose Monitoring", IEEE, 2013, 4 pages.
Ahmadi et al., "A Wireless-Implantable Microsystem for Continuous Blood Glucose Monitoring", IEEE Transactions on Biomedical Circuits and Systems, vol. 3 No. 3, Jun. 2009, pp. 169-180.
Alivisatos et al., "Nanotools for Neuroscience and Brain Activity Mapping", ACS Nano, vol. 7, No. 3, 2013, pp. 1850-1866.

(56) References Cited

OTHER PUBLICATIONS

Bai et al., "Single-Unit neural Recording with Active Microelectrode Arrays", IEEE Transactions on Biomedical Engineering, vol. 48, No. 8, Aug. 2001, pp. 911-920.
Bartlett et al., "Strategies for the Development of Amperometric Enzyme Electrodes", Biosensors, vol. 3, 1987, pp. 359-379.
Bertrand et al., "Beamforming Approaches for Untethered, Ultrasonic Neural Dust Motes for Cortical Recording: A Simulation Study", 36th Annual International Conference of the IEEE Engineering in Medicine and Biology Society, 2014, pp. 2625-2628.
Beuter et al., "Closed-Loop Cortical Neuromodulation in Parkinson's Disease: An Alternative to Deep Brain Stimulation?", Clinical Neurophysiology, vol. 125, 2014, pp. 874-885.
Beyer et al., "An Implantable MOSFET Dosimeter for the Measurement of Radiation Dose in Tissue During Cancer Therapy", IEEE Sensors Journal, vol. 8, No. 1, 2008, pp. 38-51.
Bhadra et al., "High-Frequency Electrical Conduction Block of Mammalian Peripheral Motor Nerve", Muscle Nerve, vol. 32, No. 6, Dec. 2005, pp. 782-790.
Biederman et al., "A 4.78 mm 2 Fully-Integrated Neuromodulation SoC Combining 64 Acquisition Channels with Digital Compression and Simultaneous Dual Stimulation", IEEE Journal of Solid-State Circuits, vol. 50, No. 4, 2015, pp. 1038-1047.
Biederman et al., "A Fully-Integrated, Miniaturized (0.125 mm$^2$) 10.5 µW Wireless Neural Sensor", IEEE Journal of Solid-State Circuits, vol. 48, No. 4, 2013, pp. 960-970.
Birmingham et al., "Bioelectronic Medicines: A Research Roadmap", Nature Reviews Drug Discovery, vol. 13, No. 6, 2014, pp. 399-400.
Boretius et al., "A Transverse Intrafascicular Multichannel Electrode (Time) to Interface with the Peripheral Nerve", Biosensors and Bioelectronics, vol. 26, No. 1, Sep. 2010, pp. 62-69.
Cardin et al., "Targeted Optogenetic Stimulation and Recording of Neurons in Vivo Using Cell-Type-Specific Expression of Channelrhodopsin-2", Nature Protocols, vol. 5, 2010, pp. 247-254.
Carmena et al., "Learning to Control a Brain—Machine Interface for Reaching and Grasping by Primates", PLoS Biology, vol. 1, No. 2, 2003, pp. 193-208.
Carvalho-De-Souza et al., "Photosensitivity of Neurons Enabled by Cell-Targeted Gold Nanoparticles", Neuron, vol. 86, No. 1, Apr. 8, 2015, pp. 207-217.
Celinskis, Dmitrijs et al., "Wireless impedance measurements for monitoring peripheral vascular disease", 36th Annual International Conference of the IEEE Engineering in Medicine and Biology Society, IEEE, 2014, pp. 6937-6940.
Chapin et al., "Real-Time Control of a Robot Arm Using Simultaneously Recorded Neurons in the Motor Cortex", Nature Neuroscience, vol. 2, 1999, pp. 664-670.
Charthad et al., "A mm-Sized Implantable Medical Device (IMD) with Ultrasonic Power Transfer and a Hybrid Bi-Directional Data Link", IEEE Journal of Solid-State Circuits, vol. 50, No. 8, 2015, pp. 1741-1753.
Chestek et al., "Long-Term Stability of Neural Prosthetic Control Signals From Silicon Cortical Arrays in Rhesus Macaque Motor Cortex", Journal of Neural Engineering, vol. 8, 2011, pp. 1-11.
Cogan et al., "Plasma-Enhanced Chemical Vapor Deposited Silicon Carbide as an Implantable Dielectric Coating", Journal of Biomedical Research: Part A, vol. 67A, No. 3, Oct. 20, 2003, pp. 856-867.
Creasey et al., "An Implantable Neuroprosthesis for Restoring Bladder and Bowel Control to Patients with Spinal Cord Injuries: A Multicenter Trial", Archives of Physical Medicine and Rehabilitation, vol. 82, No. 11,, Nov. 2001, pp. 1512-1519.
Dadarlat et al., "A Learning-Based Approach to Artificial Sensory Feedback Leads to Optimal Integration", Nature Neuroscience, vol. 18, No. 1, Jan. 2015, pp. 138-144.
Delivopoulos et al., "Concurrent Recordings of Bladder Afferents from Multiple Nerves Using a Microfabricated PDMS Microchannel Electrode Array", Lab on a Chip, vol. 12, No. 14, Jul. 2012, pp. 2540-2551.
Dellis, Jean-Luc, "Zfit", version 1.2, MathWorks, Updated on 2010, 6 pages.

Denison et al., "A 2 µW, 100 nV/rtHz, Chopper-Stabilized Instrumentation Amplifier for Chronic Measurement of Neural Field Potentials", IEEE Journal of Solid-State Circuits, vol. 42 No. 12, 2007, pp. 2934-2945.
Dingli et al., "Successful Therapy Must Eradicate Cancer Stem Cells", Stem Cells, vol. 24, 2006, pp. 2603-2610.
Du et al., "Multiplexed, High Density Electrophysiology with Nanofabricated Neural Probes", PLOS One, vol. 6, No. 10, Oct. 2011, pp. e26204.1-11.
Epoxy Technology, "EPO-TEK H20E", Rev. XIII, Jul. 2015, 2 pages.
Famm et al., "Drug Discovery: A Jump-Start for Electroceuticals", Nature, vol. 496, Apr. 2013, pp. 159-161.
Fan et al., "A Wireless Multi-Channel Recording System for Freely Behaving Mice and Rats", PLoS One, vol. 6, No. 7, Jul. 2011, pp. e22033.1-9.
Food and Drug Administration, "Information for Manufacturers Seeking Marketing Clearance of Diagnostic Ultrasound Systems and Transducers", Guidance for Industry and FDA Staff, Sep. 9, 2008, 68 pages.
Foster et al., "A Freely-Moving Monkey Treadmill Model", Journal of Neural Engineering, vol. 11, 2014, pp. 1-14.
Frewin et al., "Silicon Carbide Materials for Biomedical Applications", Carbon for Sensing Devices, Oct. 8, 2014, pp. 153-207.
Ganguly et al., "Emergence of a Stable Cortical Map for Neuroprosthetic Control", PLoS Biology, vol. 7, No. 7, Jul. 2009, pp. e1000153.1-13.
Girman et al., "Rat Experimental Transplantation Surgery: A Pactical Guide", Springer, eBook, 2015.
Gold et al., "Using Extracellular Action Potential Recordings to Constrain Compartmental Models", Journal of Computational Neuroscience, vol. 23, 2007, pp. 39-58.
Grahn et al., "A Neurochemical Closed-Loop Controller for Deep Brain-Stimulation: Toward Individualized Smart Neuromodulation Therapies", Frontiers in Neuroscience, vol. 8, Article 169, Jun. 2014, pp. 1-11.
Gruner et al., "Nonlinear Muscle Recruitment During Intramuscular and Nerve Stimulation", Journal of Rehabilitation Research and Development, vol. 26, No. 2, 1989, pp. 1-16.
Halperin et al., "Perez and Brady's Principles and Practice of Radiation Oncology", Lippincott Williams & Wilkins, 6th Edition, 2013.
Harman-Boehm et al., "Noninvasive Glucose Monitoring: A Novel Approach", Journal of Diabetes Science and Technology, vol. 3, No. 2, Mar. 2009, pp. 253-260.
Harrison et al., "A Low-Power Integrated Circuit for a Wireless 100-Electrode Neural Recording System", IEEE Journal of Solid-State Circuits, vol. 42, No. 1, 2007, pp. 123-133.
Harrison, Reid R., "Designing Efficient Inductive Power Links for Implantable Devices", IEEE International Symposium on Circuits and Systems, 2007, pp. 2080-2083.
He et al., "Nanoscale Neuro-Integrative Coatings for Neural Implants", Biomaterials, vol. 26, 2005, pp. 2983-2990.
Hess et al., "PECVD Silicon Carbide as a Thin Film Packaging Material for Microfabricated Neural Electrodes", Materials Research Society Symposium Proceedings, vol. 1009, 2007, pp. 8-13.
Hochberg et al., "Reach and Grasp by People with Tetraplegia Using a Neurally Controlled Robotic Arm", Nature, vol. 485, May 2012, pp. 372-375.
Holland, Richard, "Resonant Properties of Piezoelectric Ceramic Rectangular Parallelepipeds", The Journal of the Acoustical Society of America, vol. 43, No. 5, 1968, pp. 988-997.
Holmes-Siedle et al., "RADFET: A Review of the Use of Metal-Oxide-Silicon Devices as Dosimeters", International Journal of Radiation Applications and Instrumentation, Part C, Radiation Physics and Chemistry, vol. 28, No. 2, 1986, pp. 235-244.
Holmes-Siedle et al., "The Physics of Failure of MIS Devices Under Radiation", IEEE Transactions on Reliability, vol. R-17, No. 1, 1968, pp. 34-44.
Hoskins et al., "Diagnostic Ultrasound: Physics and Equipment", 2003, 276 pages.

(56) References Cited

OTHER PUBLICATIONS

Hynynen et al., "Demonstration of Potential Noninvasive Ultrasound Brain Therapy through an Intact Skull", Ultrasound in Medicine and Biology, vol. 24, No. 2, Feb. 1998, pp. 275-283.
IEEE, "IEEE Standard for Safety Levels with Respect to Human Emposure to Radio Frequency Electromagnetic Fileds, 3khz to 300 Ghz", IEEE Standards Coordinating Committee 28 on Non-Ionizing Radiation Hazards, 1991, 72 pages.
IEEE, "IEEE Standard for Safety Levels with Respect to Human Exposure to Radio Frequency Electromagnetic Fields, 3 kHz to 300 GHz", IEEE International Committee on Electromagnetic Safety (SCC39), Apr. 2006, 250 pages.
Ishida et al., "Insole Pedometer With Piezoelectric Energy Harvester and 2 V Organic Circuits", IEEE Journal of Solid-State Circuits, vol. 48, No. 1, 2013, pp. 255-264.
Jow et al., "Design and Optimization of Printed Spiral Coils for Efficient Transcutaneous Inductive Power Transmission", IEEE Transactions on Biomedical Circuits and Systems, vol. 1, No. 3, 2007, pp. 193-202.
Kay, Joshua, "Rodent Wearable Ultrasound Interrogation System for Wireless Neural Recording", Berkeley EECS, Technical Report No. UCS/EECS-2017-27, May 4, 2017, 50 pages.
Kim et al., "Injectable, Cellular-Scale Optoelectronics with Applications for Wireless Optogenetics", Science, vol. 340, Apr. 12, 2013, pp. 211-216.
Kiourti et al., "A Wireless Fully Passive Neural Recording Device for Unobtrusive Neuropotential Monitoring", IEEE Transactions on Biomedical Engineering, vol. 63, No. 1, 2016, pp. 131-137.
Klueh et al., "Metabolic Biofouling of Glucose Sensors in Vivo: Role of Tissue Microhemorrhages", Journal of Diabetes Science and Technology, vol. 5, No. 3, May 2011, pp. 583-595.
Koralek et al., "Corticostriatal Plasticity is Necessary for Learning Intentional Neuroprosthetic Skills", Nature, vol. 483, Mar. 15, 2012, pp. 331-335.
Kozai et al., "Ultrasmall Implantable Composite Microelectrodes with Bioactive Surfaces for Chronic Neural Interfaces", Nature Materials, vol. 11, 2012, pp. 1065-1073.
Krimholtz et al., "New Equivalent Circuits for Elementary Piezoelectric Transducers", Electronics Letters, vol. 6, No. 13, 1970, pp. 398-399.
Krook-Magnuson, "Neuroelectronics and Biooptics: CLoed Loop Technologies in Neurological Disorders", JAMA Neurology, vol. 72, No. 7, Jul. 2015, pp. 823-829.
Kuo et al., "Associations Between Periodontal Diseases and Systematic Disease: A Review of the Inter-relationships and Interactions with Diabetes, Respiratory Diseases, Cardiovascular Diseases and Osteoporosis", Public Health, vol. 122, No. 4, Apr. 2008, pp. 417-433.
Lapatki et al., "A Thin, Flexible Multielectrode Grid for High-Density Surface EMG", Journal of Applied Physiology, vol. 96, No. 1, Jan. 2004, pp. 327-336.
Larson et al., "Miniature Ultrasonically Powered Wireless Nerve Cuff Stimulator", Proceedings of the 5th International IEEE/EMBS Conference on Neural Engineering, 2011, pp. 265-268.
Ledochowitsch et al., "Fabrication and Testing of a Large Area, High Density, Parylene MEMS μECOG Array", IEEE 24th International Conference on Micro Electro Mechanical Systems, 2011, pp. 1031-1034.
Lee et al., "A Wideband Dual-Antenna Receiver for Wireless Recording from Animals Behaving in Large Arenas", IEEE Transactions on Biomedical Engineering, vol. 60, No. 7, 2013, pp. 1993-2004.
Lee et al., "An Inductively Powered Scalable 32-Channel Wireless Neural Recording System-on-a-Chip for Neuroscience Applications", IEEE Transactions on Biomedical Circuits and Systems, vol. 4, No. 6, 2010, pp. 360-371.
Lefurge et al., "Chronically Implanted Intrafascicular Recording Electrodes", Annals of Biomedical Engineering, vol. 19, No. 2, 1991, pp. 197-207.

Leighton, Timothy G., "What is Ultrasound", Progress in Biophysics and Molecular Biology, vol. 93, 2007, pp. 3-83.
Lin et al., "Low Phase Noise Array-Composite Micromechanical Wine-Glass Disk Oscillator", IEEE InternationalElectron Devices Meeting, IEDM Technical Digest, 2005, pp. 1-4.
Lind et al., "The Density Difference Between Tissue and Neural Probes is a Key Factor for Glial Scarring", Scientific Reports, vol. 3, 2013, pp. 2942.1-7.
Liu et al., "Monte Carlo Simulation Studies of EEG and MEG Localization Accuracy", Human Brain Mapping, vol. 16, 2002, pp. 47-62.
Lu et al., "Current Challenges to the Clinical Translation of Brain Machine Interface Technology", International Review of Neurobiology, vol. 107, 2012, pp. 137-160.
Maleki et al., "An Ultrasonically Powered Implantable Micro-Oxygen Generator (IMOG)", IEEE Transactions on Biomedical Engineering, 2011, pp. 3104-3111.
Malmivuo et al., "Effect of Skull Resistivity on the Spatial Resolutions of EEG and MEG", IEEE Transactions on Biomedical Engineering, vol. 51 No. 7, Jul. 7, 2004, pp. 1276-1280.
Marblestone et al., "Physical Principles for Scalable Neural Recording", Frontiers in Computational Neuroscience, vol. 7, Article 137, Oct. 2013, pp. 1-34.
Martinez-Valdes et al., "High-Density Surface Electromyography Provides Reliable Estimates of Motor Unit Behaviour", Clinical Neurophysiology, vol. 127, No. 6, 2016, pp. 2534-2541.
Maynard et al., "The Utah Intracortical Electrode Array: a Recording Structure for Potential Brain-Computer Interfaces", Electroencephalography and Clinical Neurophysiology, vol. 102, 1997, pp. 228-239.
Mazzilli et al., "In-Vitro Platform to study Ultrasound as Source for Wireless Energy Transfer and Communication for Implanted Medical Devices", 32nd Annual International Conference of the IEEE EMBS, 2010, pp. 3751-3754.
Meacham et al., "A Lithographically-Patterned, Elastic Multi-Electrode Array for Surface Stimulation of the Spinal Cord", Biomedical Microdevices, vol. 10, 2008, pp. 259-269.
Meng et al., "An Electroacoustic Recording Device for Wireless Sensing of Neural Signals", 35th Annual International Conference of the IEEE Engineering in Medicine and Biology Society (EMBC), 2013, pp. 3086-3088.
Mezzarane et al., "Experimental and Simulated EMG Responses in the Study of the Human Spinal Cord", Chapter 4, Electrodiagnosis in New Frontiers of Clinical Research, 2013, pp. 57-87.
Miranda et al., "HermesD: A High-Rate Long-Range Wireless Transmission System for Simultaneous Multichannel Neural Recording Applications", IEEE Transactions on Biomedical Circuits and Systems, vol. 4, No. 3, Jun. 2010, pp. 181-191.
Mohan et al., "Simple Accurate Expressions for Planar Spiral Inductances", IEEE Journal of Solid-State Circuits, vol. 34, No. 10, Oct. 1999, pp. 1419-1424.
Mohseni et al., "Guest Editorial Closing the Loop Via Advanced Neurotechnologies", IEEE Transactions on Neural Systems and Rehabilitation Engineering, vol. 20, No. 4, Jul. 2012, pp. 407-409.
Muller et al., "A 0.013 mm$^2$, 5 μW, DC-Coupled Neural Signal Acquisition IC With 0.5 V Supply", IEEE Journal of Solid-State Circuits, vol. 47, No. 1, Jan. 2012, pp. 232-243.
Muller et al., "A Minimally IEEE Journal of Solid-State Circuits, Invasive 64-Channel Wireless μECoG Implant", IEEE Journal of Solid-State Circuits, vol. 50, No. 1,, Jan. 2015, pp. 1-16.
Nicolelis et al., "Chronic, Multisite, Multielectrode Recordings in Macaque Monkeys", PNAS, vol. 100, No. 19, Sep. 16, 2003, pp. 11041-11046.
Nicolelis, Miguel A. L., "Brain-Machine Interfaces to Restore Motor Function and Probe Neural Circuits", Nature Reviews Neuroscience, vol. 4, May 2003, pp. 417-422.
O'Doherty et al., "Active Tactile Exploration Using a Brain-Machine-Brain Interface", Nature, vol. 479, Nov. 10, 2011, pp. 228-231.
Ozeri et al., "Ultrasonic Transcutaneous Energy Transfer for Powering Implanted Devices", Ultrasonics, vol. 50, 2010, pp. 556-566.
Pavlov et al., "The Vagus Nerve and the Inflammatory Reflex-Linking Immunity and Metabolism", Nat Rev Endocrinol., vol. 8, No. 12, Dec. 2012, pp. 743-754.

(56) References Cited

OTHER PUBLICATIONS

Peisino, Michela, "Deeply implanted medical device based on a novel ultrasonic telemetry technology", Ecole Polytechnique Federale De Lausanne, 2013, pp. 147. Retrieved from the Internet: URL:https://infoscience.epfl.ch/record/186391/files/EPFL_TH5730.pdf [retrieved on Mar. 23, 2015].

Polikov et al., "Response of Brain Tissue to Chronically Implanted Neural Electrodes", Journal of Neuroscience Methods, vol. 148, 2005, pp. 1-18.

Polikov, et al., "In Vitro Model of Glial Scarring Around Neuroelectrodes Chronically Implanted in the CNS", Biomaterials, vol. 27, 2006, pp. 5368-5376.

Potter et al., "Stab Injury and Device Implantation within the Brain Results in Inversely Multiphasic Neuroinflammatory and Neurodegenerative Responses", Journal of Neural Engineering, vol. 9, No. 4, 2012, pp. 046020.

Rabaey et al., "Powering and Communicating with mm-Size Implants", IEEE, Design, Automation & Test in Europe, 2011, pp. 1-6.

Ramachnadran et al., "A Study of Parylene C Polymer Deposition Inside Microscale Gaps", IEEE Transactions on Advanced Packaging, vol. 30, 2007, pp. 712-724.

Randals, J.E.B, "Kinetics of Rapid Electrode Reactions", Discussions of the Faraday Society, vol. 1, 1947, pp. 11-19.

Rebrin et al., "Subcutaneous Glucose Monitoring by Means of Electrochemical Sensors: Fiction or Reality?", Journal of Biomedical Engineering, vol. 14, Jan. 1992, pp. 33-40.

Richards et al., "Efficiency of Energy Conversion for Devices Containing A Piezoelectric Component", Journal of Micromechanics and Microengineering, vol. 14, 2004, pp. 717-721.

Roa-Prada et al., "An Ultrasonic Through-Wall Communication (UTWC) System Model", Journal of Vibration and Acoustics, vol. 135, No. 1, 2013, pp. 1-12.

Robinson et al., "Nanowire Electrodes for High-Density Stimulation and Measurement of Neural Circuits", Frontiers in Neural Circuits, vol. 7, Article 38, Mar. 2013, pp. 1-5.

Rogers et al., "Materials and Mechanics for Stretchable Electronics", Science, vol. 327, Mar. 26, 2010, pp. 1603-1607.

Rosas-Ballina et al., "Acetylcholine-Synthesizing T Cells Relay Neural Signals in a Vagus Nerve Circuit", Science, vol. 334, No. 6052, Oct. 7, 2011, pp. 98-101.

Saddow et al., "Advances in Silicon Carbide Processing and Applications", Artech House, Inc., 2004, 223 pages.

Sadek et al., "Wiring Nanoscale Biosensors with Piezoelectric Nanomechanical Resonators", Nano Letters, vol. 10, 2010, pp. 1769-1773.

Schwarz et al., "Chronic, Wireless Recordings of Large Scale Brain Activity in Freely Moving Rhesus Monkeys", Nat Methods, vol. 11, No. 6, 2014, pp. 670-676.

Schwerdt et al., "A Fully Passive Wireless Microsystem for Recording of Neuropotentials Using RF Backscattering Methods", Journal of Microelectromechanical Systems, vol. 20, No. 5, 2011, pp. 1119-1130.

Seo et al., "Model Validation of Untethered, Ultrasonic Neural Dust Motes for Cortical Recording", Journal of Neuroscience Methods, vol. 244, 2015, pp. 114-122.

Seo et al., "Neural Dust: An Ultrasonic, Low Power Solution for Chronic Brain-Machine Interfaces", Neurons and Cognition, Jul. 2013, pp. 1-11.

Seo et al., "Ultrasonic Beamforming System for Interrogating Multiple Implantable Sensors", Conf Proc IEEE Eng Med Biol Soc., 2015, pp. 2673-2676.

Seo et al., "Wireless Recording in the Peripheral Nervous System with Ultrasonic Neural Dust", Neuron, vol. 91, Aug. 3, 2016, pp. 529-539.

Seo, Dongjin, "Design of Ultrasonic Power Link for Neural Dust", Technical Report No. UCB/EECS-2016-21, Electrical Engineering and Computer Sciences University of California at Berkeley, May 1, 2016, 71 pages.

Serruya et al., "Instant Neural Control of a Movement Signal", Nature, vol. 416, Mar. 14, 2002, pp. 141-142.

Seymour et al., "Neural Probe Design for Reduced Tissue Encapsulation in CNS", Biomaterials, vol. 28, 2007, pp. 3594-3607.

Shapiro et al., "Infrared Light Excites Cells by Changing their Electrical Capacitance", Nature Communications, vol. 3, Article 736, 2012, 10 pages.

Shen, Konlin, "Assembly of a Wireless Ultrasonic Backscatter System", Spring 2016, 61 pages.

Shenoy et al., "Neural Prosthetic Control Signals from Plan Activity", NeuroReport, vol. 14, No. 4, Mar. 24, 2003, pp. 591-596.

Sodagar et al., "Capacitive Coupling for Power and Data Telemetry to Implantable Biomedical Microsystems", Proceedings of the 4th International IEEE EMBS Conference on Neural Engineering, Apr. 29-May 2, 2009, pp. 411-414.

Srinivasan, Ramesh, "Methods to Improve the Spatial Resolution of EEG", International Journal of Bioelectromagnetism, vol. 1, No. 1, 1999, pp. 102-111.

Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, vol. 20, No. 4, Jul. 2012, pp. 410-421.

Stark, Nancy, "Literature Review: Biological Safety of Parylene C", Medical Device and Diagnostic Industry, Mar. 1996, 7 pages.

Stevenson et al., "How Advances in Neural Recording Affect Data Analysis", Nature Neuroscience, vol. 14, No. 2, Feb. 2011, pp. 139-142.

Steyaert et al., "A Micropower Low-Noise Monolithic Instrumentation Amplifier for Medical Purposes", IEEE Journal of Solid-State Circuits, vol. Section-22, No. 6, Dec. 1987, pp. 1163-1168.

Strollo et al., "Upper-Airway Stimulation for Obstructive Sleep Apnea", New England Journal of Medicine, vol. 370, Jan. 9, 2014, pp. 139-149.

Stypulkowski et al., "Brain Stimulation for Epilepsy-Local and Remote Modulation of Network Excitability", Brain Stimulation, vol. 7, No. 3, 2014, pp. 350-358.

Sudhakar, Akulapalli, "History of Cancer, Ancient and Modern Treatment Methods", Journal of Cancer Science and Therapy, vol. 1, No. 2, 2009, 4 pages.

Suner et al., "Reliability of Signals from a Chronically Implanted, Silicon-Based Electrode Array in Non-Human Primate Primary Motor Cortex", IEEE Transactions on Neural Systems and Rehabilitation Engineering, vol. 13, No. 4, Dec. 2005, pp. 524-541.

Swett et al., "Motoneurons of the Rat Sciatic Nerve", Experimental Neurology, vol. 93, 1986, pp. 227-252.

Swisher et al., "Impedance Sensing Device Enables Early Detection of Pressure Ulcers in Vivo", Nature Communications, vol. 6, 2015, 17 pages.

Szuts et al., "A wireless Multi-Channel Neural Amplifier for Freely Moving Animals", Nature Neuroscience, vol. 14, 2011, pp. 263-269.

Tang et al., "Integrated Ultrasonic System for Measuring Body-Fat Composition", IEEE International Solid-State Circuits Conference, 2015, 3 pages.

Tang et al., "Miniaturizing Ultrasonic System for Portable Health Care and Fitness", IEEE Transactions on Biomedical Circuits and Systems, vol. 9, No. 6, Dec. 2015, pp. 767-776.

Trolier-McKinstry et al., "Thin Film Piezoelectrics for MEMS", Journal of Electroceramics, vol. 12, 2004, pp. 7-17.

Turner et al., "Cerebral Astrocyte Response to Micromachined Silicon Implants", Experimental Neurology, vol. 156, 1999, pp. 33-49.

Updike et al., "Enzymatic Glucose Sensors: Improved Long Term Performance in Vitro and in Vivo", ASAIO Journal, vol. 40, 1994, pp. 157-163.

Venkatraman et al., "Active Sensing of Target Location Encoded by Cortical Microstimulation", IEEE Transactions on Neural Systems and Rehabilitation Engineering, vol. 19, No. 3, Jun. 2011, pp. 317-324.

Watanabe et al., "Reconstruction of Movement-Related Intracortical Activity From Micro-Electrcorticogram Array Signals in Monkey Motor Cortex", Journal of Neural Engineering, vol. 9, 2012, 58 pages.

(56) References Cited

OTHER PUBLICATIONS

Weissleder et al., "Molecular imaging", Radiology, vol. 219, 2001, 316-333.
Wells et al., "Optical Stimulation of Neural Tissue in Vivo", Optics Letters, vol. 30, No. 5, 2005, pp. 504-506.
Wilkins et al., "Glucose Monitoring: State of the Art and Future Possibilities", Medical Engineering and Physics, vol. 18, No. 4, 1996, pp. 273-288.
Williamson et al., "Localized Electrical Nerve Blocking", IEEE Transactions on Biomedical Engineering, vol. 52, No. 3, Mar. 2005, pp. 362-370.
Wilson et al., "Better Speech Recognition with Cochlear Implants", Letters to Nature, vol. 352, Jul. 18, 1991, pp. 236-238.
Wolgemuth, Lonny, "Assessing the Performance and Suitability of Parylene Coating", Medical Device and Diagnostic Industry, Aug. 2000, 6 pages.
Wong et al., "Advantages of Capacitive Micromachined Ultrasonics Transducers (CMUTs) for High Intensity Focused Ultrasound (HIFU)", IEEE Ultrasonics Symposium, 2007, pp. 1313-1316.
Xu et al., "Stretchable Batteries with Self-Similar Serpentine Interconnects and Integrated Wireless Recharging Systems", Nature Communications, 2013, 36 pages.
Yakolev et al., "Implantable Biomedical Devices: Wireless Powering and Communication", IEEE Communications Magazine, Apr. 2012, pp. 152-159.
Yin et al., "Wireless Neurosensor for Full-Spectrum Electrophysiology Recordings During Free Behavior", NeuroResource, Neuron, vol. 84, Dec. 17, 2014, p. 1170-1182.
Zenner et al., "Human Studies of a Piezoelectric Transducer and A Microphone for a Totally Implantable Electronic Hearing Device", The American Journal of Otology, vol. 21, No. 2, Mar. 2000, pp. 196-204.
Zorman, CH., "Silicon Carbide as a material for Biomedical Microsystems", EDA Publishing Association, 2009, 8 pages.

Interrogator Transducer

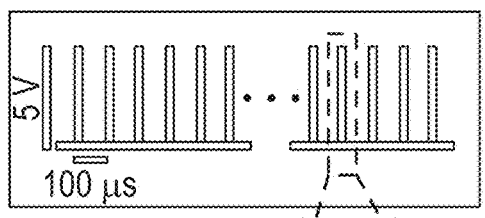
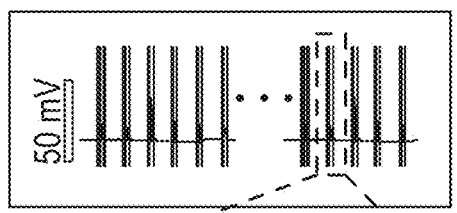
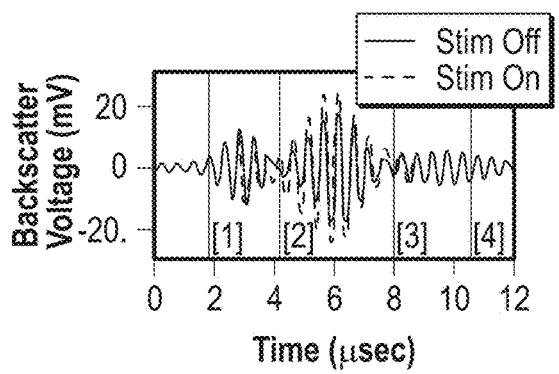
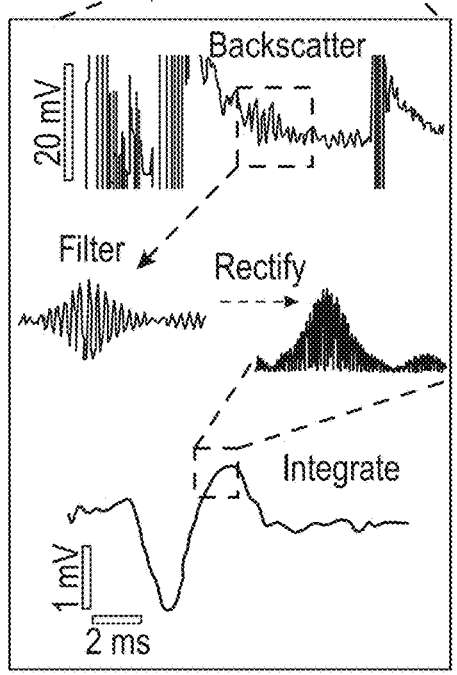
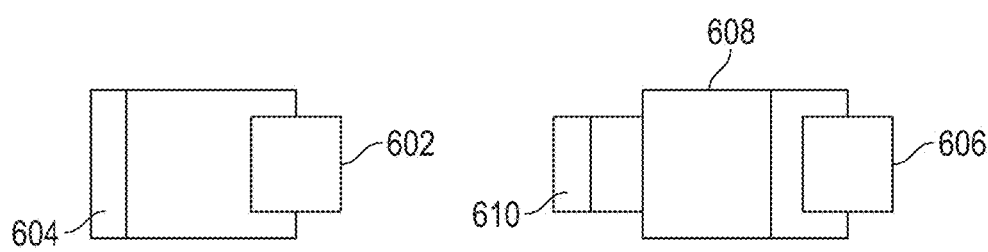
FIG. 5A, FIG. 5B, FIG. 5C, FIG. 5D, FIG. 5E
FIG. 6A, FIG. 6B

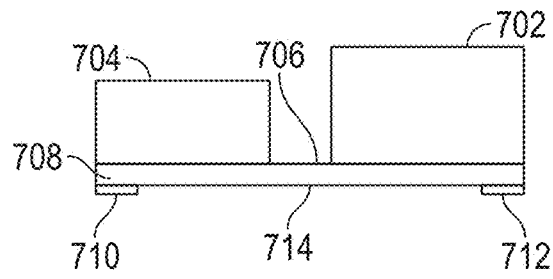
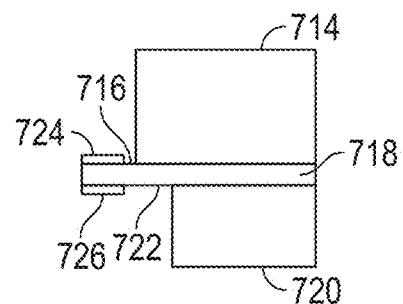
FIG. 7A        FIG. 7B
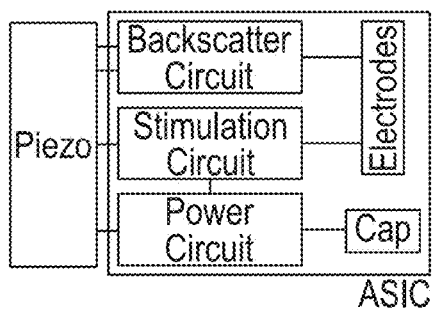
FIG. 8A
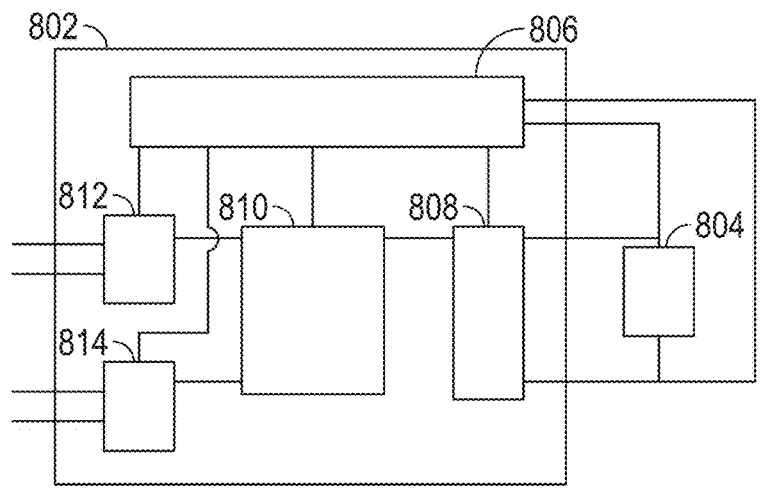
FIG. 8B 1. Start w/SCS 2. Spin PI Layer 3. PECVD a-SIC 4. RIE Openings for Electrodes 5. Evaporate Ruthenium and Plate Gold onto Electrode Sites 6. Die/Piezo Attach and Wirebond 7. PECVD a-SIC Encapsulation 8. RIE Emboss Topside, Remove Film from Backside 9. Dissolve Wafer (TMAH)

//\ # IMPLANTS USING ULTRASONIC BACKSCATTER FOR SENSING PHYSIOLOGICAL CONDITIONS

CROSS-REFERENCE TO RELATED APPLICATION

This application is a continuation of U.S. application Ser. No. 15/702,301, filed on Sep. 12, 2017, which is a continuation of International Application No. PCT/US2017/041257, filed internationally on Jul. 7, 2017, which claims priority benefit of U.S. Provisional Application No. 62/359,672, filed on Jul. 7, 2016, all of which are incorporated herein by reference in their entirety for all purposes.

STATEMENT AS TO FEDERALLY SPONSORED RESEARCH

This invention was made with government support under Grant Nos. HR0011-15-2-0006 awarded by the Defense Advanced Research Projects Agency (DARPA). The government has certain rights in the invention.

TECHNICAL FIELD

The present invention relates to implantable devices for sensing and reporting physiological conditions in a subject using ultrasonic backscatter.

BACKGROUND

A previously known "neural dust" system includes small, implantable devices (referred to as "neural dust" or "motes"), an implantable ultrasound transceiver that communicates with each of the motes using ultrasound transmissions and backscatter transmissions reflected from the motes, and an external transceiver that communicates wirelessly with the implantable ultrasound transceiver. See Seo et al., Neural dust: an ultrasonic, low power solution for chronic brain-machine interfaces, arXiv: 1307.2196v1 (Jul. 8, 2013); Seo et al., Model validation of untethered, ultrasonic neural dust motes for cortical recording, Journal of Neuroscience Methods, vol. 224, pp. 114-122, available online Aug. 7, 2014; and Bertrand et al., Beamforming approaches for untethered, ultrasonic neural dust motes for cortical recording: a simulation study, IEEE EMBC (August 2014). The neural dust system described in these papers is used for cortical recording (i.e., the recording of brain electrical signals). In that application as shown in the papers, the motes are implanted in the brain tissue (cortex), the ultrasound transceiver (i.e., an "interrogator") is implanted below the dura, on the cortex, and the external transceiver is placed against the head of the patient proximate to where the sub-dural ultrasound transceiver is implanted. This neural dust system is illustrated in FIG. 1.

Careful monitoring of certain physiological conditions in a subject can allow for a better understanding of health and disease prognosis. For example, blood sugar monitoring is used to monitor the health of a diabetic patient, and blood oxygenation levels are useful in monitoring compartment syndrome, cancer, or organ transplants. However, continuous deep tissue monitoring of certain physiological conditions is impractical using known technology. What is needed is an implantable device for sensing physiological conditions.

SUMMARY OF THE INVENTION

Described herein are implantable devices for sensing physiological conditions (such as pH, analyte levels, pressure, strain, or temperature) in a subject, and reporting the sensed physiological conditions using ultrasonic backscatter. Further described are systems including one or more implantable devices and an interrogator. Also described are methods for sensing physiological conditions and reporting the sensed physiological conditions using ultrasonic backscatter.

In one aspect, there is provided an implantable device, comprising a sensor configured to detect an amount of an analyte, pH, a temperature, strain, or a pressure; and an ultrasonic transducer with a length of about 5 mm or less in the longest dimension, configured to receive current modulated based on the analyte amount, the pH, the temperature, the strain, or the pressure detected by the sensor, and emit an ultrasonic backscatter based on the received current.

In some embodiments of the implantable device, the ultrasonic transducer is configured to receive ultrasonic waves that power the implantable device. In some embodiments, the ultrasonic transducer is configured to receive ultrasonic waves from an interrogator comprising one or more ultrasonic transducers. In some embodiments, the ultrasonic transducer is a bulk piezoelectric transducer, a piezoelectric micro-machined ultrasonic transducer (PMUT) or a capacitive micro-machined ultrasonic transducer (CMUT).

In some embodiments of the implantable device, the implantable device is about 5 mm or less in length in the longest dimension. In some embodiments, the volume of the implantable device is about 5 mm$^3$ or less.

In some embodiments, the implantable device is implanted in a subject. In some embodiments, the subject is a human. In some embodiments, the subject is an animal or a plant.

In some embodiments of the implantable device, the sensor detects the amount of the analyte or pH. In some embodiments, the sensor detects pH or oxygen.

In some embodiments of the implantable device, the sensor is an optical sensor. In some embodiments, the optical sensor comprises a light source and an optical detector. In some embodiments, the optical sensor detects blood pressure or a pulse. In some embodiments, the optical sensor comprises a matrix comprising a fluorophore, and wherein fluorescence intensity or fluorescence lifetime of the fluorophore depends on the amount of the analyte. In some embodiments, the optical sensor is configured to perform near-infrared spectroscopy. In some embodiments, the sensor detects glucose.

In some embodiments, the sensor is a potentiometric chemical sensor or an amperometric chemical sensor. In some embodiments, the sensor detects oxygen, pH, or glucose.

In some embodiments of the implantable device, the sensor is a temperature sensor. In some embodiments, the temperature sensor is a thermistor, a thermocouple, or a proportional to absolute temperature (PTAT) circuit. In some embodiments of the implantable device, the implantable device comprises a bulk piezoelectric ultrasonic transducer and a thermistor.

In some embodiments of the implantable device, the sensor is a pressure sensor. In some embodiments, the pressure sensor is microelectromechanical system (MEMS) sensor. In some embodiments, the implantable device is configured to measure blood pressure or a pulse.

In some embodiments of the implantable device, the sensor is a strain sensor.

In some embodiments of the implantable device, the implantable device further comprises an integrated circuit.

In some embodiments, the integrated circuit comprises one or more of a power circuit, a driver configured to provide current to the sensor, a front end configured to receive a signal from the sensor, or a digital circuit. In some embodiments, the integrated circuit comprises the digital circuit, and wherein the digital circuit is configured to operate a modulation circuit. In some embodiments, the digital circuit is configured to transmit a digitized signal to the modulation circuit, wherein the digitized signal is based on the detected amount of the analyte, the temperature, strain, or the pressure.

In some embodiments of the implantable device, the implanted device is at least partially encapsulated by a biocompatible material.

In some embodiments of the implantable device, the implantable device further comprises a non-responsive reflector.

In some embodiments of the implantable device, the implantable device comprises two or more sensors.

Further provided herein is a system comprising one or more implantable devices and an interrogator comprising one or more ultrasonic transducers configured to transmit ultrasonic waves to the one or more implantable devices or receive ultrasonic backscatter from the one or more implantable devices. In some embodiments, the interrogator comprises one or more ultrasonic transducer arrays, wherein each transducer array comprises two or more ultrasonic transducers. In some embodiments, the system comprises a plurality of implantable devices. In some embodiments, the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices. In some embodiments, the interrogator is configured to simultaneously receive ultrasonic backscatter from at least two implantable devices. In some embodiments, the interrogator is configured to transit ultrasonic waves to the plurality of implantable devices or receive ultrasonic backscatter from the plurality of implantable devices using time division multiplexing, spatial multiplexing, or frequency multiplexing. In some embodiments, the interrogator is configured to be wearable by a subject.

In one aspect, there is provided a method of detecting an amount of an analyte, a pH, a temperature, strain, or a pressure, comprising receiving ultrasonic waves that power one or more implantable devices comprising an ultrasonic transducer with a length of about 5 mm or less in the longest dimension; converting energy from the ultrasonic waves into an electrical current; transmitting the electrical current to a sensor configured to measure the amount of the analyte, the pH, the temperature, strain, or the pressure; modulating the electrical current based on the measured amount of the analyte, pH, temperature, strain, or pressure; transducing the modulated electrical current into an ultrasonic backscatter that encodes the measured amount of the analyte, pH, temperature, strain, or pressure; and emitting the ultrasonic backscatter to an interrogator comprising one or more transducer configured to receive the ultrasonic backscatter.

In one aspect, there is provided a method of detecting an amount of an analyte, a pH, a temperature, strain, or a pressure, comprising receiving ultrasonic waves that power one or more implantable devices comprising an ultrasonic transducer with a length of about 5 mm or less in the longest dimension; converting energy from the ultrasonic waves into an electrical current; measuring the amount of the analyte, the pH, the temperature, the strain, or the pressure using a sensor; modulating the electrical current based on the measured amount of the analyte, pH, temperature, the strain, or pressure; transducing the modulated electrical current into an ultrasonic backscatter that encodes the measured amount of the analyte, pH, temperature, strain, or pressure; and emitting the ultrasonic backscatter to an interrogator comprising one or more transducer configured to receive the ultrasonic backscatter.

In some embodiments of the above-described methods, the method further comprises receiving the ultrasonic backscatter using the interrogator. In some embodiments, the method further comprises transmitting the ultrasonic waves using the interrogator configured to transmit the ultrasonic waves. In some embodiments, the ultrasonic waves are transmitted in two or more pulses.

In some embodiments of the above-described methods, the method further comprises analyzing the ultrasonic backscatter to determine the measured amount of the analyte, pH, temperature, strain, or pressure. In some embodiments of the above-described methods, the one or more implantable devices are implanted on, within, or proximal to a blood vessel, an implanted organ, a tumor, or a site of infection.

In some embodiments of the above-described methods, the method further comprises emitting light and detecting fluorescence intensity or fluorescence lifetime, wherein the fluorescence intensity or fluorescence lifetime depends on the amount of the analyte or the pH. In some embodiments, the method comprises determining a phase shift between oscillating emitted light and detected fluorescence is determined, wherein the phase shift depends on the amount of the analyte or the pH. In some embodiments, the method comprises determining a fluorescent lifetime for the detected fluorescence resulting from pulsed or oscillating emitted light.

In some embodiments of the above-described methods, the method further comprises determining a location of the one or more implantable devices relative to the interrogator.

In some embodiments of the above-described methods, the method further comprises detecting movement of the one or more implantable devices.

In some embodiments of the above-described methods, the method further comprises implanting the implantable device in a subject. In some embodiments, the subject is an animal or a plant. In some embodiments, the subject is a human.

In some embodiments of the above-described methods, the ultrasonic backscatter encodes a digitized signal.

BRIEF DESCRIPTION OF THE FIGURES

FIG. 5A shows a series of cycles of ultrasonic wave pulses emitted by an interrogator. Upon receiving a trigger from the interrogator (e.g., an FPGA), the transceiver board of the interrogator generates a series of transmit pulses. At the end of the transmit cycle, the switch on the ASIC disconnects the transmit module and connects the receive module. The cycles have a frequency of every 100 microseconds. FIG. 5B shows a zoomed-in view of the transmit pulse sequence (i.e., one cycle) shown in FIG. 5A, with the cycle having six pulses of ultrasonic waves at 1.85 MHz, the pulses recurring every 540 nanoseconds. FIG. 5C shows ultrasonic backscatter emitted by an implantable device. The ultrasonic backscatter reaches the transducer of the interrogator approximately $2t_{Rayleigh}$. FIG. 5D shows a zoomed-in view of the ultrasonic backscatter, which can be analyzed. Analysis of the ultrasonic backscatter can include filtering, rectifying and integrating the ultrasonic backscatter waves. FIG. 5E shows a zoomed in view of the filtered ultrasonic backscatter waves. The backscatter wave includes responsive regions, which are responsive to changes in impedance to the miniaturized ultrasonic transducer, and non-responsive regions that are not responsive to changes in impedance to the miniaturized ultrasonic transducer.

FIG. 6A illustrates a schematic of an implantable device with a miniaturized ultrasonic transducer and a sensor. FIG. 6B illustrates a schematic of an implantable device with a miniaturized ultrasonic transducer, an integrated circuit, and a sensor.

FIG. 7A illustrates a schematic of an exemplary implantable device including a miniaturized ultrasonic transducer and an ASIC on a printed circuit board (PCB). FIG. 7B illustrates a schematic of another exemplary implantable device including a miniaturized ultrasonic transducer and an ASIC on a printed circuit board (PCB).

FIG. 8A illustrates one embodiment of an ASIC attached to a miniaturized ultrasonic transducer for an implantable device. FIG. 8B illustrates another embodiment of an integrated circuit attached to a miniaturized ultrasonic transducer for an implantable device.

DETAILED DESCRIPTION OF THE INVENTION

Figure 1:
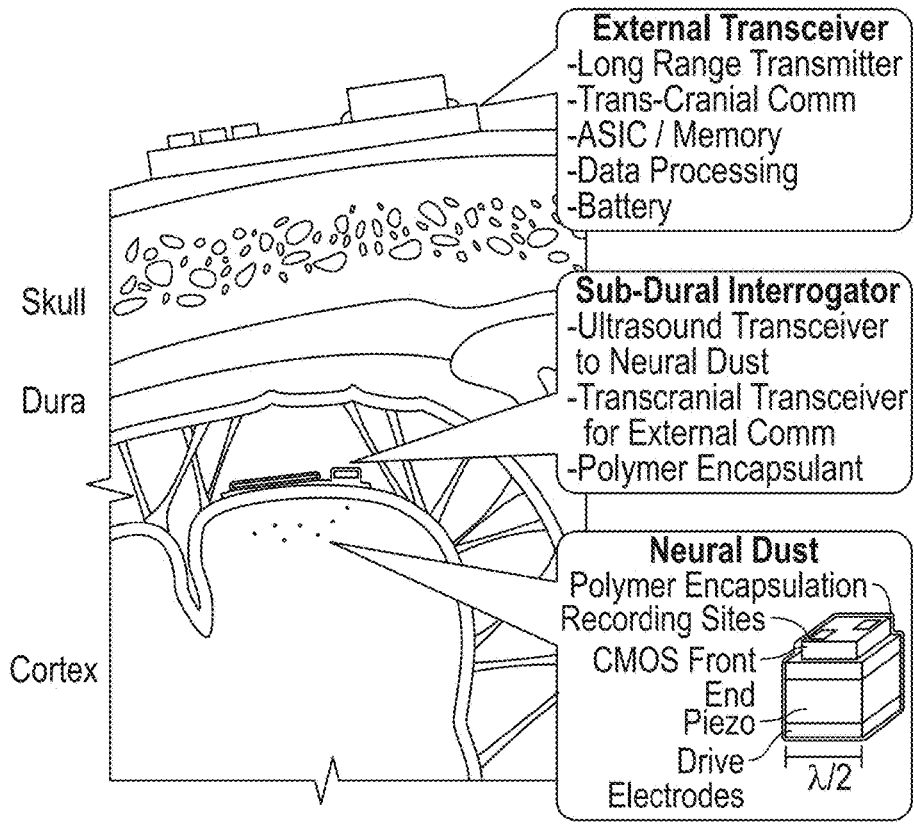
FIG. 1 is a schematic of a neural dust system, including an external transceiver, a sub-dural interrogator, and a neural dust mote, as described in Seo et al., *Neural dust: an ultrasonic, low power solution for chronic brain-machine interfaces*, arXiv: 1307.2196v1 (Jul. 8, 2013).

The implantable device described herein includes a miniaturized ultrasonic transducer (such as a miniaturized piezoelectric transducer) and a physiological sensor. The miniaturized ultrasonic transducer receives ultrasonic energy from an interrogator (which may be external or implanted), which powers the implantable device. The interrogator includes a transmitter and a receiver (which may be integrated into a combined transceiver), and the transmitter and the receiver may be on the same component or different components. The physiological sensor detects a physiological condition (such as pressure, temperature, strain, pressure, or an amount of one or more analytes), and generates an analog or digital electrical signal. Mechanical energy from the ultrasonic waves transmitted by the interrogator vibrates the miniaturized ultrasonic transducer on the implantable device, which generates an electrical current. The current flowing through the miniaturized ultrasonic transducer is modulated by the electrical circuitry in the implantable device based on the detected physiological condition. The miniaturized ultrasonic transducer emits an ultrasonic backscatter communicating information indicative of the sensed physiological condition, which is detected by the receiver components of the interrogator.

A significant advantage of the implantable device is the ability to detect one or more physiological conditions in deep tissue while being wirelessly powered, and to have those physiological conditions wirelessly transmitted to an interrogator, which can be external or relay the information to an external component. Thus, the implantable devices can remain in a subject for an extended period of time without needing to charge a battery or retrieve information stored on the device. These advantages, in turn, allow the device to be smaller and less expensive to manufacture. In another advantage, use of ultrasound allows for the relative time for data communication to be related to distance, which can aid in determining location or movement of the implantable device in real time.

Electromagnetic (EM) power transfer is not practical for powering small implantable devices due to power attenuation through tissue and the relatively large apertures (e.g. antennas or coils) required to capture such energy. See, for example, Seo et al., *Neural dust: an ultrasonic, low power solution for chronic brain-machine interfaces*, arXiv paper (July 2013). Use of EM to supply sufficient power to an implanted device would either require a shallow depth of the implant or would require excessive heating of the tissue to pass the EM waves through the tissue to reach the implantable device. In contrast to EM, ultrasonic power transfer provides low power attenuation in tissue due to the relatively low absorption of ultrasonic energy by tissue and the shorter wavelength of the ultrasonic waves (as compared to electromagnetic waves).

Ultrasonic transducers have found application in various disciplines including imaging, high intensity focused ultrasound (HIFU), nondestructive testing of materials, communication and power delivery through steel walls, underwater communications, transcutaneous power delivery, and energy harvesting. See, e.g., Ishida et al., *Insole Pedometer with Piezoelectric Energy Harvester and 2 V Organic Circuits*, IEEE J. Solid-State Circuits, vol. 48, no. 1, pp. 255-264 (2013); Wong et al., *Advantages of Capacitive Micromachined Ultrasonics Transducers (CMUTs) for High Intensity Focused Ultrasound (HIFU)*, IEEE Ultrasonics Symposium, pp. 1313-1316 (2007); Ozeri et al., *Ultrasonic Transcutaneous Energy Transfer for Powering Implanted Devices*, Ultrasonics, vol. 50, no. 6, pp. 556-566 (2010); and Richards et al., *Efficiency of Energy Conversion for Devices Containing a Piezoelectric Component*, J. Micromech. Microeng., vol. 14, pp. 717-721 (2004). Unlike electromagnetics, using ultrasound as an energy transmission modality never entered into widespread consumer application and was often overlooked because the efficiency of electromagnetics for short distances and large apertures is superior. However, at the scale of the implantable devices discussed herein and in tissue, the low acoustic velocity allows operation at dramatically lower frequencies, and the acoustic loss in tissue is generally substantially smaller than the attenuation of electromagnetics in tissue.

The relatively low acoustic velocity of ultrasound results in substantially reduced wavelength compared to EM. Thus, for the same transmission distance, ultrasonic systems are much more likely to operate in the far-field, and hence obtain larger spatial coverage than an EM transmitter. Further, the acoustic loss in tissue is fundamentally smaller than the attenuation of electromagnetics in tissue because acoustic transmission relies on compression and rarefaction of the tissue rather than time-varying electric/magnetic fields that generate displacement currents on the surface of the tissue.

It has been found that ultrasonic waves can be used to power and communicate with miniaturized implantable devices containing a miniaturized ultrasonic transducer (such as a bulk piezoelectric, a PMUT, or a CMUT) and a sensor.

The implantable devices described herein can be implanted in or used in a subject (e.g., an animal or a plant). In some embodiments, the subject is a mammal. Exemplary subjects include a rodent (such as a mouse, rat, or guinea pig), cat, dog, chicken, pig, cow, horse, sheep, rabbit, etc. In some embodiments, the subject is a human. The implantable devices can also be implanted in plants, such as agricultural plants, to measure physiological conditions.

Definitions

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

The term "miniaturized" refers to any material or component about 5 millimeters or less (such as about 4 mm or less, about 3 mm or less, about 2 mm or less, about 1 mm or less, or about 0.5 mm or less) in length in the longest dimension. In certain embodiments, a "miniaturized" material or component has a longest dimension of about 0.1 mm to about 5 mm (such as about 0.2 mm to about 5 mm, about 0.5 mm to about 5 mm, about 1 mm to about 5 mm, about 2 mm to about 5 mm, about 3 mm to about 5 mm, or about 4 mm to about 5 mm) in length. "Miniaturized" can also refer to any material or component with a volume of about 5 mm$^3$ or less (such as about 4 mm$^3$ or less, 3 mm$^3$ or less, 2 mm$^3$ or less, or 1 mm$^3$ or less). In certain embodiments, a "miniaturized" material or component has a volume of about 0.5 mm$^3$ to about 5 mm$^3$, about 1 mm$^3$ to about 5 mm$^3$, about 2 mm$^3$ to about 5 mm$^3$, about 3 mm$^3$ to about 5 mm$^3$, or about 4 mm$^3$ to about 5 mm$^3$.

A "piezoelectric transducer" is a type of ultrasonic transceiver comprising piezoelectric material. The piezoelectric material may be a crystal, a ceramic, a polymer, or any other natural or synthetic piezoelectric material.

A "non-responsive" ultrasonic wave is an ultrasonic wave with a reflectivity independent of a detected signal. A "non-responsive reflector" is a component of an implantable device that reflects ultrasonic waves such that the reflected waveform is independent of the detected signal.

It is understood that aspects and variations of the invention described herein include "consisting" and/or "consisting essentially of" aspects and variations.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention. The section headings used herein are for organizational purposes only and are not to be construed as limiting the subject matter described.

Features and preferences described above in relation to "embodiments" are distinct preferences and are not limited only to that particular embodiment; they may be freely combined with features from other embodiments, where technically feasible, and may form preferred combinations of features.

The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein. Further, sectional headings are provide for organizational purposes and are not to be considered limiting. Finally, the entire disclosure of the patents and publications referred in this application are hereby incorporated herein by reference for all purposes.

Interrogator

The interrogator can wirelessly communicate with one or more implantable devices using ultrasonic waves, which are used to power and/or operate the implantable device. The interrogator can further receive ultrasonic backscatter from the implantable device, which encodes information indicative of the sensed physiological condition. The interrogator includes one or more ultrasonic transducers, which can operate as an ultrasonic transmitter and/or an ultrasonic receiver (or as a transceiver, which can be configured to alternatively transmit or receive the ultrasonic waves). The one or more transducers can be arranged as a transducer array, and the interrogator can optionally include one or more transducer arrays. In some embodiments, the ultrasound transmitting function is separated from the ultrasound receiving function on separate devices. That is, optionally, the interrogator comprises a first device that transmits ultrasonic waves to the implantable device, and a second device that receives ultrasonic backscatter from the implantable device. In some embodiments, the transducers in the array can have regular spacing, irregular spacing, or be sparsely placed. In some embodiments the array is flexible. In some embodiments the array is planar, and in some embodiments the array is non-planar.

Figure 2A:
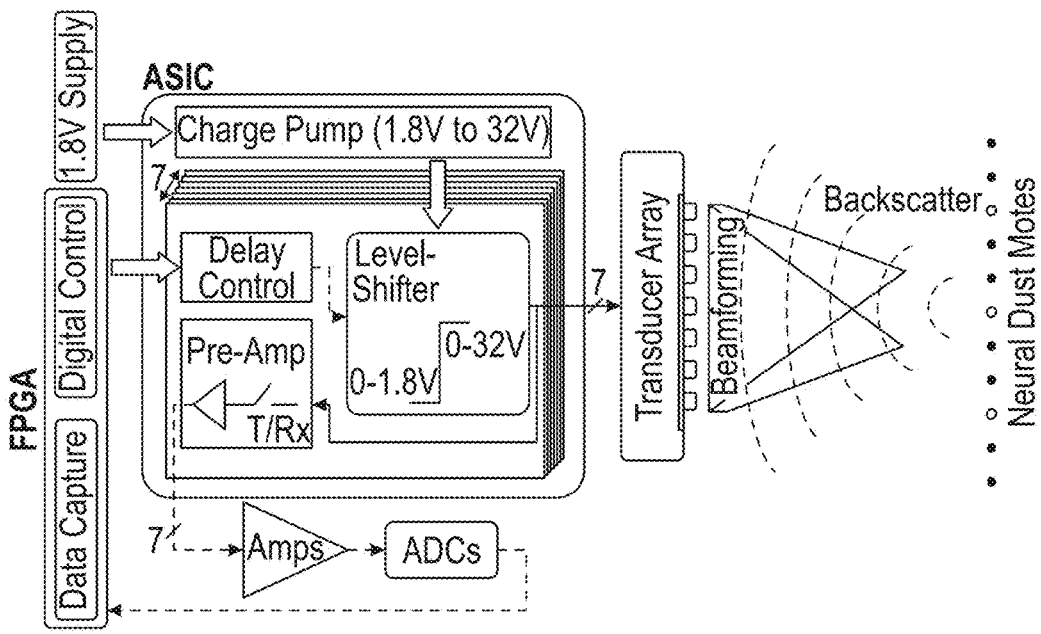
FIG. 2A is a block diagram of an exemplary interrogator for a system described herein. The illustrated interrogator includes an ultrasonic transducer array comprising a plurality of ultrasonic transducers. Each of the ultrasonic transducers in the array is operated by a channel, which includes a switch to alternatively configure the transducer to receive or transmit ultrasonic waves.

An exemplary interrogator is shown in FIG. 2A. The illustrated interrogator shows a transducer array with a plurality of ultrasonic transducers. In some embodiments, the transducer array includes 1 or more, 2 or more, 3 or more, 5 or more, 7 or more, 10 or more, 15 or more, 20 or more, 25 or more, 50 or more, 100 or more 250 or more, 500 or more, 1000 or more, 2500 or more, 5000 or more, or 10,000 or more transducers. In some embodiments, the transducer array includes 100,000 or fewer, 50,000 or fewer, 25,000 or fewer, 10,000 or fewer, 5000 or fewer, 2500 or fewer, 1000 or fewer, 500 or fewer, 200 or fewer, 150 or fewer, 100 or fewer, 90 or fewer, 80 or fewer, 70 or fewer, 60 or fewer, 50 or fewer, 40 or fewer, 30 or fewer, 25 or fewer, 20 or fewer, 15 or fewer, 10 or fewer, 7 or fewer or 5 or fewer transducers. The transducer array can be, for example a chip comprising 50 or more ultrasonic transducer pixels. The interrogator shown in FIG. 2A illustrates a single transducer array; however the interrogator can include 1 or more, 2 or more, or 3 or more separate arrays. In some embodiments, the interrogator includes 10 or fewer transducer arrays (such as 9, 8, 7, 6, 5, 4, 3, 2, or 1 transducer arrays). The separate arrays, for example, can be placed at different points of a subject, and can communicate to the same or different implantable devices. In some embodiments, the arrays are located on opposite sides of an implantable device. The interrogator can include an ASIC, which includes a channel for each transducer in the transducer array. In some embodiments, the channel includes a switch (indicated in FIG. 2A by "T/Rx"). The switch can alternatively configure the transducer connected to the channel to transmit ultrasonic waves or receive ultrasonic waves. The switch can isolate the ultrasound receiving circuit from the higher voltage ultrasound transmitting circuit. In some embodiments, the transducer connected to the channel is configured only to receive or only to transmit ultrasonic waves, and the switch is optionally omitted from the channel. The channel can include a delay control, which operates to control the transmitted ultrasonic waves. The delay control can control, for example, the phase shift, time delay, pulse frequency and/or wave shape (including amplitude and wavelength). The delay control can be connected to a level shifter, which shifts input pulses from the delay control to a higher voltage used by the transducer to transmit the ultrasonic waves. In some embodiments, the data representing the wave shape and frequency for each channel can be stored in a 'wave table'. This allows the transmit waveform on each channel to be different. Then, delay control and level shifters can be used to 'stream' out this data to the actual transmit signals to the transducer array. In some embodiments, the transmit waveform for each channel can be produced directly by a high-speed serial output of a microcontroller or other digital system and sent to the transducer element through a level shifter or high-voltage amplifier. In some embodiments, the ASIC includes a charge pump (illustrated in FIG. 2A) to convert a first voltage supplied to the ASIC to a higher second voltage, which is applied to the channel. The channels can be controlled by a controller, such as a digital controller, which operates the delay control. In the ultrasound receiving circuit, the received ultrasonic waves are converted to current by the transducers (set in a receiving mode), which is transmitted to a data capture circuit. In some embodiments, an amplifier, an analog-to-digital converter (ADC), a variable-gain-amplifier, or a time-gain-controlled variable-gain-amplifier which compensates for tissue loss, and/or a band pass filter is included in the receiving circuit. The ASIC can draw power from a power supply, such as a battery (which is preferred for a wearable embodiment of the interrogator). In the embodiment illustrated in FIG. 2A, a 1.8V supply is provided to the ASIC, which is increased by the charge pump to 32V, although any suitable voltage can be used. In some embodiments, the interrogator includes a processor and or a non-transitory computer readable memory. In some embodiments, the channel described above does not include a T/Rx switch but instead contains independent Tx (transmit) and Rx (receive) with a high-voltage Rx (receiver circuit) in the form of a low noise amplifier with good saturation recovery. In some embodiments, the T/Rx circuit includes a circulator. In some embodiments, the transducer array contains more transducer elements than processing channels in the interrogator transmit/receive circuitry, with a multiplexer choosing different sets of transmitting elements for each pulse. For example, 64 transmit receive channels connected via a 3:1 multiplexer to 192 physical transducer elements—with only 64 transducer elements active on a given pulse.

Figure 2B:
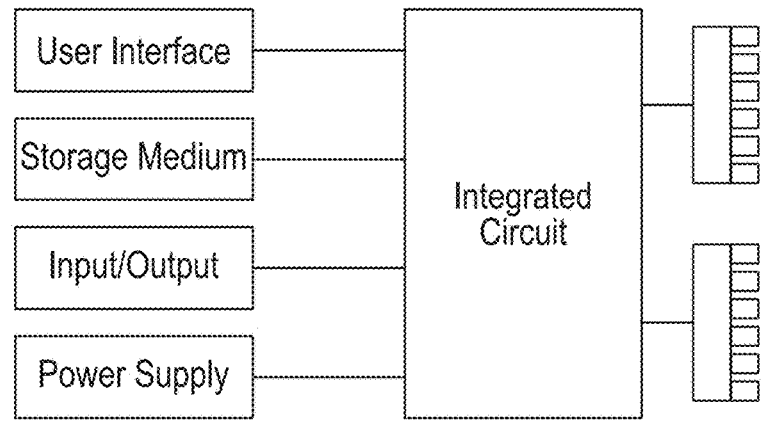
FIG. 2B is a schematic of another exemplary interrogator for a system described herein. The illustrated interrogator includes two ultrasonic transducer arrays, with each ultrasonic transducer array including a plurality of ultrasonic transducers. The interrogator also includes an integrated circuit (which can include a digital circuit, which can include a processor). The integrated circuit is connected to a user interface (which can include a display, keyboard, buttons, etc.), a storage medium (i.e., a non-transitory memory), an input/output (which may be wireless, such as a Bluetooth), and a power supply (such as a battery).

FIG. 2B illustrates another embodiment of interrogator. As shown in FIG. 2B, the interrogator includes one or more transducers 202. Each transducer 202 is connected to a transmitter/receiver switch 204, which can alternatively configure the transducer to transmit or receive ultrasonic waves. The transmitter/receiver switch is connected to a processor 206 (such as a central processing unit (CPU), a custom dedicated processor ASIC, a field programmable gate array (FPGA), microcontroller unit (MCU), or a graphics processing unit (GPU)). In some embodiments, the interrogator further includes an analog-digital converter (ADC) or digital-to-analog converter (DAC). The interrogator can also include a user interface (such as a display, one or more buttons to control the interrogator, etc.), a memory, a power supply (such as a battery), and/or an input/output port (which may be wired or wireless).

In some embodiments, the interrogator is implantable. An implanted interrogator may be preferred when the implantable devices are implanted in a region blocked by a barrier that does not easily transmit ultrasonic waves. For example, the interrogator can be implanted subcranially, either subdurally or supradurally. A subcranial interrogator can communicate with implantable devices that are implanted in the brain. Since ultrasonic waves are impeded by the skull, the implanted subcranial interrogator allows for communication with the implantable devices implanted in the brain. In another example, an implantable interrogator can be implanted as part of, behind or within another implanted device, such as a bone plate. The implanted interrogator can communicate with an external device, for example by EM or RF signals.

Figure 3A:
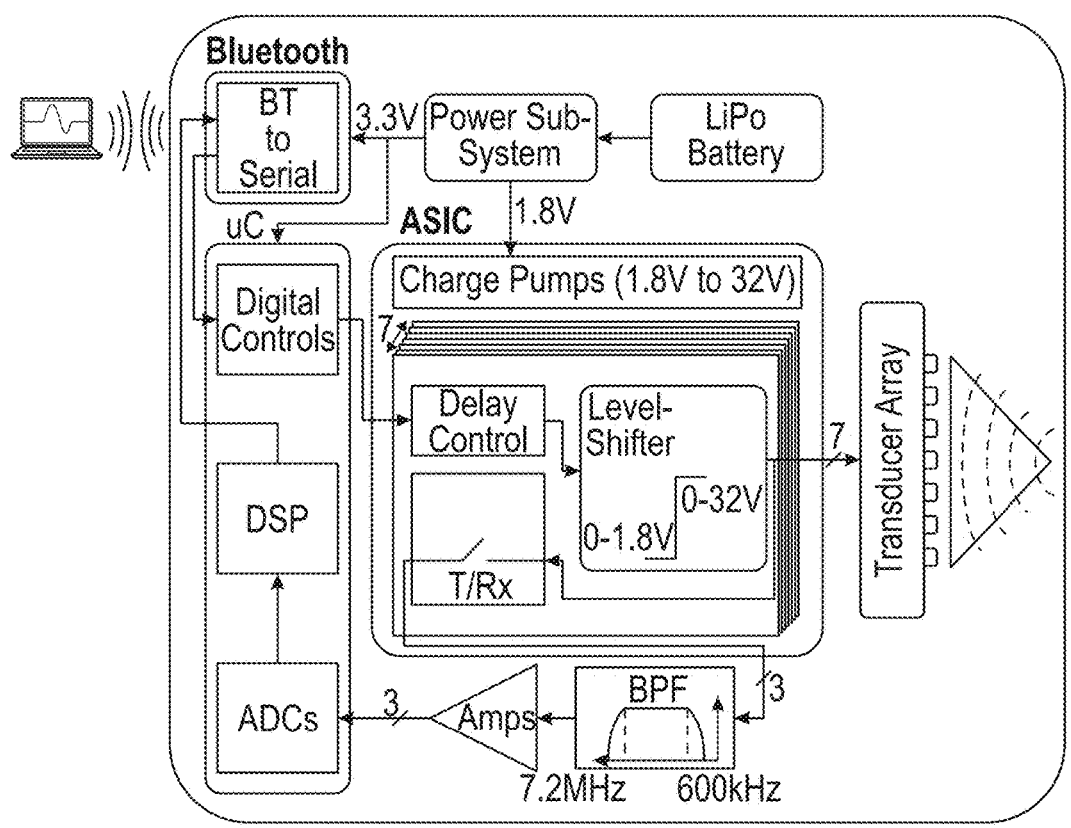
FIG. 3A shows a block diagram of an exemplary interrogator that can be worn by a subject. The interrogator includes a wireless communication system (a Bluetooth radio, in the illustration), which can be used to communicate with a computer system.
Figure 3B:
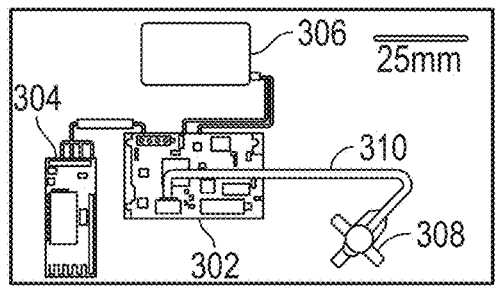
FIG. 3B shows an exploded view of a wearable interrogator. The interrogator includes a battery, a wireless communication system, and a transducer array.
Figure 3C:
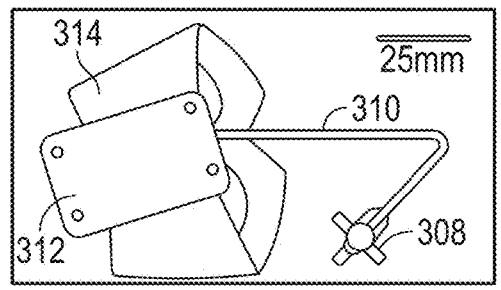
FIG. 3C shows the wearable interrogator shown in FIG. 3B fully assembled with a harness for attachment to a subject.
Figure 3D:
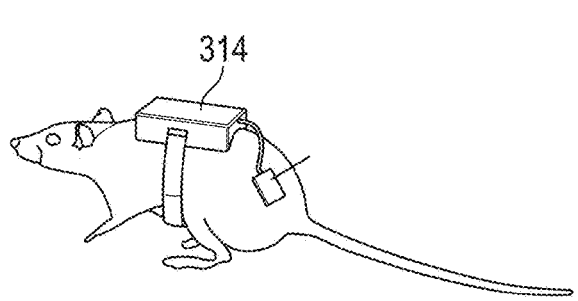
FIG. 3D illustrates the wearable interrogator attached a subject, namely a rodent (although could be any type of animal, such as a human, dog, cat, horse, cow, pig, sheep, goat, chicken, monkey, rat or mouse). The interrogator includes a transducer array, which is fixed to the body of the subject by an adhesive.
Figure 3E:
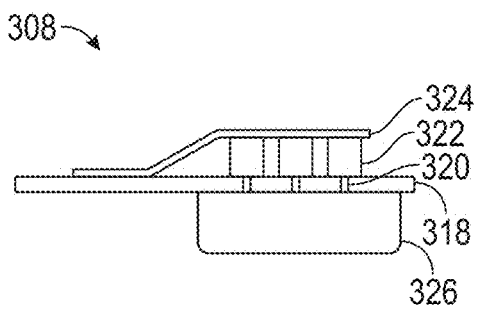
FIG. 3E illustrates a cross-section of the transducer array of the interrogator shown in FIGS. 3A-D.

In some embodiments, the interrogator is external (i.e., not implanted). By way of example, the external interrogator can be a wearable, which may be fixed to the body by a strap or adhesive. In another example, the external interrogator can be a wand, which may be held by a user (such as a healthcare professional). In some embodiments, the interrogator can be held to the body via suture, simple surface tension, a clothing-based fixation device such as a cloth wrap, a sleeve, an elastic band, or by sub-cutaneous fixation. The transducer or transducer array of the interrogator may be positioned separately from the rest of the transducer. For example, the transducer array can be fixed to the skin of a subject at a first location (such as proximal to one or more implanted devices), and the rest of the interrogator may be located at a second location, with a wire tethering the transducer or transducer array to the rest of the interrogator. FIG. 3A-E shows an example of a wearable external interrogator. FIG. 3A shows a block diagram of the interrogator, which includes a transducer array comprising a plurality of transducers, an ASIC comprising a channel for each transducer in the transducer array, a battery (lithium polymer (LiPo) battery, in the illustrated example), and a wireless communication system (such as a Bluetooth system). FIG. 3B illustrates an exploded view of a wearable interrogator, including a printed circuit board (PCB) 302, which includes the ASIC, a wireless communication system 304, a battery 306, an ultrasonic transducer array 308, and a wire 310 tethering the ultrasonic transducer array 308 to the ASIC. FIG. 3C shows the wearable interrogator 312 shown in FIG. 3B with a harness 314, which can be used to attach the interrogator to a subject. FIG. 3D shows the assembled interrogator 316 attached to a subject, with the transducer array 308 attached at a first location, and the rest of the interrogator attached to a second location. FIG. 3E shows a cross-section schematic of an exemplary ultrasonic transducer array 308, which includes a circuit board 318, vias 320 attaching each transducer 322 to the circuit board 318, a metalized polyester film 324, and an absorptive backing layer 326. The metalized polyester film 324 can provide a common ground and acoustic matching for the transducers, while the absorptive backing layer 326 (such as tungsten powder filled polyurethane) can reduce ringing of the individual transducers.

The specific design of the transducer array depends on the desired penetration depth, aperture size, and size of the individual transducers within the array. The Rayleigh distance, R, of the transducer array is computed as:

$$R = \frac{D^2 - \lambda^2}{4\lambda} \approx \frac{D^2}{4\lambda}, D^2 \gg \lambda^2$$

where D is the size of the aperture and $\lambda$ is the wavelength of ultrasound in the propagation medium (i.e., the tissue). As understood in the art, the Rayleigh distance is the distance at which the beam radiated by the array is fully formed. That is, the pressure filed converges to a natural focus at the Rayleigh distance in order to maximize the received power. Therefore, in some embodiments, the implantable device is approximately the same distance from the transducer array as the Rayleigh distance.

The individual transducers in a transducer array can be modulated to control the Raleigh distance and the position of the beam of ultrasonic waves emitted by the transducer array through a process of beamforming or beam steering. Techniques such as linearly constrained minimum variance (LCMV) beamforming can be used to communicate a plurality of implantable devices with an external ultrasonic transceiver. See, for example, Bertrand et al., *Beamforming Approaches for Untethered, Ultrasonic Neural Dust Motes for Cortical Recording: a Simulation Study*, IEEE EMBC (August 2014). In some embodiments, beam steering is performed by adjusting the power or phase of the ultrasonic waves emitted by the transducers in an array.

In some embodiments, the interrogator includes one or more of instructions for beam steering ultrasonic waves using one or more transducers, instructions for determining the relative location of one or more implantable devices, instructions for monitoring the relative movement of one or more implantable devices, instructions for recording the relative movement of one or more implantable devices, and instructions for deconvoluting backscatter from a plurality of implantable devices.

Communication Between an Implantable Device and an Interrogator

The implantable device and the interrogator wirelessly communicate with each other using ultrasonic waves. The implantable device receives ultrasonic waves from the interrogator through a miniaturized ultrasonic transducer on the implantable device. Vibrations of the miniaturized ultrasonic transducer on the implantable device generate a voltage across the electric terminals of the transducer and a current flows through the device, including the sensor and/or, if present, the ASIC. Depending on the physiological condition detected by the sensor, information relating to the physiological condition can alter the current, which in turns modulates the backscatter from the miniaturized ultrasonic transducer. The sensor system (optionally including an ASIC) presents electrical impedance to the electric terminals on the transducer. If this impedance changes, the mechanical impedance of the transducer (as seen from outside the device) changes, resulting in changes in backscatter. Thus, the sensor system modulates the electrical impedance presented to the transducer to effect backscatter communication. The backscatter is then received by an external ultrasonic transceiver (which may be the same or different from the external ultrasonic transceiver that transmitted the initial ultrasonic waves). The information from the sensor can thus be encoded by changes in amplitude, frequency, or phase of the backscattered ultrasound waves.

Figure 4:
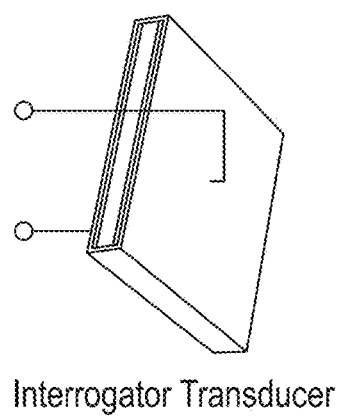
FIG. 4 provides a schematic showing the communication between a transducer from an interrogator and an implantable device having a miniaturized ultrasonic transducer. The interrogator transmits ultrasonic waves to the implantable device, and the miniaturized ultrasonic transducer emits ultrasonic backscatter modulated by the sensor. The backscatter is then received by the interrogator.
Figure 4:
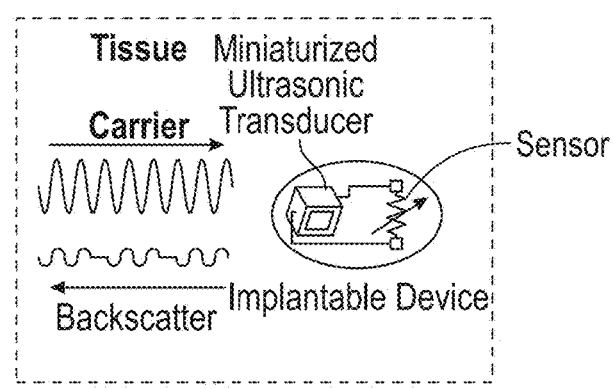

FIG. 4 illustrates an interrogator in communication with an implantable device. The external ultrasonic transceiver emits ultrasonic waves ("carrier waves"), which can pass through tissue. The carrier waves cause mechanical vibrations on the miniaturized ultrasonic transducer (e.g., a miniaturized bulk piezoelectric transducer, a PMUT, or a CMUT). A voltage across the miniaturized ultrasonic transducer is generated, which imparts a current flowing through a sensor on the implantable device. In some embodiments, the implantable device includes an ASIC, and current flows from the miniaturized ultrasonic transducer, through the ASIC, to the radiation detector, back to the ASIC, and returns to the miniaturized ultrasonic transducer. The current flowing through the miniaturized ultrasonic transducer causes the transducer on the implantable device to emit backscatter ultrasonic waves. The current flowing through the miniaturized ultrasonic transducer changes the amplitude, frequency, and/or phase of the backscatter ultrasonic wave emitted or reflected from the ultrasonic transducer. Since the physiological condition affects the current returning to the ASIC and/or the miniaturized ultrasonic transducer, the backscatter waves encode information relating to the physiological condition. The backscatter waves can be detected by the interrogator, and can be deciphered to determine the physiological condition or a change in the physiological condition.

Communication between the interrogator and the implantable device can use a pulse-echo method of transmitting and receiving ultrasonic waves. In the pulse-echo method, the interrogPator transmits a series of interrogation pulses at a predetermined frequency, and then receives backscatter echoes from the implanted device. In some embodiments, the pulses are about 200 nanoseconds (ns) to about 1000 ns in length (such as about 300 ns to about 800 ns in length, about 400 ns to about 600 ns in length, or about 540 ns in length). In some embodiments, the pulses are about 100 ns or more in length (such as about 150 ns or more, 200 ns or more, 300 ns or more, 400 ns or more, 500 ns or more, 540 ns or more, 600 ns or more, 700 ns or more, 800 ns or more, 900 ns or more, 1000 ns or more, 1200 ns or more, or 1500 ns or more in length). In some embodiments, the pulses are about 2000 ns or less in length (such as about 1500 ns or less, 1200 ns or less, 1000 ns or less, 900 ns or less, 800 ns or less, 700 ns or less, 600 ns or less, 500 ns or less, 400 ns or less, 300 ns or less, 200 ns or less, or 150 ns or less in length). In some embodiments, the pulses are separated by a dwell time. In some embodiments, the dwell time is about 100 ns or more in length (such as about 150 ns or more, 200 ns or more, 300 ns or more, 400 ns or more, 500 ns or more, 540 ns or more, 600 ns or more, 700 ns or more, 800 ns or more, 900 ns or more, 1000 ns or more, 1200 ns or more, or 1500 ns or more in length). In some embodiments, the dwell time is about 2000 ns or less in length (such as about 1500 ns or less, 1200 ns or less, 1000 ns or less, 900 ns or less, 800 ns or less, 700 ns or less, 600 ns or less, 500 ns or less, 400 ns or less, 300 ns or less, 200 ns or less, or 150 ns or less in length). In some embodiments, the pulses are square, rectangular, triangular, sawtooth, or sinusoidal. In some embodiments, the pulse output can be two-level (GND and POS), three-level (GND, NEG, POS), 5-level, or any other multiple-level (for example, if using 24-bit DAC). In some embodiments, the pulses are continuously transmitted by the interrogator during operation. In some embodiments, when the pulses are continuously transmitted by the interrogator a portion of the transducers on the interrogator are configured to receive ultrasonic waves and a portion of the transducers on the interrogator are configured to transmit ultrasonic waves. Transducers configured to receive ultrasonic waves and transducers configured to transmit ultrasonic waves can be on the same transducer array or on different transducer arrays of the interrogator. In some embodiments, a transducer on the interrogator can be configured to alternatively transmit or receive the ultrasonic waves. For example, a transducer can cycle between transmitting one or more pulses and a pause period. The transducer is configured to transmit the ultrasonic waves when transmitting the one or more pulses, and can then switch to a receiving mode during the pause period. In some embodiments, the one or more pulses in the cycle includes about 1 to about 10 pulses (such as about 2 to about 8, or about 4 to about 7, or about 6) pulses of ultrasonic waves in any given cycle. In some embodiments, the one or more pulses in the cycle includes about 1 or more, 2 or more, 4 or more, 6 or more, 8 or more, or 10 or more pulses of ultrasonic waves in any given cycle. In some embodiments, the one or more pulses in the cycle includes about 20 or fewer, about 15 or fewer, about 10 or fewer, about 8 or fewer, or about 6 or fewer pulses in the cycle. The pulse cycle can be regularly repeated, for example every about 50 microseconds (μs) to about 300 μs (such as about every 75 μs to about 200 μs, or every about 100 μs) during operation. In some embodiments, the cycle is reaped every 50 μs or longer, every 100 μs or longer, every 150 μs or longer, every 200 μs or longer, every 250 μs or longer, or every 300 μs or longer. In some embodiments, the cycle is repeated every 300 μs or sooner, every 250 μs or sooner, every 200 μs or sooner, every 150 μs or sooner, or every 100 μs or sooner. The cycle frequency can set, for example, based on the distance between the interrogator and the implantable device and/or the speed at which the transducer can toggle between the transmitting and receiving modes.

FIG. 5 illustrates cycled pulse-echo ultrasonic communication between the interrogator and the implantable device. FIG. 5A shows a series of pulse cycles with a frequency of every 100 microseconds. During the transmission of the pulses, the transducers in the array are configured to transmit the ultrasonic waves. After the pulses are transmitted, the transducers are configured to receive backscattered ultrasonic waves. FIG. 5B shows a zoom-in view of a cycle, which shows six pulses of ultrasonic waves, with a frequency of every 540 nanoseconds. Backscattered ultrasonic waves detected by the interrogator are shown in FIG. 5C, with a zoom-in view of a single pulse shown in FIG. 5D. As shown in FIG. 5D, the ultrasonic backscatter received from the implantable device can be analyzed, which may include filtering (for example, to remove the wave decay) the backscattered waves, rectifying the backscattered waves, and integrating the waves to determine the data encoded by the waves. In some embodiments, the backscatter waves are analyzed using a machine learning algorithm. FIG. 5E shows a zoomed in version of the filtered backscattered waves. The backscatter wave shown in FIG. 5E includes four distinct regions corresponding to reflections arising from mechanical boundaries: (1) reflection from the biocompatible material that encapsulates the implantable device; (2) reflection from the top surface of the miniaturized ultrasonic transducer; (3) reflection from the boundary between the printed circuit board and the miniaturized ultrasonic transducer; and (4) reflection from the back of the printed circuit board. The amplitude of the backscatter waves reflected from the surface of the miniaturized transducer changed as a function of changes in impedance of the current returning to the miniaturized ultrasonic transducer, and can be referred to as the "responsive backscatter" since this region of the backscatter encodes information relating to the sensed physiological condition. The other regions of the ultrasonic backscatter can be referred to as "non-responsive backscatter," and are useful in determining the position of the implantable device, movement of the implantable device, and/or temperature changes proximal to the implantable device, as explained below. In some embodiments, the device further comprises a non-responsive reflector. In some embodiments, the non-responsive reflector is a cube. In some embodiments, the non-responsive reflector comprises silicon. In some embodiments, the non-responsive reflector is a surface of rigid material. The non-responsive reflector is attached to the implantable device but electrically isolated, and can reflect ultrasonic waves that are not responsive to changes in sensor or ASIC impedance, for example due to a sensed physiological condition by the sensor.

The frequency of the ultrasonic waves transmitted by the transducer can be set depending on the drive frequency or resonant frequency of the miniaturized ultrasonic transducer on the implantable device. In some embodiments, the miniaturized ultrasonic transducers are broad-band devices. In some embodiments, the miniaturized ultrasonic transducers are narrow-band. For example, in some embodiments the frequency of the pulses is within about 20% or less, within about 15% or less, within about 10% or less, within about 5% or less of the resonant frequency of the miniaturized ultrasonic transducer. In some embodiments, the pulses are set to a frequency about the resonant frequency of the miniaturized ultrasonic transducer. In some embodiments, the frequency of the ultrasonic waves is between about 100 kHz and about 100 MHz (such as between about 100 kHz and about 200 kHz, between about 200 kHz and about 500 kHz, between about 500 kHz and about 1 MHz, between about 1 MHz and about 5 MHz, between about 5 MHz and about 10 MHz, between about 10 MHz and about 25 MHz, between about 25 MHz and about 50 MHz, or between about 50 MHz and about 100 MHz). In some embodiments, the frequency of the ultrasonic waves is about 100 kHz or higher, about 200 kHz or higher, about 500 kHz or higher, about 1 MHz or higher, about 5 MHz or higher, about 10 MHz or higher, about 25 MHz or higher, or about 50 MHz or higher. In some embodiments, the frequency of the ultrasonic waves is about 100 MHz or lower, about 50 MHz or lower, about 25 MHz or lower, about 10 MHz or lower, about 5 MHz or lower, about 1 MHz or lower, about 500 kHz or lower, or about 200 kHz or lower. Higher frequency allows for a smaller miniaturized ultrasonic transducer on the implantable device. However, higher frequency also limits the depth of communication between the ultrasonic transducer and the implantable device. In some embodiments, the implantable device and the ultrasonic transducer are separated by about 0.1 cm to about 15 cm (such as about 0.5 cm to about 10 cm, or about 1 cm to about 5 cm). In some embodiments, the implantable device and the ultrasonic transducer are separated by about 0.1 cm or more, about 0.2 cm or more, about 0.5 cm or more, about 1 cm or more, about 2.5 cm or more, about 5 cm or more, about 10 cm or more, or about 15 cm or more. In some embodiments, the implantable device and the ultrasonic transducer are separated by about 20 cm or less, about 15 cm or less, about 10 cm or less, about 5 cm or less, about 2.5 cm or less, about 1 cm or less, or about 0.5 cm or less.

In some embodiments, the backscattered ultrasound is digitized by the implantable device. For example, the implantable device can include an oscilloscope or analog-to-digital converter (ADC) and/or a memory, which can digitally encode information in current (or impedance) fluctuations. The digitized current fluctuations, which reflect data sensed by the sensor, are received by the ultrasonic transducer, which then transmits digitized acoustic waves. The digitized data can compress the analog data, for example by using singular value decomposition (SVD) and least squares-based compression. In some embodiments, the compression is performed by a correlator or pattern detection algorithm. The backscatter signal may go through a series of non-linear transformation, such as $4^{th}$ order Butterworth bandpass filter rectification integration of backscatter regions to generate a reconstruction data point at a single time instance. Such transformations can be done either in hardware (i.e., hard-coded) or in software.

In some embodiments, an interrogator communicates with a plurality of implantable devices. This can be performed, for example, using multiple-input, multiple output (MIMO) system theory. For example, communication between the interrogator and the plurality of implantable devices using time division multiplexing, spatial multiplexing, or frequency multiplexing. In some embodiments, two or more (such as 3, 4, 5, 6, 7, 8, 9, 10 or more, 12 or more, about 15 or more, about 20 or more, about 25 or more, about 50 or more, or about 100 or more) implantable devices communicate with the interrogator. In some embodiments, about 200 or fewer implantable devices (such as about 150 or fewer, about 100 or fewer, about 50 or fewer, about 25 or fewer, about 20 or fewer, about 15 or fewer, about 12 or fewer, or about 10 or fewer implantable devices) are in communication with the interrogator. The interrogator can receive a combined backscatter from the plurality of the implantable devices, which can be deconvoluted, thereby extracting information from each implantable device. In some embodiments, interrogator focuses the ultrasonic waves transmitted from a transducer array to a particular implantable device through beam steering. The interrogator focuses the transmitted ultrasonic waves to a first implantable device, receives backscatter from the first implantable device, focuses transmitted ultrasonic waves to a second implantable device, and receives backscatter from the second implantable device. In some embodiments, the interrogator transmits ultrasonic waves to a plurality of implantable devices, and then receives ultrasonic waves from the plurality of implantable devices.

In some embodiments, the interrogator is used to determine the location or velocity of the implantable device. Velocity can be determined, for example, by determining the position or movement of a device over a period of time. The location of the implantable device can be a relative location, such as the location relative to the transducers on the interrogator. A plurality of transducers, which may be disposed on the same transducer array or two or more different transducer arrays, can collect backscatter ultrasonic waves from an implantable device. Based on the differences between the backscatter waveform arising from the same implantable device and the known location of each transducer, the position of the implantable device can be determined. This can be done, for example by triangulation, or by clustering and maximum likelihood. The differences in the backscatter may be based on responsive backscatter waves, non-responsive backscatter waves, or a combination thereof.

In some embodiments, the interrogator is used to track movement of the implantable device. Movement of the implantable device that can be tracked by the interrogator includes lateral and angular movement. Such movement may arise, for example, due to shifting of one or more organs such as the liver, stomach, small or large intestine, kidney, pancreas, gallbladder, bladder, ovaries, uterus, or spleen (which may be the result, for example, of respiration or movement of the subject) or variations in blood flow (such as due to a pulse). Thus, in some embodiments, the implantable device is useful for tracking movement of an organ or a pulse rate. Movement of the implantable device can be tracked, for example, by monitoring changes in the non-responsive backscatter waves. In some embodiments, movement of the implantable device is determined my comparing the relative location of the implantable device at a first time point to the relative location of the implantable device at a second time point. For example, as described above, the location of an implantable device can be determined using a plurality of transducers on the interrogated (which may be on a single array or on two or more arrays). A first location of the implantable device can be determined at a first time point, and a second location of the implantable device can be determined at a second time point, and a movement vector can be determined based on the first location at the first time point and the second location at the second time point.

Implantable Device

The implantable device includes a miniaturized ultrasonic transducer (such as a miniaturized piezoelectric transducer, a capacitive micro-machined ultrasonic transducer (CMUT), or a piezoelectric micro-machined ultrasonic transducer (PMUT)) and a physiological sensor (such as a temperature sensor, an oxygen sensor, a pH sensor, a strain sensor, a pressure sensor, or a glucose sensor). In some embodiments, an application specific integrated circuit (ASIC) is included in the implantable device, which can communicate between the physiological sensor and the miniaturized ultrasonic transducer. The interrogator transmits ultrasonic waves, which can power and communicate with the implantable device through the miniaturized ultrasonic transducer on the implantable device. The changed impedance impacts the current flowing within the miniaturized ultrasonic transducer, which impacts the ultrasonic backscatter. Thus, a change in the physiological condition impacts the ultrasonic backscatter, which can be detected by the interrogator. FIG. 6A illustrates a schematic of the implantable device with a miniaturized ultrasonic transducer 602 and a physiological sensor 604. FIG. 6B illustrates a schematic of the implantable device with a miniaturized ultrasonic transducer 606, an ASIC 608, and a physiological sensor 610.

The implantable devices are miniaturized, which allows for comfortable and long-term implantation while limiting tissue inflammation that is often associated with implantable devices. In some embodiments, the longest dimension of the device is about 5 mm or less, about 4 mm or less, about 3 mm or less, about 2 mm or less, about 1 mm or less, about 0.5 mm or less, about 0.3 mm or less, about 0.1 mm or less in length. In some embodiments, the longest dimension of the device is about 0.05 mm or longer, about 0.1 mm or longer, about 0.3 mm or longer, about 0.5 mm or longer, about 1 mm or longer, about 2 mm or longer, or about 3 mm or longer in the longest dimension of the device. In some embodiments, the longest dimension of the device is about 0.04 mm to about 5 mm in length, about 0.05 mm to about 4 mm in length, about 0.07 mm to about 3 mm in length, about 0.08 mm to about 3 mm in length, or about 1 mm to about 2 mm in length.

In some embodiments, the implantable device has a volume of about 5 mm$^3$ or less (such as about 4 mm$^3$ or less, 3 mm$^3$ or less, 2 mm$^3$ or less, or 1 mm$^3$ or less). In certain embodiments, the implantable device has a volume of about 0.5 mm$^3$ to about 5 mm$^3$, about 1 mm$^3$ to about 5 mm$^3$, about 2 mm$^3$ to about 5 mm$^3$, about 3 mm$^3$ to about 5 mm$^3$, or about 4 mm$^3$ to about 5 mm$^3$. The small size of the implantable device allows for implantation of the device using a biopsy needle.

In some embodiments, the implantable device is implanted in a subject. The subject can be for example, an animal, such as a mammal. In some embodiments, the subject is a human, dog, cat, horse, cow, pig, sheep, goat, chicken, monkey, rat, or mouse. In some embodiments, the subject is a plant. Implantable devices implanted in plants can be useful, for example, for monitoring conditions of agricultural plants.

In some embodiments, the implantable device or a portion of the implantable device (such as the miniaturized ultrasonic transducer, the ASIC, or all or a portion of the sensor) is encapsulated by a biocompatible material (such as a biocompatible polymer), for example a copolymer of N-vinyl-2-pyrrolidinone (NVP) and n-butylmethacrylate (BMA), polydimethylsiloxane (PDMS), parylene, polyimide, silicon nitride, silicon dioxide, alumina, niobium, hydroxyapatite, or silicon carbide. The silicon carbide can be amorphous silicon carbide or crystalline silicon carbide. The biocompatible material is preferably impermeable to water to avoid damage or interference to electronic circuitry within the device. In some embodiments, the implantable device or portion of the implantable device is encapsulated by a ceramic (for example, alumina or titania) or a metal (for example, steel or titanium).

In some embodiments, the miniaturized ultrasonic transducer and, if present, the ASIC, are disposed on a printed circuit board (PCB). The sensor can optionally be disposed on the PCB, or can otherwise be connected to the ASIC. FIGS. 7A and 7B illustrate exemplary configurations of the implantable device including a PCB. FIG. 7A shows the piezoelectric transducer 702 and an ASIC 704 disposed on a first side 706 of the PCB 708. A first electrode 710 and a second electrode 712 are disposed on a second side 714 of the PCB 708. The first electrode 710 and the second electrode 712 can be, for example, components of the sensor. FIG. 7B sows the piezoelectric transducer 714 on a first side 716 of the PCB 718, and the ASIC 720 on the second side 722 of the PCB 718. A first electrode 724 is disposed on the first side 716 of the PCB, and a second electrode 726 is disposed on the second side 722 of the PCB 718. The first electrode 724 and the second electrode 726 can be, for example, components of the sensor.

The miniaturized ultrasonic transducer of the implantable device can be a micro-machined ultrasonic transducer, such as a capacitive micro-machined ultrasonic transducer (CMUT) or a piezoelectric micro-machined ultrasonic transducer (PMUT), or can be a bulk piezoelectric transducer. Bulk piezoelectric transducers can be any natural or synthetic material, such as a crystal, ceramic, or polymer. Exemplary bulk piezoelectric transducer materials include barium titanate (BaTiO$_3$), lead zirconate titanate (PZT), zinc oxide (ZO), aluminum nitride (AlN), quartz, berlinite (AlPO$_4$), topaz, langasite (La$_3$Ga$_5$SiO$_{14}$), gallium orthophosphate (GaPO$_4$), lithium niobate (LiNbO$_3$), lithium tantalite (LiTaO$_3$), potassium niobate (KNbO$_3$), sodium tungstate (Na$_2$WO$_3$), bismuth ferrite (BiFeO$_3$), polyvinylidene (di)fluoride (PVDF), and lead magnesium niobate-lead titanate (PMN-PT).

In some embodiments, the miniaturized bulk piezoelectric transducer is approximately cubic (i.e., an aspect ratio of about 1:1:1 (length:width:height). In some embodiments, the piezoelectric transducer is plate-like, with an aspect ratio of about 5:5:1 or greater in either the length or width aspect, such as about 7:5:1 or greater, or about 10:10:1 or greater. In some embodiments, the miniaturized bulk piezoelectric transducer is long and narrow, with an aspect ratio of about 3:1:1 or greater, and where the longest dimension is aligned to the direction of propagation of the carrier ultrasound wave. In some embodiments, one dimension of the bulk piezoelectric transducer is equal to one half of the wavelength ($\lambda$) corresponding to the drive frequency or resonant frequency of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 µm to about 1000 µm (such as about 40 µm to about 400 µm, about 100 µm to about 250 µm, about 250 µm to about 500 µm, or about 500 µm to about 1000 µm). In some embodiments, the height of the piezoelectric transducer is about 5 mm or less (such as about 4 mm or less, about 3 mm or less, about 2 mm or less, about 1 mm or less, about 500 µm or less, about 400 or less, 250 µm or less, about 100 µm or less, or about 40 µm or less). In some embodiments, the height of the piezoelectric transducer is about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in length.

In some embodiments, the ultrasonic transducer has a length of about 5 mm or less such as about 4 mm or less, about 3 mm or less, about 2 mm or less, about 1 mm or less, about 500 µm or less, about 400 µm or less, 250 µm or less, about 100 µm or less, or about 40 µm or less) in the longest dimension. In some embodiments, the ultrasonic transducer has a length of about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in the longest dimension.

The miniaturized ultrasonic transducer is connected two electrodes; the first electrode is attached to a first face of the transducer and the second electrode is attached to a second face of the transducer, wherein the first face and the second face are opposite sides of the transducer along one dimension. In some embodiments, the electrodes comprise silver, gold, platinum, platinum-black, poly(3,4-ethylenedioxythiophene (PEDOT), a conductive polymer (such as conductive PDMS or polyimide), or nickel. In some embodiments, the transducer is operated in shear-mode where the axis between the metallized faces (i.e., electrodes) of the transducer is orthogonal to the motion of the transducer.

The miniaturized ultrasonic transducer is connected to a sensor and, in some embodiments, an AISC. The ASIC, if present, can be integrated with the sensor or provide separately from the sensor.

The ASIC used in the implantable device depends, in part, on the sensor that is attached. In some embodiments, the AISC is fully integrated with the sensor, and in some embodiments the sensor is provided as a separate, but attached, component of the implantable device. In some embodiments, the implantable device includes two or more sensors, and one or more ASICs can be used with the two or more sensors. For example, in some embodiments, a single ASIC is used with two or more, three or more, four or more, or five or more sensors.

In some embodiments, the ASIC includes a power circuit, which is configured to power components of the implanted device. The power circuit can include, for example, a rectifier, a charge pump, and/or an energy storage capacitor. In some embodiments, the energy storage capacitor is included as a separate component. Ultrasonic waves that induce a voltage differential in the miniaturized ultrasonic transducer provide power for the implantable device, which can be managed by the power circuit.

In some embodiments, the ASIC comprises one or more analog circuit which utilizes the electrical power provided by the transducer to power one or more analog amplifiers, increasing the modulation depth of the signal modulated onto the backscatter impedance. In some embodiments the ASIC includes one or more digital circuits, which can include a memory and one or more circuit blocks or systems for operating the implantable device; these systems can include, for example an onboard microcontroller, a finite state machine implementation or digital circuits capable of executing programs stored on the implant or provided via ultrasonic communication between interrogator and implant. In some embodiments, the digital circuit includes an analog-to-digital converter (ADC), which can convert analog signal from the sensor into a digital signal. In some embodiments, the digital circuit includes a digital-to-analog converter (DAC), which converts a digital signal into an analog signal prior to directing the signal to a modulator.

The digital circuit can operate a modulation circuit (which can also be referred to as the "backscatter circuit"), which connects to the miniaturized ultrasonic transducer. The modulation circuit includes a switch, such as an on/off switch or a field-effect transistor (FET). An exemplary FET that can be used with some embodiments of the implantable device is a metal-oxide-semiconductor field-effect transistor (MOSFET). The modulation circuit can alter the impedance presented to the miniaturized ultrasonic transducer, and the variation in current passing through the transducer encodes signals transmitted by the digital circuit. The digital circuit can also operate one or more amplifiers, which amplifies the current directed to the switch. In embodiments where the digital circuit is omitted, the impedance in the modulation circuit can be directly controlled by the sensor.

In some embodiments, the ASIC includes a driver circuit, which provides current to one or more sensors. The driver circuit can be operated by the digital circuit if present. In some embodiments, one or more amplifiers are disposed between the driver circuit and the digital circuit. In some embodiments, the ASIC includes a front end circuit (such as a CMOS front end), which can receive a signal from the sensor. The signal received by the front end circuit can be relayed to the digital circuit.

FIG. 8A includes one embodiment of a miniaturized ultrasonic transducer (identified as the "piezo") connected to an ASIC. The ASIC includes a power circuit, a modulation circuit (or "backscatter circuit"), and a driver (the "stimulation circuit"). The power circuit includes an energy storage capacitor ("cap").

FIG. 8B illustrates another example of an ASIC 802 connected to the miniaturized ultrasonic transducer 804. In the illustrated embodiment, the miniaturized ultrasonic transducer 804 is connected to a power circuit 806. The power circuit 806 provides power to the other components of the ASIC, including the modulation circuit 808, the digital circuit 810, the driver 812, and the front end 814. The digital circuit 810 operates the driver 812, which can be connected to a sensor (not shown). The front end circuit 814 receives signal from the sensor and transmits the signal to the digital circuit 810. The digital circuit 810 can then control the modulation circuit 808, which controls impedance of the current returning to the miniaturized ultrasonic transducer 804.

Sensors

The implantable device includes one or more sensors. The sensors are configured to detect a physiological condition, such as temperature, oxygen concentration, pH, an analyte (such as glucose), strain, or pressure. Variation in the physiological condition modulates impedance, which in turn modulates current flowing miniaturized ultrasonic transducer on the implantable device. As explained above, this produces ultrasonic backscatter detected by the interrogator; changes in the ultrasonic backscatter waves reflect information about the physiological condition. In some embodiments, the system is configured to detect changes in the physiological system. In some embodiments, the system is configured detect a value or an approximate value of the physiological condition, for example by calibrating the ultrasonic backscatter to known values.

The implantable device may comprise one or more (such as 2, 3, 4, 5 or more) sensors, which may detect the same physiological condition or different physiological conditions. In some embodiments, the implantable device comprises 10, 9, 8, 7, 6 or 5 or fewer sensors). For example, in some embodiments, the implantable device comprises a first sensor configured to detect temperature and a second sensor configured to detect oxygen. Changes in both physiological conditions can be encoded in the ultrasonic backscatter waves, which can be deciphered by an external computing system.

In some embodiments, the sensor includes an optical detector. A light source (such as a light emitting diode or vertical cavity surface emitting laser (VCSEL)) emits a light, which is detected by the optical detector. The amount of light detected by the optical detector is indicative of the physiological condition detected. A front end (such as a CMOS front end) can receive a signal from the detector, which can alter the impedance presented to the ultrasonic transducer. In some embodiments, a digital circuit receives the signal from the front end circuit and operates a modulation circuit, which modulates the impedance presented to the ultrasonic transducer. The ultrasonic backscatter transmitted from the miniaturized ultrasonic transducer to the interrogator thus encodes information from the detected physiological condition.

The light source can be disposed outside of the tissue, implanted within the tissue, or as part of the implantable device itself (which may be controlled by a driver on the ASIC). In some embodiments, the light source emits light in the near infrared range (e.g., a wavelength of about 780 nm to about 2500 nm). In some embodiments, a plurality of light sources are include, which may emit light at different wavelengths. In some embodiments the implantable device is used for near-infrared spectroscopy, which can be used to detect certain analytes in blood or interstitial tissue, such as glucose. In some embodiments, the light source emits light outside of the infrared range (such as at a wavelength below about 780 nm or above about 2500 nm). Since there is a distance limit when transmitting light through tissue (generally less than about 2 cm), it is generally preferable to include the light source on the implantable device when using the implantable device at depths greater than about 2 cm. In some embodiments, the implantable device is implanted at a depth of about 2 cm or more (such as about 3 cm or more, about 4 cm or more, or about 5 cm or more).

Figure 9A:
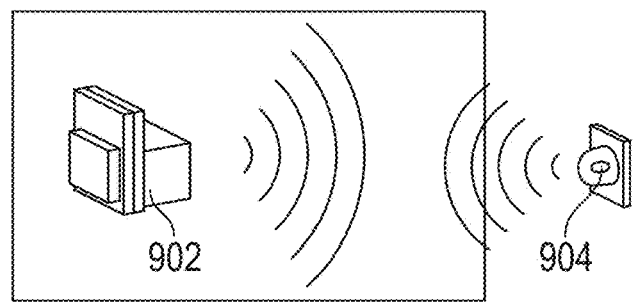
FIG. 9A illustrates backscatter communication of the implantable device sensor to an external transceiver based on intensity modulation of light in tissue from an optical emitter. The sensor on the implantable device can be an optical filter-enhanced sensor.

FIG. 9A illustrates an implantable device 902 implanted in tissue detecting light and emitting ultrasonic backscatter waves. The implantable device 902 further receives ultrasonic waves from an external ultrasonic transducer (not shown). The implantable device receives light from an external light source 904. Changes in the amount of light detected by the implantable device due to changes in a physiological condition modulate the ultrasonic backscatter. FIG. 9A illustrates a system comprising an implantable device comprising an optical detector implanted in tissue in optical communication with an external light source. In the simplest form, the implantable device can be embedded in the tissue with an external optical emitter (visible light, NIR, near ultraviolet or otherwise) for optical sensing. The external optical emitter can be coupled with an external transceiver, or may be a separate component. The embodiment illustrated in FIG. 9A demonstrates the utilization of an optical filter to ensure detection of the intensity of only a single wavelength or multiple selected wavelengths. This optical emitter may be a monochromatic light source or a broadband light source. Furthermore, the optical emitter can be implanted in the body. The emitter may be on-board or independently implanted. Power transmission, local temperature elevation and implant size would have to be considered when implanting the optical emitter in the patient.

Figure 9B:
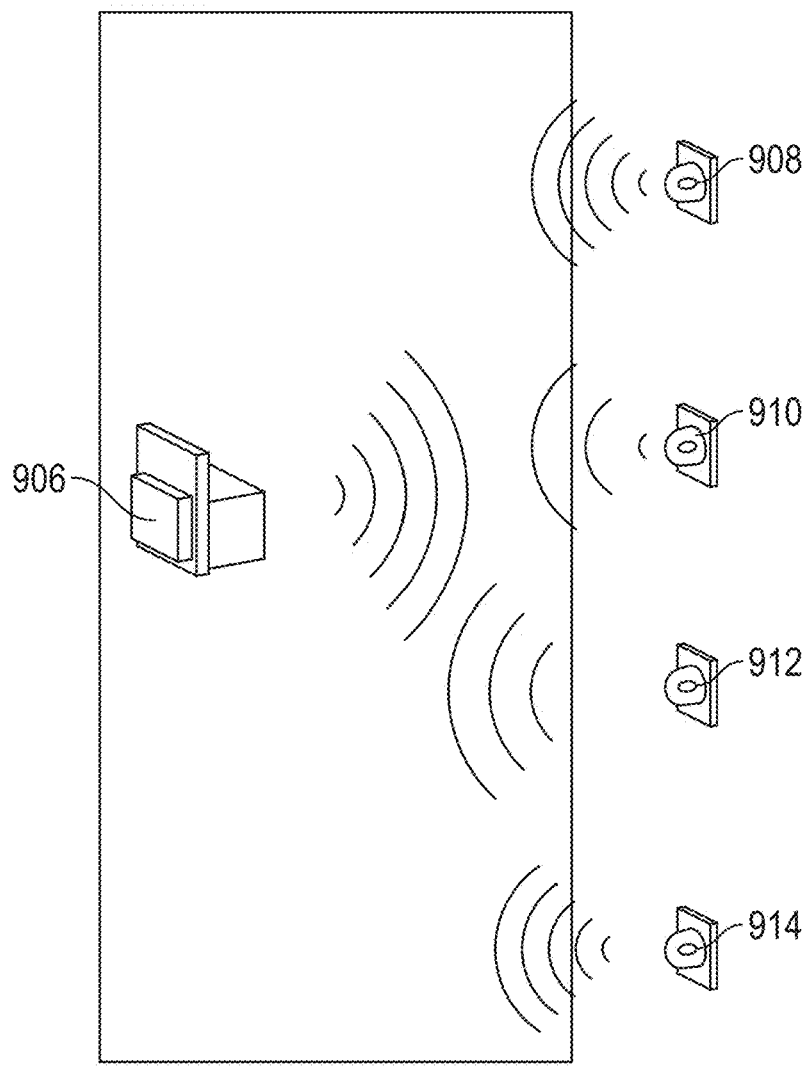
FIG. 9B illustrates alternate pulsing of monochromatic light using an array of elements emitting light of varying wavelengths right) for the implementation of NIR multiple wavelength spectrophotometry using an optical sensor.

In some embodiments, the light source emits broadband light. In some embodiments, the light source emits narrowband light. For example, the light source can include an optical filter, and can emit narrowband light at one or more predetermined wavelengths. In some embodiments, the light source emits narrowband light at one or more, two or more, three or more, or four of more different wavelengths. In some embodiments, the light source emits narrowband light a plurality of different wavelengths, wherein at least one narrowband light wavelength is used for error correction. It has been demonstrated that by alternately pulsing monochromatic light of three wavelengths in the NIR spectral region and utilizing NIR light of a fourth wavelength for error correct, tissue oxygenation levels can be monitored due to the absorptive behavior of hemoglobin, myoglobin, and cytochrome aa3. This is shown in FIG. 9B. In FIG. 9B, an implantable device 906 is implanted in tissue and receives narrow band light from four different light sources (light source 908, light source 910, light source 912, and light source 914), wherein each light source emits a different narrowband light wavelength. As illustrated, light source 908, light source 910, light source 912, and light source 914 are positioned external to the tissue. The implantable device 906 further receives ultrasonic waves from an external ultrasonic transducer (not shown). Changes in the amount of light detected by the implantable device due to changes in a physiological condition modulate the ultrasonic backscatter.

Analyte measurements may also be conducted through means other than NIR spectroscopy. One such example is through the use of optodes for chemical sensing.

Scattering should be considered and taken into account when using light outside of the NIR spectral region.

Figure 9C:
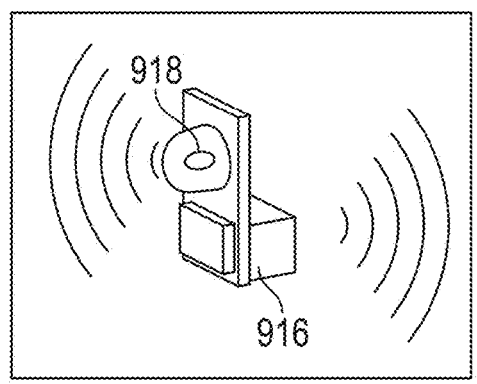
FIG. 9C illustrates an implantable device having an optical sensor, including a light source and an optical detector. The sensor includes an integrated optical emitter.

FIG. 9C illustrates an implantable device 916 comprising the light source 918. The implantable device further includes a light detector (not shown), which can receive light from the light source 918. The implantable device 906 further receives ultrasonic waves from an external ultrasonic transducer (not shown), which can power the implantable device 916, including the light source 918. Changes in the amount of light detected by the implantable device due to changes in a physiological condition modulate the ultrasonic backscatter.

Implantable devices with optical sensors can be useful for a variety of purposes. For example, the implantable device can be used to monitor oxygen levels (including blood oxygen levels or interstitial fluid oxygen levels) in a subject, tumor oxygenation monitoring, functional brain imaging, blood analyte measurements, tissue engineering (such as to monitor for anoxia and hypoxia), and pH measurements. In some embodiments, the optical sensor is used for determining a blood pressure or a pulse rate.

In some embodiments, the sensor on the implantable device is an oxygen sensor or a pH sensor. An implantable device comprising an oxygen sensor or pH sensor can be useful for monitoring physiological oxygen concentration (such as blood oxygen or interstitial fluid oxygen) or physiological pH (such blood pH or interstitial fluid pH). The oxygen concentration or pH can be localized to the vicinity of the implantable device, or, if a network of devices is used, the measured oxygen concentration or pH can by a systemic physiological measurement. This can be useful, for example, in monitoring hypoxia or acidemia. The implantable device can include a miniaturized ultrasonic transducer (such as a bulk piezoelectric transducer, a PMUT, or a CMUT), an ASIC (which may include a driver and a front end), and an oxygen or pH sensor.

In some embodiments, an oxygen sensor comprises a Clark electrode. A Clark electrode measures oxygen on a catalytic surface (such as a platinum surface) surrounded by a membrane, and can be miniaturized to be included on an implantable device. The Clark electrode can be attached to the ASIC on the implantable device, and variance in the amount of oxygen sensed by the implantable device (which may be blood oxygen or interstitial fluid oxygen) can modulate the ultrasonic backscatter.

In some embodiments, the oxygen sensor includes a light source (such as a light emitting diode or vertical cavity surface emitting laser (VCSEL)) and an optical detector (such as a phototransistor or a photovoltaic cell, or an array of phototransistors or photovoltaic cells). A matrix including an oxygen-sensitive fluorophore or a pH-sensitive fluorophore is disposed over the light source and the light detector, or in a position bridging the light source and the light detector, and the amount of light detected by the light source depends on the amount of oxygen in or the pH of the surrounding fluid. Such devices can be referred to as optrodes. The matrix can include, for example, an oxygen-sensitive fluorophore (such as a ruthenium fluorophore) or pH-sensitive fluorophore in a polymer, and increased oxygen or increased or decreased pH (depending on the choice of fluorophore) can cause a faster decay of fluorescence and a decrease in intensity. This oxygen- or pH-dependent change in intensity and fluorescence decay lifetime can be detected by the optical detector. In some embodiments, the matrix is a hydrogel or polydimethylsiloxane (PDMS) polymer containing a ruthenium fluorophore. In some embodiments the ruthenium fluorophore is bound to silica particles or silica surfaces contained within the matrix (these can be made by sol-gel processes, for example). The matrix protects the fluorophore from components in the extracellular fluid and inhibits adhesion of proteins, cells and other cellular debris that could affect the diffusion of oxygen into the matrix. Further, encapsulation of the ruthenium metal in the matrix reduces potential toxicity of the ruthenium. The light source and/or optical detector can optionally include a filter to limit emitted or detected light to a narrow bandwidth. The ASIC can drive the light source to emit a pulsed or sinusoidal light signal, which causes the light source to emit the light. The light emitted by the light source causes the fluorophore in the matrix to fluoresce. For example, in some embodiments the light source emits a blue light or a UV light, and the fluorophore can emit an orange or red light. The fluorescence intensity and/or lifetime (decay) of fluorescence is a function of the oxygen concentration or pH of the matrix, which is influenced by the surrounding fluid (e.g., blood or interstitial fluid). From the fluorescence decay, a fluorescent lifetime decay constant can be determined, which can reflects the oxygen amount or pH.

Figure 10A:
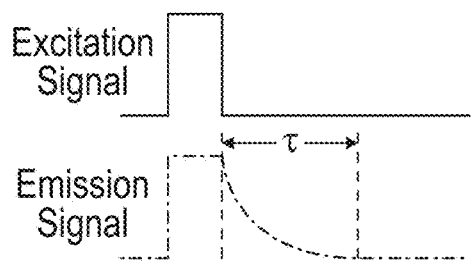
FIG. 10A illustrates a pulse of light emitted by a light source and the resulting fluorescent decay detected by an optical detector after the light excites a fluorophore in a matrix in an optical sensor.

Use of a light pulse emitted from the light source allows for the observation of fluoresce decay or fluorescence lifetime, which is dependent on pH or oxygen concentration. This is shown in FIG. 10A. Thus, in some embodiments, the decay of fluorescence (the fluorescence lifetime) following a light pulse from the light source is used to measure the oxygen concentration or the pH surrounding the sensor.

Figure 10B:
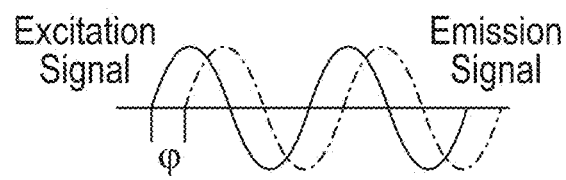
FIG. 10B illustrates the phase shift between an oscillating light emitted by a light source and the resulting fluorescent lifetime detected by an optical detector after the light excites a fluorophore in a matrix in an optical sensor.
Figure 10C:
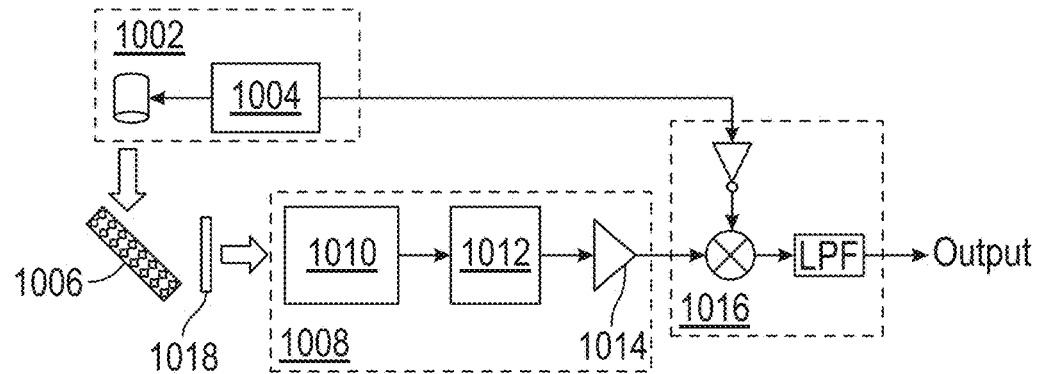
FIG. 10C illustrates a schematic of an exemplary optical sensor for detecting the phase shift shown in FIG. 10B.

Use of an oscillating light source allows for the fluorescence emission to be offset from the light source due to the decay of fluorescence (fluorescence lifetime). The phase shift between the light source wave and the fluorescence detection is dependent on the concentration of oxygen or pH. This is shown in FIG. 10B. The phase shift $\varphi$ can be determined as follows:

$$\tan \varphi = (2\pi f) \times \tau$$

wherein f is the oscillation frequency of the light emitted from the light source, and $\tau$ is the lifetime of the fluorescence decay (which depends on the oxygen or pH concentration). Thus, in some embodiments an oscillating light source is used, and the phase shift of the light source relative to the fluorescence is used to determine pH or oxygen concentration surrounding the sensor. An exemplary optical detector that can be used to measure a phase shift is shown in FIG. 10C. The light source 1002 includes an oscillator 1004, and emits light toward a matrix 1006. The matrix 1006 includes an oxygen-sensitive or pH-sensitive fluorophore, which is detected by the optical detector 1008. The optical detector 1008 includes a photodiode (or a photodiode array) 1010, which transmits current to a current to voltage conversion module (such as a transimpedance amplifier (TIA) or voltage buffer) 1012. The optical detector 1008 may further include an amplifier 1014. A phase detector 1016 is included, which can determine the phase difference between the oscillating light emitted by the light source 1002 and the light detected by the optical detector 1008. An optional optical filter (such as a long pass filter) 1018 can be included between the matrix 1006 and the optical detector 1008. In some embodiments, a light sourced can be pulsed and the fluorescence lifetime can be measured by sampling the fluorescence upon extinguishing the light source (i.e. from the falling edge of the pulse).

The optical detector detects the light emitted by the fluorophore, which is read by the ASIC. In some embodiments, the ASIC modulates current to the miniaturized ultrasonic transducer as a function of the raw signal (or some portion of the raw signal) from the optical detector, and the miniaturized ultrasonic transducer can emit backscatter ultrasonic waves reflecting the detected signal. In some embodiments, the ASIC modulates the impedance presented to the transducers as a digital representation of the raw or compressed signal. In some embodiments, the ASIC itself calculates the oxygen concentration or pH, and sends a signal to the miniaturized ultrasonic transducer encoding the signal. In some embodiments, the external ultrasonic transceiver pulses ultrasonic waves, which causes pulses of current through the implantable device (and, in turn, pulses of light). Between the pulses of current, the miniaturized ultrasonic transducer emits the ultrasonic backscatter echo.

Figure 11A:
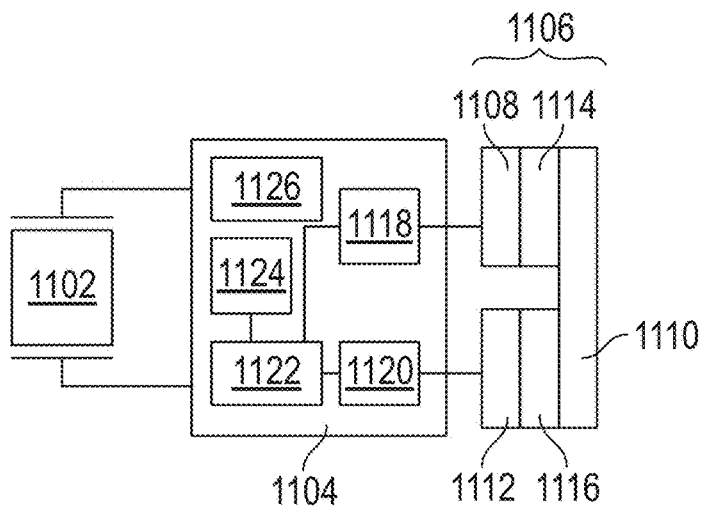
FIG. 11A illustrates a schematic of one embodiment of an implantable device with a miniaturized ultrasonic transducer, an integrated circuit, and an optical sensor.
Figure 11B:
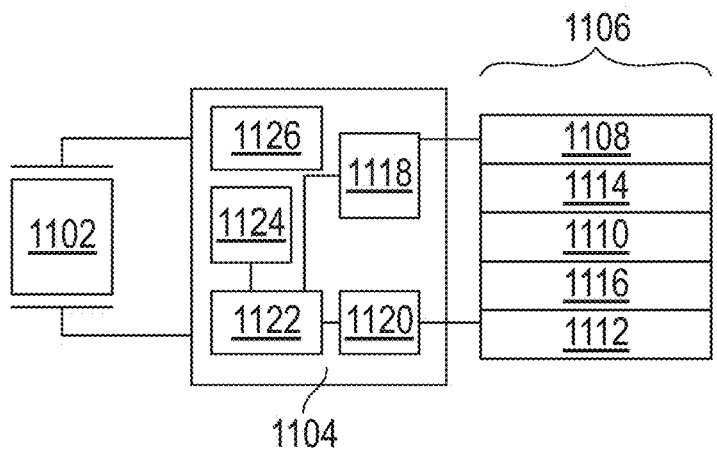
FIG. 11B illustrates another schematic of one embodiment of an implantable device with a miniaturized ultrasonic transducer, an integrated circuit, and an optical sensor.

FIG. 11A illustrates one embodiment of an implantable device with an oxygen sensor or pH sensor. The implantable device includes a miniaturized ultrasonic transducer 1102, an ASIC 1104, and a pH or oxygen sensor 1106. The sensor 1106 includes a light source (such as a light emitting diode) 1108, a pH-sensitive or oxygen-sensitive matrix 1110, and an optical detector 1112 (such as a photovoltaic, a phototransistor, or any other suitable optical detector known in the art). The matrix 1110 includes an oxygen sensitive fluorophore (for an oxygen sensor) or a pH sensitive fluorophore (for a pH sensor). Optionally, a filter 1114 is disposed between the light source 1108 and the matrix 1110. The filter can be configured to allow a narrowband light to be transmitted to the matrix 1110. In some embodiments, in addition to or in place of filter 1114, a filter 1116 is disposed between the matrix 1110 and the optical detector 1112. The filter 1116 can be configured to allow a narrowband light to enter the optical detector 1112. The light source 1108 is powered by a driver 1118, and the optical detector 1112 transmits a signal received by a front end (such as a CMOS front end) 1120. The front end 1120 and the driver 1118 are connected to a digital circuit 1122, which controls a modulation circuit 1124 (the digital circuit can include appropriate conversion circuitry to properly measure and sample the detector signal) The modulation circuit controls the impedance presented to the miniaturized ultrasonic transducer 1102, which emits backscatter waves to an interrogator. The ASIC 1104 can also include a power circuit 1126, which provides power to components of the ASIC; the power circuit derives power from the transducer. In the embodiment shown in FIG. 11A, the light source 1108 and the optical detector 1112 are directed in the same direction. FIG. 11B illustrates an alternative configuration of the implantable device with an oxygen sensor or a pH sensor, with the light source 1108 and the optical detector 1112 are directed toward each other.

In some embodiments, the optical sensor is used to determine blood pressure or a pulse rate. For example, the optical sensor can include a membrane. Light from the light source is focused on the membrane, and the membrane reflects the light, which is detected by the optical detector. The membrane is deformed by pressure, and the deformations are cause variation in the reflected light.

In some embodiments, an implantable device with a temperature sensor includes a miniaturized ultrasonic transducer (such as a bulk piezoelectric transducer, a PMUT, or a CMUT) and a temperature sensor (such as a proportional to absolute temperature (PTAT) circuit, a thermocouple, or a thermistor). In some embodiments, the thermistor is a negative temperature coefficient (NTC) thermistor. In some embodiments, the thermistor is a positive temperature coefficient (NTC) thermistor. In some embodiments, the implantable device further comprises an ASIC (which optionally includes a front end, such as a CMOS front end, or a driver), which may be integrated with or distinguishable from the temperature sensor. In some embodiments, the ASIC includes a digital circuit, a modulation circuit, or a power circuit; the power circuit derives power from the transducer. In some embodiments, the implantable device does not include an ASIC. The impedance presented to the transducer by the temperature sensor depends on the measured temperature, which modulates the current flowing through the ultrasonic transducer. As the current flowing through the ultrasonic transducer produces changes in ultrasonic backscatter detected by the external transceiver, temperature can be measured using the implantable device comprising the temperature sensor. The implantable device comprising a temperature sensor can be used, for example, to monitor temperature of an organ (such as the liver, stomach, small or large intestine, kidney, pancreas, gallbladder, bladder, ovaries, uterus, spleen, etc.) in a subject, for example during ablation (e.g., radiofrequency ablation, microwave thermotherapy ablation, or cryotherapy ablation) of tissue, such as a cancer. In some embodiments, the organ is a transplanted organ. In some embodiments, the implantable device comprising a temperature sensor is used to monitor the temperature of a site of infection. In some embodiments, the implantable device with a temperature sensor is able to resolve a temperature within about 2° C. or less (such as within about 1° C. or less, or within about 0.5° C. or less).

Figure 12A:
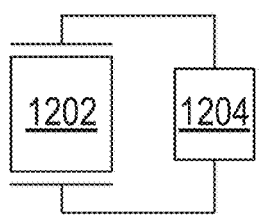
FIG. 12A illustrates a schematic of one embodiment of an implantable device with a miniaturized ultrasonic transducer and a temperature sensor.

FIG. 12A illustrates one embodiment of an implantable device with a miniaturized ultrasonic transducer 1202 (such as a bulk piezoelectric transducer, a PMUT, or a CMUT) and a temperature sensor 1204 (such as a PTAT circuit or a thermistor). Ultrasonic waves transmitted by an interrogator vibrate the miniaturized ultrasonic transducer 1202, which generates a current that passes through the temperature sensor 1204. The temperature sensor 1204 generates a resistance depending on the temperature of the sensor 1204, which modulates the current flowing through the miniaturized ultrasonic transducer 1202. The ultrasonic backscatter transmitted by the miniaturized ultrasonic transducer 1202 to the interrogator depends on the sensor impedance and the resultant change in transducer current. Thus, the ultrasonic backscatter depends on the temperature of the temperature sensor 1204, which can be used to determine the temperature of the surrounding tissue.

Figure 12B:
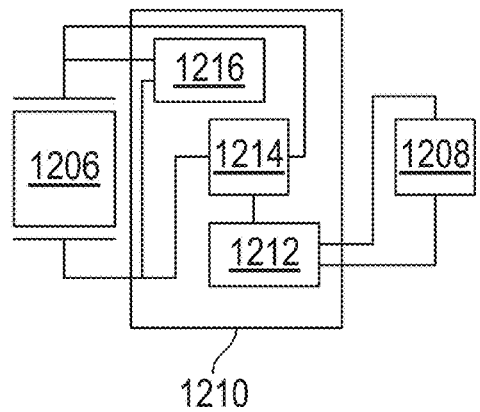
FIG. 12B illustrates a schematic of one embodiment of an implantable device with a miniaturized ultrasonic transducer, an integrated circuit, and a temperature sensor.

FIG. 12B illustrates an embodiment of an implantable device with a miniaturized ultrasonic transducer 1206 (such as a bulk piezoelectric transducer, a PMUT, or a CMUT), a temperature sensor 1208 (such as a PTAT circuit or a thermistor), and an ASIC 1210. The ASIC 1210 can include a digital circuit 1212, which can operate and receive signals from the temperature sensor 1208. The digital circuit 1212 can also convert an analog signal from the temperature sensor 1208 into a digital signal. The digital circuit 1212 operates a modulation circuit 1214 (such as a switch, for example a FET), which is connected to the miniaturized ultrasonic transducer 1206. The digital circuit 1212 can transmit a signal to the modulation circuit 1214 a digital signal or an analog signal, and the modulation circuit 1214 alters the impedance of current flowing to the miniaturized ultrasonic transducer 1206. In some embodiments, the digital circuit 1212 computes the temperature detected by the temperature sensor 1208, which is encoded on the signal transmitted to the modulation circuit 1214. In some embodiments, the digital circuit 1212 transmits the raw signal from the temperature sensor 1208 to the modulation circuit 1214. The miniaturized f ultrasonic transducer 1206 emits a backscatter ultrasonic wave, which encodes the temperature information. The ASIC 1210 can also include a power circuit 1216, which can provide power to components of the ASIC; the power circuit derives power from the transducer. Optionally, the ASIC can include a driver and/or a front end (such as a CMOS front end), which can be used to control and collect signals from the temperature sensor 1208.

In some embodiments, the sensor is a pressure sensor. An implantable device comprising a pressure sensor can be used, for example, for monitoring blood pressure, pulse rate, tissue inflammation, vascular constriction, compartment syndrome, gastrointestinal (GI) tract monitoring, wound recovery, intra-ocular pressure, or cranial pressure. The implantable device can include a miniaturized ultrasonic transducer (such as a bulk piezoelectric transducer, a PMUT, or a CMUT) and a pressure sensor. In some embodiments, the implantable device further comprises an ASIC (which optionally includes a front end, such as a CMOS front end, or a driver), which may be integrated with or distinguishable from the pressure sensor. In some embodiments, the ASIC includes a digital circuit, a modulation circuit, or a power circuit. In some embodiments, the implantable device does not include an ASIC. The pressure sensor can be, for example, a microelectromechanical system (MEMS), which can modulate current (which may pass through the ASIC, if present) in response to applied pressure.

Figure 13A:
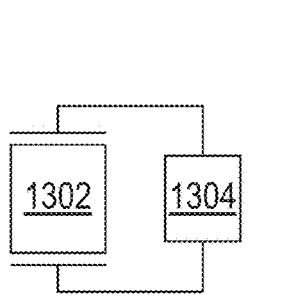
FIG. 13A illustrates a schematic of one embodiment of an implantable device with a miniaturized ultrasonic transducer and a pressure sensor.

FIG. 13A illustrates one embodiment of an implantable device with a miniaturized ultrasonic transducer 1302 (such as a bulk piezoelectric transducer, a PMUT, or a CMUT) and a pressure sensor 1304 (such as a MEMS). Ultrasonic waves transmitted by an interrogator vibrate the miniaturized ultrasonic transducer 1302, which generates a current that passes through the pressure sensor 1304. The pressure sensor 1304 exhibits a pressure-dependent impedance 1304, which modulates the current returning to the miniaturized ultrasonic transducer 1302. The ultrasonic backscatter transmitted by the miniaturized ultrasonic transducer 1302 to the interrogator depends on the returning current. Thus, the ultrasonic backscatter depends on the pressure sensed by the pressure sensor 1304, which can be used to determine the pressure of the surrounding tissue.

Figure 13B:
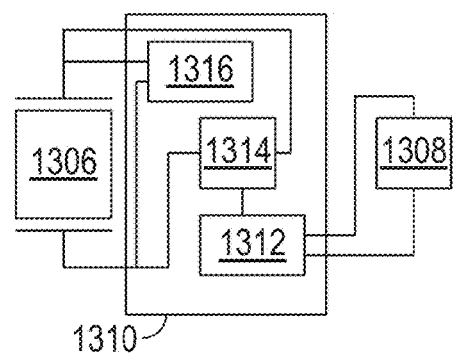
FIG. 13B illustrates a schematic of one embodiment of an implantable device with a miniaturized ultrasonic transducer, an integrated circuit, and a pressure sensor.

FIG. 13B illustrates an embodiment of an implantable device with a miniaturized ultrasonic transducer 1306 (such as a bulk piezoelectric transducer, a PMUT, or a CMUT), a pressure sensor 1308 (such as a MEMS), and an ASIC 1310. The ASIC 1310 can include a digital circuit 1312, which can operate and receive signals from the pressure sensor 1308. The digital circuit 1312 can also convert an analog signal from the pressure sensor 1308 into a digital signal. The digital circuit 1312 operates a modulation circuit 1314 (such as a switch, for example a FET), which is connected to the miniaturized ultrasonic transducer 1306. The digital circuit 1312 can transmit a signal to the modulation circuit 1314 a digital signal or an analog signal, and the modulation circuit 1314 alters the impedance presented to the miniaturized ultrasonic transducer 1306. In some embodiments, the digital circuit 1312 computes the pressure detected by the pressure sensor 1308, which is encoded on the signal transmitted to the modulation circuit 1314. In some embodiments, the digital circuit 1312 transmits the raw signal from the pressure sensor 1208 to the modulation circuit 1314. The miniaturized ultrasonic transducer 1306 emits a backscatter ultrasonic wave, which encodes the pressure information. The ASIC 1310 can also include a power circuit 1316, which can provide power to components of the ASIC; the power circuit derives power from the transducer. Optionally, the ASIC can include a driver and/or a front end (such as a CMOS front end), which can be used to control and collect signals from the pressure sensor 1308.

In some embodiments, the sensor is a glucose sensor. Diabetes is a group of metabolic diseases in which the blood sugar levels are elevated for long periods of time, resulting in dehydration, cardiovascular damage, nerve damage, and more. Currently there is no cure for diabetes, and those who suffer from the disease must constantly monitor their blood glucose levels, as careful regulation of glucose conditions can control diabetic complications. Conventional glucose monitoring is performed by patients using a lancet to draw blood and running the blood sample through a glucose monitor. This is un-pleasant for patients and purchasing lancets and test strips can become quite costly, since diabetic patients must monitor their glucose levels six to seven times a day. Alternate methods of glucose monitoring attempt to address the issue of repeated needle insertion by creating continuous glucose monitors, but these are either more expensive and still require needle insertion, or are non-invasive but less accurate. Here, the described implantable devices can play a role in continuous glucose monitoring; a chronically implanted device in which the backscatter is modulated by glucose oxidation, could allow for continuous glucose monitoring just by patching an interrogator with conductive gel over the body.

Electrochemical glucose monitoring has been long implemented with amperometric measurements using electrodes coated with enzymes such as glucose oxidase to ensure specificity. Unfortunately, such devices tend to have low device lifetimes. Commercially purchased subcutaneous continuous glucose monitors often only have 3-7 day lifetimes due to the instability of the enzyme layer at body temperatures. To counteract this, non-enzymatic probes have been developed, such as potentiometric chemical sensors. Unfortunately, one of the leading causes for failure of these devices is simply the introduction of foreign bodies into subcutaneous tissue. The issue of foreign body response is similar to the challenge faced in chronic neural interface implantation. The implantable devices described herein, such as implantable devices coated in SiC, provide a powerful solution.

In some embodiments, the implantable device comprises a miniaturized ultrasonic transducer (such as a bulk piezoelectric transducer, a PMUT, or a CMUT), an ASIC, and a glucose sensor. The glucose sensor can detect glucose in blood or interstitial fluid, and the current flowing from the sensor can depend on the concentration of glucose detected by the sensor. Backscatter ultrasonic waves emitted by the miniaturized ultrasonic transducer can encode glucose concentration information. For example, the glucose sensor can have a first electrode and a second electrode, and a voltage differential can be generated based on the amount of glucose in the sensor. In some embodiments, the first electrode is functionalized by glucose oxidase. In some embodiments, the sensor includes a glucose-permeable membrane separating the electrodes from the surrounding tissue. In some embodiments, the ASIC includes a front end (such as a CMOS front end) or a driver. In some embodiments, the ASIC includes a digital circuit, a modulation circuit, or a power circuit. The ASIC can operate the glucose sensor to receive a signal dependent on the concentration of glucose in the sensor. For example, cyclic voltammetry can be used to generate a voltage dependent on the concentration of glucose, which is reflected in a signal received by the AISC. In some embodiments, the digital circuit operates the glucose sensor. The signal from the glucose sensor is sent to a modulation circuit (such as a switch, for example a FET), would modulates the impedance presented to the miniaturized ultrasonic transducer. In some embodiments, the digital circuit controls the modulation circuit. In some embodiments, the digital circuit can transmits a raw signal to the modulation circuit. In some embodiments, the digital circuit determines the glucose concentration from the raw signal received from the glucose sensor, and sends a signal to the modulation circuit encoding the determined glucose concentration.

In some embodiments, the sensor is a strain sensor (or strain gauge). The strain sensor measures how much a material (such as a tissue or organ) stretches in proportion to a baseline length. A strain sensor can include, for example, a thin film conductor or semiconductor that changes resistance as it stretches.

Manufacture of an Implantable Device

The implantable devices can be manufactured by attaching a miniaturized ultrasonic transducer (such as a CMUT, a PMUT, or a bulk piezoelectric transducer) to a first electrode on a first face of the piezoelectric transducer, and a second electrode to a second face of the piezoelectric transducer, wherein the first face and the second face are on opposite sides of the piezoelectric transducer. The first electrode and the second electrode can be attached to an application-specific integrated circuit (ASIC), which may be disposed on a printed circuit board (PCB). Attachment of the components to the PCB can include wirebonding, soldering, flip-chip bonding, or gold bump bonding. The ASIC can include one or more sensors.

Certain piezoelectric materials can be commercially obtained, such as metalized PZT sheets of varying thickness (for example, PSI-5A4E, Piezo Systems, Woburn, Mass., or PZT 841, APC Internationals, Mackeyville, Pa.). In some embodiments, a piezoelectric material sheet is diced into a desired size, and the diced piezoelectric material is attached to the electrodes. In some embodiments, the electrodes are attached to the piezoelectric material sheet, and the piezoelectric material sheet is diced to the desired size with the electrodes attached to the piezoelectric material. The piezoelectric material can be diced using a dicing saw with a ceramic blade to cut sheets of the piezoelectric material into individualized piezoelectric transducer. In some embodiments, a laser cutter is used to dice or singulate the piezoelectric material. In some embodiments, patterned etching is used to dice or singulate the piezoelectric material.

Electrodes can be attached to the top and bottom of the faces of the piezoelectric transducers, with the distance between the electrodes being defined as the height of the piezoelectric transducer. Exemplary electrodes can comprise one or more of silver, gold, platinum, platinum-black, poly (3,4-ethylenedioxythiophene (PEDOT), a conductive polymer (such as conductive PDMS or polyimide), or nickel. In some embodiments, the electrode is attached to the piezoelectric transducer by electroplating or vacuum depositing the electrode material onto the face of the piezoelectric transducer. In some embodiments, the electrodes are soldered onto the piezoelectric transducer using an appropriate solder and flux. In some embodiments, the electrodes are attached to the piezoelectric transducer using an epoxy (such as a silver epoxy) or low-temperature soldering (such as by use of a solder paste).

In an exemplary embodiment, solder paste is applied to a pad on a printed circuit board (PCB), either before or after the ASIC is attached to the PCB. The size of the pad on the circuit board can depend on the desired size of the piezoelectric transducer. Solely by way of example, if the desired size of piezoelectric transducer is about 100 μm×100 μm×100 μm, the pad can be about 100 μm×100 μm. The pad functions as the first electrode for the implantable device. A piezoelectric material (which may be larger than the pad) is placed on the pad, and is held to the pad by the applied solder paste, resulting in a piezoelectric-PCB assembly. The piezoelectric-PCB assembly is heated to cure the solder paste, thereby bonding the piezoelectric transducer to the PCB. If the piezoelectric material is larger than the pad, the piezoelectric material is cut to the desired size, for example using a wafer dicing saw or a laser cutter. Non-bonded portions of the piezoelectric material (for example, the portions of the piezoelectric material that did not overlay the pad) are removed. A second electrode is attached to the piezoelectric transducer and the PCB, for example by forming a wirebond between the top of the piezoelectric transducer and the PCB, which completes the circuit. The wirebond is made using a wire made from any conductive material, such as aluminum, copper, silver, or gold.

The integrated circuit and the miniaturized ultrasonic transducer can be attached on the same side of the PCB or on opposite sides of the PCB. In some embodiments, the PCB is a flexible PCB, the integrated circuit and the ultrasonic transducer are attached to the same side of the PCB, and the PCB is folded, resulting in an implantable device in which the integrated circuit and the ultrasonic transducer are on opposite sides of the PCB.

Optionally, the device or a portion of the device is encapsulated in a biocompatible material (such as a biocompatible polymer), for example a copolymer of N-vinyl-2-pyrrolidinone (NVP) and n-butylmethacrylate (BMA), polydimethylsiloxane (PDMS, e.g., Sylgard 184, Dow Corning, Midland, Mich.), parylene, polyimide, silicon nitride, silicon dioxide, alumina, niobium, hydroxyapatite, or silicon carbide. The silicon carbide can be amorphous silicon carbide or crystalline silicon carbide. In some embodiments, the biocompatible material (such as amorphous silicon carbide) is applied to the device by plasma enhanced chemical vapor deposition (PECVD) or sputtering. PECVD may use precursors such as $SiH_4$ and $CH_4$ to generate the silicon carbide. In some embodiments, the implantable device or portion of the implantable device is encased in a ceramic (for example, alumina or titania) or a metal (for example, steel or titanium) suitable for medical implantation.

Figure 14:
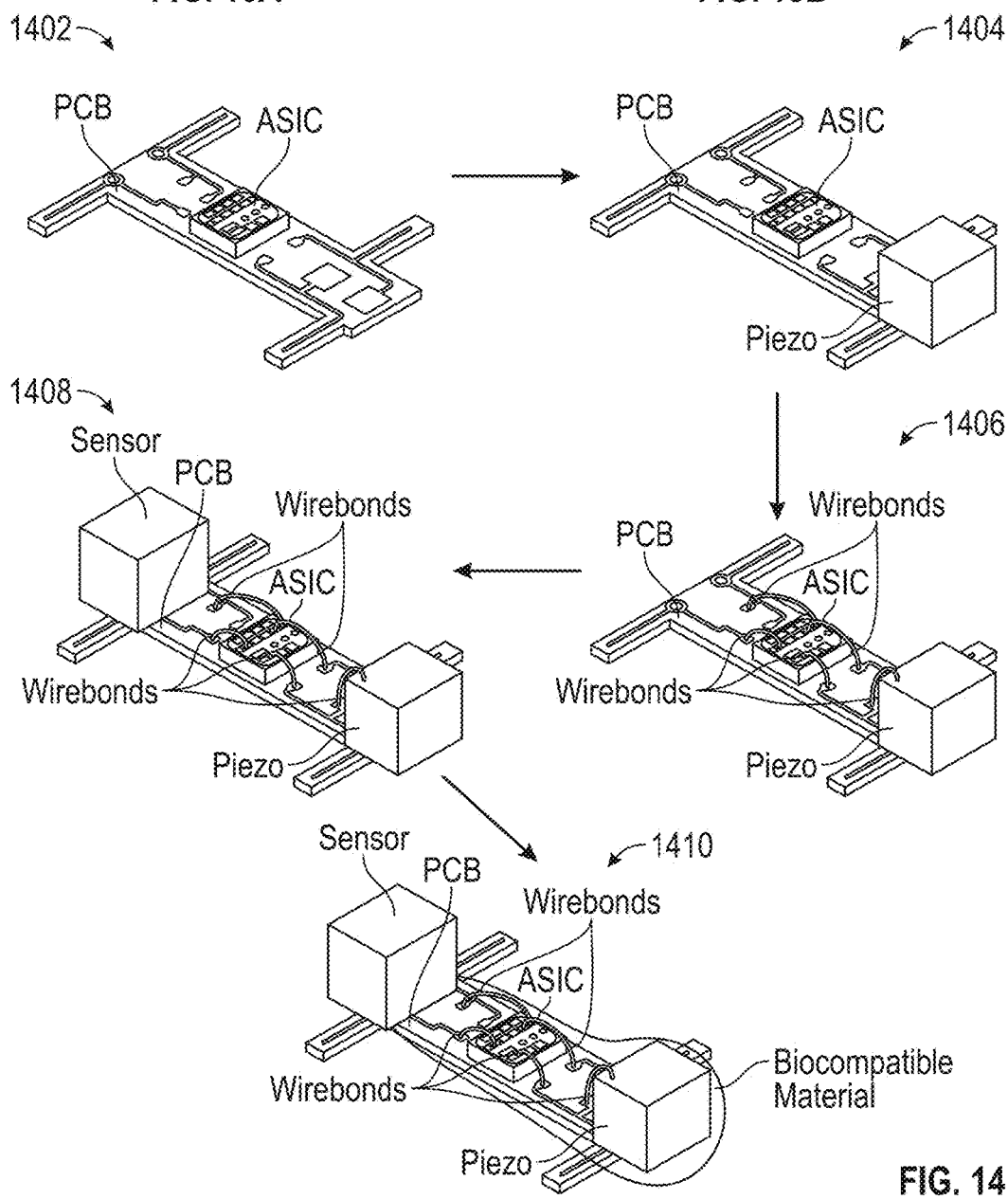
FIG. 14 illustrates a method of manufacturing an implantable device described herein.

FIG. 14 illustrates an exemplary method of producing the implantable device described herein. At step 1402, an ASIC is attached to a PCB. A solder (such as a silver epoxy) can be applied to the PCB (for example, at a first pad disposed on the PCB), and the ASIC can be placed on the solder. The solder can be cured, for example by heating the PCB with the ASIC. In some embodiments, the PCB with the ASIC is heated to about 50° C. to about 200° C., such as about 80° C. to about 170° C., or about 150° C. In some embodiments, the PCB with the ASIC is heated for about 5 minutes to about 600 minutes, such as about 10 minutes to about 300 minutes, about 10 minutes to about 100 minutes, about 10 minutes to about 60 minutes, about 10 minutes to about 30 minutes, or about 15 minutes. Optionally, the ASIC is coated with additional solder. At step 1404, a piezoelectric transducer (the "piezo" in FIG. 14) is attached to the PCB. A solder (such as a silver epoxy) can be applied to the PCB (for example, at a second pad disposed on the PCB), and a piezoelectric material can be placed on the solder. The piezoelectric material can be a fully formed (i.e., "diced") piezoelectric transducer, or can be a piezoelectric material sheet that is cut to form the piezoelectric transducer once attached to the PCB. The solder can be cured, for example by heating the PCB with the piezoelectric material. In some embodiments, the PCB with the piezoelectric material is heated to about 50° C. to about 200° C., such as about 80° C. to about 170° C., or about 150° C. In some embodiments, the PCB with the piezoelectric material is heated for about 5 minutes to about 600 minutes, such as about 10 minutes to about 300 minutes, about 10 minutes to about 100 minutes, about 10 minutes to about 60 minutes, about 10 minutes to about 30 minutes, or about 15 minutes. The piezoelectric material can be cut using a saw or laser cutter to the desired dimensions. In some embodiments, the piezoelectric material is a solgel (such as a PZT solgel) and the transducer material can be shaped with deep reactive ion etching (DRIE). Although FIG. 14 illustrates attachment of the ASIC to the PCB at step 1402 prior to attachment of the piezoelectric material to the PCB at step 1404, a person of skill in the art will appreciate that the ASIC and the piezoelectric material can be attached in any order. At step 1406, the ASIC and the piezoelectric transducer are wirebonded to the PCB. Although the method illustrated in FIG. 14 shows the ASIC and the piezoelectric transducer to the PCB after the ASIC and the piezoelectric transducer are attached to the PCB, a person of skill in the art will appreciate that the ASIC can be wirebonded to the PCB after the ASIC is attached to the PCB, and can be wirebonded either before or after attachment of the piezoelectric transducer. Similarly, the piezoelectric transducer may be wirebonded to the PCB either before or after attachment or wirebonding of the ASIC to the PCB. At step 1408, a sensor is attached to the PCB. The sensor can be any sensor described herein. A solder (such as a silver epoxy) can be applied to the PCB (for example, at a third pad disposed on the PCB), and the sensor can be placed on the solder. The solder can be cured, for example by heating the PCB with the sensor. In some embodiments, the PCB with the sensor is heated to about 50° C. to about 200° C., such as about 80° C. to about 170° C., or about 150° C. In some embodiments, the PCB with the sensor is heated for about 5 minutes to about 600 minutes, such as about 10 minutes to about 300 minutes, about 10 minutes to about 100 minutes, about 10 minutes to about 60 minutes, about 10 minutes to about 30 minutes, or about 15 minutes. Although FIG. 14 illustrates the sensor being attached the PCB after the piezoelectric transducer and the ASIC are attached to the PCB, a person of skill in the art would understand that the sensor can be attached to the PCB either before or after the ASIC and the piezoelectric transducer are attached to the PCB. Depending on the sensor type, the sensor may be wirebonded to the PCB, which may occur after the sensor is attached to the PCB, and either before or after wirebonding of the piezoelectric transducer and/or ASIC to the PCB. At step 1410, at least a portion of the device is coated with a biocompatible material. Preferably, at least the piezoelectric transducer and the ASIC are coated with the biocompatible material. In some embodiments, the sensor is not or at least a portion of the sensor is not coated with the biocompatible material. For example, in some embodiments, the sensor comprises a pair of electrodes which are not coated with the biocompatible material, which allows the electrodes to detect changes in a physiological condition. In some embodiments, the biocompatible material is cured, for example by exposure to UV light or by heating.

Figure 15:
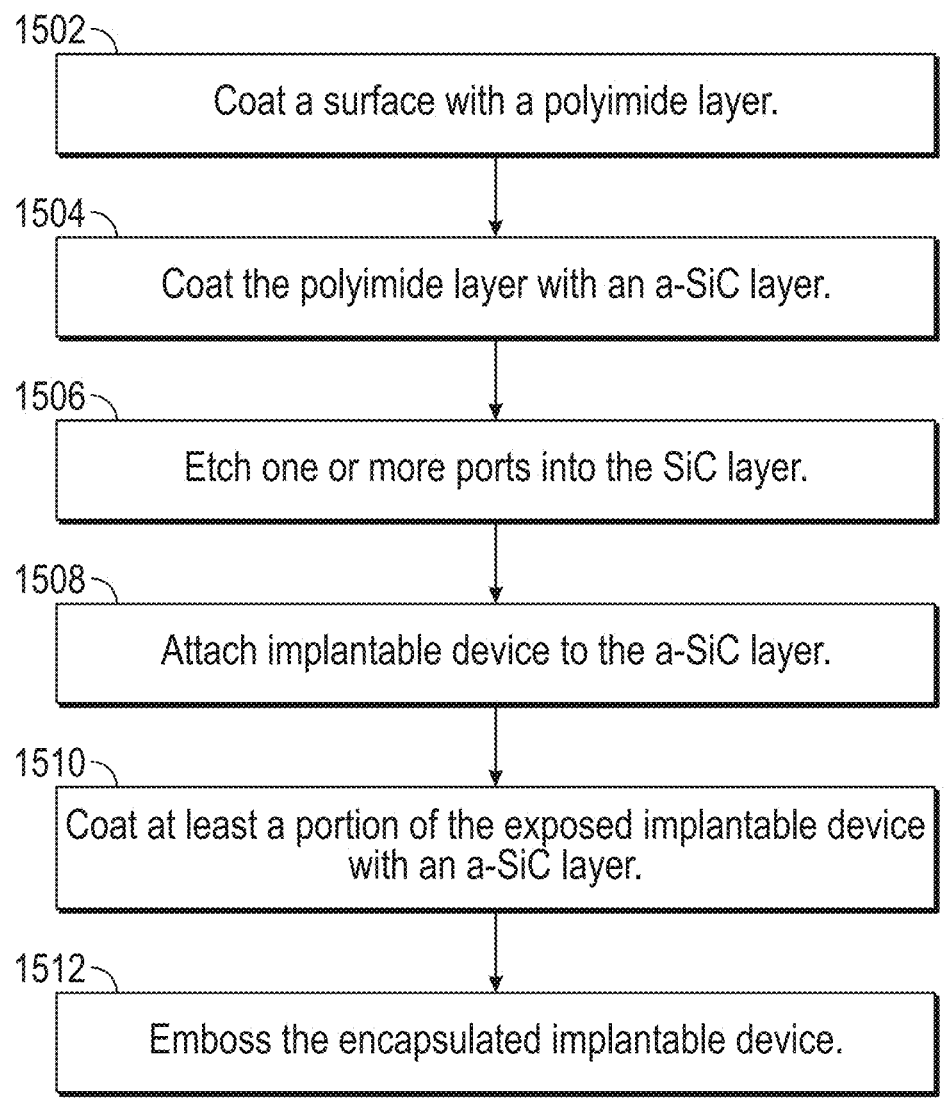
FIG. 15 is a flowchart for a method of encapsulating an implantable device with amorphous silicon carbide.

In some embodiments, the implantable device is encapsulated in an amorphous silicon carbide (a-SiC) film. FIG. 15 illustrates a method of manufacturing an implantable device encapsulated in an a-SiC film. At step 1502, a polyimide layer is applied to a smooth surface. At step 1504, an a-SiC layer is applied to the polyimide layer. This can be done, for example, using plasma enhanced chemical vapor deposition (PECVD), using $SiH_4$ and $CH_4$ as precursors. At step 1506, one or more ports are etched into the a-SiC layer. In some embodiments, ports are also etched into the polyimide layer. The ports provide access for portions of the implantable device that are not encapsulated by the a-SiC, such as portions of a sensor or an electrode that will contact the tissue, blood, or interstitial fluid after implant. In some embodiments, etching comprises reactive-ion etching. At step 1508, the implantable device is attached to the a-SiC layer. The implantable device may be pre-assembled before being attached to the a-SiC layer, or may be built on the a-SiC. In some embodiments, a printed circuit board (PCB), miniaturized ultrasonic transducer, and sensor are attached to the a-SiC layer. The miniaturized ultrasonic transducer and the sensor need not come in direct contact with the a-SiC layer, as they may be attached to the PCB. Attachment of miniaturized ultrasonic transducer or sensor to the PCB may occur before or after attachment of the PCB to the a-SiC layer. In some embodiments, attachment of miniaturized ultrasonic transducer or sensor to the PCB comprises wirebonding the miniaturized ultrasonic transducer or sensor to the PCB. In some embodiments, the sensor includes a portion that interfaces with the ports etched into the a-SiC layer. In some embodiments, an ASIC is attached to the PCB, which may occur before or after attachment of the PCB to the a-SiC layer. At step 1510, an exposed portion of the implantable device is coated with an a-SiC layer. In some embodiments, the exposed portion of the implantable device is coated with an a-SiC layer using PECVD. At step 1512, the encapsulated implantable device is embossed, thereby releasing the implantable device from the SiC layer.

EXEMPLARY EMBODIMENTS

Embodiment 1

An implantable device, comprising:
a sensor configured to detect an amount of an analyte, pH, a temperature, a strain, or a pressure; and
an ultrasonic transducer with a length of about 5 mm or less in the longest dimension, configured to receive current modulated based on the analyte amount, the pH, the temperature, or the pressure detected by the sensor, and emit an ultrasonic backscatter based on the received current.

Embodiment 2

The implantable device of embodiment 1, wherein the ultrasonic transducer is configured to receive ultrasonic waves that power the implantable device.

Embodiment 3

The implantable device of embodiment 2, wherein the ultrasonic transducer is configured to receive ultrasonic waves from an interrogator comprising one or more ultrasonic transducers.

Embodiment 4

The implantable device of any one of embodiments 1-3, wherein the ultrasonic transducer is a bulk piezoelectric transducer.

Embodiment 5

The implantable device of embodiment 4, wherein the bulk ultrasonic transducer is approximately cubic.

Embodiment 6

The implantable device of any one of embodiments 1-5, wherein the ultrasonic transducer is a piezoelectric micromachined ultrasonic transducer (PMUT) or a capacitive micro-machined ultrasonic transducer (CMUT).

Embodiment 7

The implantable device of any one of embodiments 1-6, wherein the implantable device is about 5 mm or less in length in the longest dimension.

Embodiment 8

The implantable device of any one of embodiments 1-7, wherein the volume of the implantable device is about 5 mm3 or less.

Embodiment 9

The implantable device of any one of embodiments 1-8, wherein the volume of the implantable device is about 1 mm3 or less.

Embodiment 10

The implantable device of any one of embodiments 1-9, wherein the implantable device is implanted in a subject.

Embodiment 11

The implantable device of embodiment 10, wherein the subject is an animal.

Embodiment 12

The implantable device of embodiment 10 or 11, wherein the subject is a human.

Embodiment 13

The implantable device of embodiment 10, wherein the subject is a plant.

Embodiment 14

The implantable device of any one of embodiments 1-3, wherein the sensor detects the amount of the analyte or pH.

Embodiment 15

The implantable device of embodiment 14, wherein the sensor is an optical sensor.

Embodiment 16

The implantable device of embodiment 15, wherein the optical sensor comprises a light source and an optical detector.

Embodiment 17

The implantable device of embodiment 15 or 16, wherein the optical sensor detects blood pressure or a pulse.

Embodiment 18

The implantable device of embodiment 15 or 16, wherein the optical sensor comprises a matrix comprising a fluorophore, and wherein fluorescence intensity or fluorescence lifetime of the fluorophore depends on the amount of the analyte.

Embodiment 19

The implantable device of any one of embodiments 15, 16, or 18, wherein the sensor detects pH or oxygen.

Embodiment 20

The implantable device of embodiment 15 or 16, wherein the optical sensor is configured to perform near-infrared spectroscopy.

Embodiment 21

The implantable device of embodiment 20, wherein the sensor detects glucose.

Embodiment 22

The implantable device of any one of embodiments 16-21, wherein the optical sensor comprises an optical filter on the light source or on the optical detector.

Embodiment 23

The implantable device of anyone of embodiments 16-22, wherein the optical sensor comprises an optical filter on the light source and the optical detector.

Embodiment 24

The implantable device of any one of embodiments 1-13, wherein the sensor is a potentiometric chemical sensor.

Embodiment 25

The implantable device of any one of embodiments 1-13, wherein the sensor is an amperometric chemical sensor.

Embodiment 26

The implantable device of embodiment 24 or 25, wherein the sensor detects oxygen, pH, or glucose.

Embodiment 27

The implantable device of any one of embodiments 1-13, wherein the sensor is a temperature sensor.

Embodiment 28

The implantable device of embodiment 27, wherein the temperature sensor is a thermistor, a thermocouple, or a proportional to absolute temperature (PTAT) circuit.

Embodiment 29

The implantable device of any one of embodiments 1-13, wherein the implantable device comprises a bulk piezoelectric ultrasonic transducer and a thermistor.

Embodiment 30

The implantable device of embodiment 1, wherein the sensor is a pressure sensor.

Embodiment 31

The implantable device of embodiment 30, wherein the pressure sensor is microelectromechanical system (MEMS) sensor.

Embodiment 32

The implantable device of embodiment 30 or 31, wherein the implantable device is configured to measure blood pressure or a pulse.

Embodiment 33

The implantable device of any one of embodiments 1-32, wherein the implantable device further comprises an integrated circuit.

Embodiment 34

The implantable device of embodiment 33, wherein the integrated circuit comprises a power circuit.

Embodiment 35

The implantable device of embodiments 33 or 34, wherein the integrated circuit comprises a driver configured to provide current to the sensor.

Embodiment 36

The implantable device of any one of embodiments 33-35, wherein the integrated circuit comprises a driver configured to provide current to one or more light sources.

Embodiment 37

The implantable device of any one of embodiments 34-36, wherein the integrated circuit comprises a front end configured to receive a signal from the sensor.

Embodiment 38

The implantable device of any one of embodiments 34-37, wherein the integrated circuit comprises a front end configured to receive a signal from a light detector.

Embodiment 39

The implantable device of embodiment 37 or 38, wherein the front end is a CMOS front end.

Embodiment 40

The implantable device of any one of embodiments 33-39, wherein the integrated circuit comprises a modulation circuit comprising a switch.

Embodiment 41

The implantable device of embodiment 40, wherein the switch comprises a field effect transistor (FET).

Embodiment 42

The implantable device of any one of embodiments 33-41, wherein the integrated circuit comprises an analog-to-digital converter (ADC).

Embodiment 43

The implantable device of any one of embodiments 33-42, wherein the integrated circuit comprises a digital circuit.

Embodiment 44

The implantable device of embodiment 43, wherein the digital circuit is configured to operate a modulation circuit.

Embodiment 45

The implantable device of embodiment 43 or 44, wherein the digital circuit is configured to transmit a digitized signal to the modulation circuit, wherein the digitized signal is based on the detected amount of the analyte, the temperature, or the pressure.

Embodiment 46

The implantable device of any one of embodiments 1-45, wherein the implanted device is at least partially encapsulated by a biocompatible material.

Embodiment 47

The implanted device of embodiment 46, wherein the biocompatible material is a copolymer of N-vinyl-2-pyrrolidinone (NVP) and n-butylmethacrylate (BMA), polydimethylsiloxane (PDMS), parylene, polyimide, silicon nitride, silicon dioxide, alumina, niobium, hydroxyapatite, silicon carbide, titania, steel, or titanium.

Embodiment 48

The implanted device of embodiment 46, wherein the biocompatible material comprises a ceramic or a metal.

Embodiment 49

The implantable device of any one of embodiments 1-48, wherein the implantable device further comprises a non-responsive reflector.

Embodiment 50

The implantable device of any one of embodiments 1-49, wherein the implantable device comprises two or more sensors.

Embodiment 51

A system comprising one or more implantable devices according to any one of embodiments 1-50 and an interrogator comprising one or more ultrasonic transducers configured to transmit ultrasonic waves to the one or more implantable devices or receive ultrasonic backscatter from the one or more implantable devices.

Embodiment 52

The system of embodiment 51, wherein the interrogator comprises a first ultrasonic transducer configured to transmit ultrasonic waves and a second ultrasonic transducer configured to receive ultrasonic backscatter from the one or more implantable devices.

Embodiment 53

The system of embodiment 51 or 52, wherein the interrogator comprises two or more separate interrogator devices, wherein a first interrogator device is configured to transmit ultrasonic waves to the one or more implantable devices and a second interrogator device is configured to receive ultrasonic backscatter from the one or more implantable devices.

Embodiment 54

The system according to any one of embodiments 51-53, wherein the interrogator comprises two or more ultrasonic transducer arrays, wherein each transducer array comprises two or more ultrasonic transducers.

Embodiment 55

The system according to any one of embodiments 51-54, wherein at least one of the one or more ultrasonic transducers is configured to alternatively transmit ultrasonic waves to the one or more implantable devices or receive ultrasonic backscatter from the one or more implantable devices, wherein the configuration of the transducer is controlled by a switch on the interrogator.

Embodiment 56

The system according to any one of embodiments 51-55, wherein the system comprises a plurality of implantable devices.

Embodiment 57

The system of embodiment 56, wherein the interrogator is configured to beam steer transmitted ultrasonic waves to alternatively focus the transmitted ultrasonic waves on a first portion of the plurality of implantable devices or focus the transmitted ultrasonic waves on a second portion of the plurality of implantable devices.

Embodiment 58

The system of embodiment 56, wherein the interrogator is configured to simultaneously receive ultrasonic backscatter from at least two implantable devices.

Embodiment 59

The system of embodiment 56, wherein the interrogator is configured to transit ultrasonic waves to the plurality of implantable devices or receive ultrasonic backscatter from the plurality of implantable devices using time division multiplexing.

Embodiment 60

The system of embodiment 56, wherein the interrogator is configured to transit ultrasonic waves to the plurality of implantable devices or receive ultrasonic backscatter from the plurality of implantable devices using spatial multiplexing.

Embodiment 62

The system of embodiment 56, wherein the interrogator is configured to transit ultrasonic waves to the plurality of implantable devices or receive ultrasonic backscatter from the plurality of implantable devices using frequency multiplexing.

Embodiment 63

The system according to any one of embodiments 51-62, wherein the interrogator is configured to be wearable by a subject.

Embodiment 64

A method of detecting an amount of an analyte, a pH, a temperature, or a pressure, comprising:
receiving ultrasonic waves that power one or more implantable devices comprising an ultrasonic transducer with a length of about 5 mm or less in the longest dimension;
converting energy from the ultrasonic waves into an electrical current;
transmitting the electrical current to a sensor configured to measure the amount of the analyte, the pH, the temperature, or the pressure;
modulating the electrical current based on the measured amount of the analyte, pH, temperature, or pressure;
transducing the modulated electrical current into an ultrasonic backscatter that encodes the measured amount of the analyte, pH, temperature, or pressure; and
emitting the ultrasonic backscatter to an interrogator comprising one or more transducer configured to receive the ultrasonic backscatter.

Embodiment 65

A method of detecting an amount of an analyte, a pH, a temperature, or a pressure, comprising:
receiving ultrasonic waves that power one or more implantable devices comprising an ultrasonic transducer with a length of about 5 mm or less in the longest dimension;
converting energy from the ultrasonic waves into an electrical current;
measuring the amount of the analyte, the pH, the temperature, or the pressure using a sensor;
modulating the electrical current based on the measured amount of the analyte, pH, temperature, or pressure;
transducing the modulated electrical current into an ultrasonic backscatter that encodes the measured amount of the analyte, pH, temperature, or pressure; and
emitting the ultrasonic backscatter to an interrogator comprising one or more transducer configured to receive the ultrasonic backscatter.

Embodiment 66

The method of embodiment 64 or 65, further comprising receiving the ultrasonic backscatter using the interrogator.

Embodiment 67

The method of any one of embodiments 64-66, further comprising transmitting the ultrasonic waves using the interrogator configured to transmit the ultrasonic waves.

Embodiment 68

The method of embodiment 67, wherein the ultrasonic waves are transmitted in two or more pulses.

Embodiment 69

The method of any one of embodiments 64-68, comprising analyzing the ultrasonic backscatter to determine the measured amount of the analyte, pH, temperature, or pressure.

Embodiment 70

The method of any one of embodiments 64-69, wherein the method comprises measuring the amount of the analyte or pH.

Embodiment 71

The method of any one of embodiments 64-70, wherein the method comprising measuring an amount of oxygen or pH.

Embodiment 72

The method of any one of embodiments 64-71, wherein the method comprises monitoring tissue oxygenation levels.

Embodiment 73

The method of embodiment 72, wherein the one or more implantable devices are implanted on, within, or proximal to a blood vessel, implanted organ, or a tumor.

Embodiment 74

The method of any one of embodiments 64-73, comprising emitting light and detecting fluorescence intensity or fluorescence lifetime, wherein the fluorescence intensity or fluorescence lifetime depends on the amount of the analyte or the pH.

Embodiment 75

The method of embodiment 74, comprising determining a phase shift between oscillating emitted light and detected fluorescence is determined, wherein the phase shift depends on the amount of the analyte or the pH.

Embodiment 76

The method of embodiment 74 or 75, comprising determining a fluorescent lifetime for the detected fluorescence resulting from pulsed or oscillating emitted light.

Embodiment 77

The method of any on one of embodiments 64-70, wherein the method comprises measuring an amount of glucose.

Embodiment 78

The method of any one of embodiments 64-69, comprising measuring the temperature.

Embodiment 79

The method of embodiment 78, wherein the one or more implantable devices are implanted on, within, or proximal to a blood vessel, implanted organ, or a tumor.

Embodiment 80

The method of embodiment 78 or 79, comprising monitoring temperature of an organ or a site of an infection.

Embodiment 81

The method of any one of embodiments 64-69, comprising measuring the pressure.

Embodiment 82

The method of embodiment 81, comprising measuring a pulse rate or a blood pressure.

Embodiment 83

The method of any one of embodiments 64-82, comprising determining a relative location of the one or more implantable devices.

Embodiment 84

The method of any one of embodiments 53-83, comprising detecting angular or lateral movement of the one or more implantable devices.

Embodiment 85

The method of embodiment 84, comprising analyzing the ultrasonic backscatter to determine the measured amount of the analyte, the temperature, or the pressure, wherein the analysis comprises accounting for angular or lateral movement of the implantable device.

Embodiment 86

The method of any one of embodiments 64-85, comprising implanting the implantable device in a subject.

Embodiment 87

The method of embodiment 86, wherein the subject is an animal.

Embodiment 88

The method of embodiment 86 or 87, wherein the subject is a human.

Embodiment 89

The method of embodiment 86, wherein the subject is a plant.

Embodiment 90

The method of any one of embodiments 64-89, wherein the ultrasonic backscatter encodes a digitized signal.

Embodiment 91

The method of any one of embodiments 64-90, comprising receiving the ultrasonic backscatter.

Embodiment 92

The method of embodiment 91, wherein the ultrasonic backscatter is received from a plurality of implantable devices.

Embodiment 93

The method of embodiment 92, wherein the ultrasonic backscatter is received from the plurality of implantable devices using time division multiplexing.

Embodiment 94

The method of embodiment 92, wherein the ultrasonic backscatter is received from the plurality of implantable devices using spatial multiplexing.

Embodiment 95

The method of embodiment 92, wherein the ultrasonic backscatter is received from the plurality of implantable devices using frequency multiplexing.

Embodiment 96

A medical system comprising:
an ultrasound transceiver configured to generate ultrasound interrogation pulses at an adjustable at least one of frequency, amplitude, phase and duty cycle, and receive ultrasound backscatter produced by transmitted ultrasound interrogation pulses; and
an implantable device comprising leads to sense a body condition, and circuitry to reflect received ultrasound interrogation pulses modulated based upon a body condition sensed by the leads.

Embodiment 97

The medical system of embodiment 96, wherein the ultrasound transceiver is implantable, and is further configured to communicate wirelessly with an external transceiver.

Embodiment 98

The medical system of any of embodiments 96-97, wherein the at least one of frequency, amplitude, phase and duty cycle of generated ultrasound interrogation pulses is adjustably set based upon a determined distance between an ultrasound transceiver and the implantable device.

Embodiment 99

The medical system of embodiment 98, wherein the at least one of frequency, amplitude, phase and duty cycle corresponds to a focal length of ultrasound transmissions suitable given the determined distance between an ultrasound transceiver and the implantable device.

Embodiment 100

The medical system of any of embodiments 98-99, wherein the system is configured to determine the distance between an ultrasound transceiver.

Embodiment 101

The medical system of any of embodiments 97-100, wherein the distance determination is made by an external transceiver.

Embodiment 102

A medical system comprising:
an ultrasound transceiver configured to generate ultrasound interrogation pulses and receive ultrasound backscatter produced by transmitted ultrasound interrogation pulses; and
an implantable device comprising leads to sense a biological condition, at least one responsive region responsive to a sensed biological condition sensed by the leads, and at least one non-responsive region that is not responsive to the sensed biological condition, the implantable device reflects received ultrasound interrogation pulses producing a particular pulse signature with at least one portion of the signature corresponding to the at least one responsive region at least one other portion of the signature corresponding to the at least one non-responsive region.

Embodiment 103

The medical system of embodiment 102, wherein the system comprises a plurality of the implantable devices with different configurations of the responsive and non-responsive regions, to produce a different pulse signatures.

Embodiment 104

The medical system of embodiment 103, wherein the pulse signature is used by the system to determine an identity of the implantable device that produced an ultrasound reflection.

Embodiment 105

A medical system comprising:
an ultrasound transceiver comprising an array of transducers each configured to generate ultrasound interrogation pulses, each transducer comprising one of a micro-machined structure and bulk piezo crystal, the transceiver further configured to receive ultrasound backscatter produced by transmitted ultrasound interrogation pulses; and
multiple implantable devices each comprising leads to sense a body condition, and circuitry to reflect received ultrasound interrogation pulses modulated based upon a body condition sensed by the leads.

Embodiment 106

The medical system of embodiment 105, wherein the ultrasound transceiver steers ultrasound beams generated by the transducers.

Embodiment 107

The medical system of any of embodiments 105 or 106, wherein communication between the ultrasound transceiver and the multiple implantable devices uses time division multiplexing.

Embodiment 108

The medical system of any of embodiments 105 or 106, wherein communication between the ultrasound transceiver and the multiple implantable devices uses spatial multiplexing.

Embodiment 109

The medical system of any of embodiments 105 or 106, wherein communication between the ultrasound transceiver and the multiple implantable devices uses frequency multiplexing.

Embodiment 110

An internal body condition sensing system, comprising:
an ultrasound transceiver configured to generate ultrasound transmissions and receive ultrasound backscatter produced by generated ultrasound transmissions; and
a body implantable device comprising an optical sensor to sense an internal body biologic condition, and comprising an ultrasound backscatter communication system to modulate in reflected ultrasound backscatter communications information indicative of the internal body biologic condition.

Embodiment 111

The internal body biologic condition sensing system of embodiment 110, wherein the body implantable device additionally comprises an optical emitter.

Embodiment 112

The internal body biologic condition sensing system of embodiment 110, wherein the optical sensor is configured to measure tissue oxygenation levels.

Embodiment 113

The internal body biologic condition sensing system of any of embodiments 110 or 111, wherein the optical sensor is configured to perform near-infrared spectroscopy.

Embodiment 114

The internal body biologic condition sensing system of embodiment 110, wherein the optical sensor is configured to measure a blood analyte.

Embodiment 115

The internal body biologic condition sensing system of embodiment 113, wherein the analyte is glucose.

Embodiment 116

The internal body biologic condition sensing system of embodiment 113, wherein the analyte is pH.

Embodiment 117

The internal body biologic condition sensing system of embodiment 110, wherein the optical sensor is configured to measure blood pressure.

Embodiment 118

A method of sensing an internal body biologic condition, comprising:
implanting at a location of interest a body implantable device comprising an optical sensor to sense an internal body biologic condition, the body implantable device further comprising an ultrasound backscatter communication system to modulate in reflected biologic condition; and
using an ultrasound transceiver configured to generate ultrasound transmissions and receive ultrasound backscatter produced by generated ultrasound transmissions, to interrogate the body implantable device to obtain information indicative of the sensed internal biologic condition.

Embodiment 119

The method of embodiment 118, wherein the optical sensor is configured to measure tissue oxygenation levels.

Embodiment 120

The method of embodiment 118, wherein the body implantable device is implanted in a location at or near a tumor, to monitor tumor oxygenation.

Embodiment 121

The method of embodiment 118, wherein a plurality of ones of the body implantable device are implanted at various locations in the brain, and the method further comprises performing functional brain imaging the information indicative of the sensed internal biologic condition of the brain.

Embodiment 122

The method of embodiment 118, wherein the optical sensor is configured to measure a blood analyte.

Embodiment 123

The method of embodiment 122, wherein the analyte is glucose.

Embodiment 124

The method of embodiment 123, wherein the analyte is pH.

Embodiment 125

The method of embodiment 118, wherein the optical sensor is configured to measure blood pressure.

Embodiment 126

An internal body condition sensing system, comprising:
an ultrasound transceiver configured to generate ultrasound transmissions and receive ultrasound backscatter produced by generated ultrasound transmissions; and
a body implantable device comprising a pressure sensor to sense an internal body biologic condition, and comprising an ultrasound backscatter communication system to modulate in reflected ultrasound backscatter communications information indicative of the internal body biologic condition.

Embodiment 127

An internal body condition sensing system, comprising:
ultrasound backscatter produced by generated ultrasound transmissions; and a body implantable device comprising a temperature sensor to sense an internal body biologic condition, and comprising an ultrasound backscatter communication system to modulate in reflected ultrasound backscatter communications information indicative of the internal body biologic condition.

Embodiment 128

An internal body condition sensing system, comprising:
an ultrasound transceiver configured to generate ultrasound transmissions and receive ultrasound backscatter produced by generated ultrasound transmissions; and
a body implantable device comprising a potentiometric chemical sensor to sense an internal body biologic condition, and comprising an ultrasound backscatter communication system to modulate in reflected ultrasound backscatter communications information indicative of the internal body biologic condition.

Embodiment 129

An internal body condition sensing system, comprising:
an ultrasound transceiver configured to generate ultrasound transmissions and receive ultrasound backscatter produced by generated ultrasound transmissions; and
a body implantable device comprising an amperometric chemical sensor to sense an internal body biologic condition, and comprising an ultrasound backscatter communication system to modulate in reflected ultrasound backscatter communications information indicative of the internal body biologic condition.

EXAMPLES

Example 1—Manufacture of an Implantable Device

In short form, the assembly steps of the implantable device are as follows:
1. Attach ASIC to PCB.
2. Wirebond ASIC ports to PCB.
3. Attach piezoelectric element to PCB.
4. Wirebond piezoelectric element ports to PCB.
5. Encapsulate full device except for recording electrodes.

The ASIC measures 450 µm by 500 µm by 500 pm and is fabricated by Taiwan Semiconductor Manufacturing Company's 65 nm process. Each chip contains two transistors with 5 ports each: source, drain, gate, center, and bulk. Each FET uses the same bulk, so either bulk pad can be bonded to, but the transistors differ in that the transistor padded out to the top row does not contain a resistor bias network whereas the transistor padded out in the bottom row does. The chip additionally contains smaller pads for electroplating. The same process can be applied to ASIC's with more complex circuitry and thus more pads. These pads were not used in this example. Three versions of the FET were taped out:
Die 1: Long channel FET with threshold voltage: 500 Mv.
Die 2: Short channel FET with threshold voltage at 500 mV.
Die 3: Native FET with threshold voltage at 0 mV.

Confirmation of electrical characteristics of these FETs were measured using a specially designed CMOS characterization board which contained of a set of pads as wirebonding targets and a second set of pads in which wires were soldered to. A sourcemeter (2400 Sourcemeter, Keithley Instruments, Cleveland, Ohio) was used to supply $V_{DS}$ to the FET and measure $I_{DS}$. An adjustable power supply (E3631A, Agilent, Santa Clara, Calif.) was used to modulate $V_{GS}$ and the I-V characteristics of the FETs were obtained. Uncharacteristic IV curves for type 2 dies were consistently measured, and upon impedance measurement, found that the short channel of the die 2s would short out the FET.

The piezoelectric element is lead-zirconium titanate (PZT). It is purchased as a disc from APC International and diced into 750 µm×750 µm×750 µm cubes using a wafer saw (DAD3240, Disco, Santa Clara, Calif.) with a ceramic blade (PN CX-010-'270-080-H). This mote size was chosen as it maximized power transfer efficiency. For more details, see Seo et al., *Neural dust: an ultrasonic, low power solution for chronic brain-machine interfaces*, arXiv: 1307.2196v1 (Jul. 8, 2013).

The implantable device substrate integrates the ASIC with the piezoelectric element and recording electrodes. The first version of the implantable device used custom-designed PCBs purchased from The Boardworks (Oakland, Calif.) as a substrate. The PCBs were made of FR-4 and were 30 mil (approximately 0.762 mm) in thickness. The dimensions of the board were 3 mm×1 mm. This design was the first attempt an integrated communication and sense platform, so pad size and spacing was chosen to facilitate assembly at the cost of larger size. To conserve PCB real-estate, each face of the PCB included pads for either the piezoelectric element or the ASIC and its respective connections to the PCB. Additionally, two recording pads were placed on the ASIC-face of the board. All exposed electrodes were plated with ENIG by The Boardworks. The pad for the ASIC to sit on was 500 µm by 500 µm, chosen to fit the size of the die. The wirebond target pad size was chosen to be 200 µm by 200 µm and spaced roughly 200 µm away from the edge of the die in order to give enough clearance for wirebonding (discussed below). Electrode size and spacing varied and were empirically optimized.

Figure 16A:
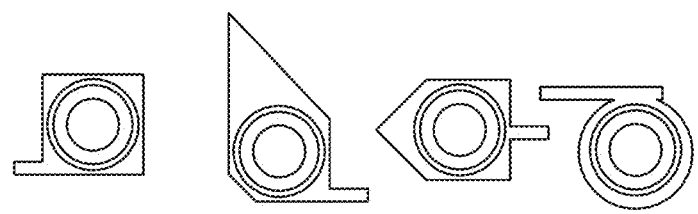
FIG. 16A shows different geometries of vias used to connect components of the implantable device.

In the second iteration of implantable device, three concerns primary concerns were addressed: 1) size, 2) ease of wirebonding, 3) implantation/communication. First, to decrease board thickness the FR-4 substrate was replaced with a 2 mil (about 50.8 µm) thick polyimide flexible PCB (AltaFlex, Santa Clara, Calif.), as well as thinning the ASIC (Grinding and Dicing Services Inc., San Jose, Calif.) to 100 µm. To facilitate bonding, the ASIC and PZT coupon were moved to the same side, with only the recording electrodes on the backside of the substrate. While putting the ASIC and PZT coupon on the same side of the board does impose a limit on how much the substrate size can be reduced, spacing between the electrodes restricted the board length of at least 2 mm. To push minimization efforts ASIC bonding pads were reduced to 100 µm by 100 µm, but the 200 µm spacing between bonding pads and the ASIC itself had to be maintained to provide space for wirebonding. The attachment pads for the PZT coupon was also shrunk and placed closer to the edge of the board, with the rationale that the PZT coupon did not have to wholly sit on the board, but could hang off it. Additionally, the location of the pads relative to the ASIC was also modified to facilitate bonding. In the original design, the bond pad layout surrounding the ASIC required two wirebonds to cross. This is not impossible, but very difficult to avoid shorting the pads. Thus, the pad layout was shifted so that the bonds are relatively straight paths. Finally, during animal experiments, it was found that alignment of the implantable device was quite difficult. To combat this, four 1 inch test leads that extended off the board were added, two of which connected directly to the source and drain of the device to harvest power could be measured and to use that as an alignment metric. The other two leads connect to the gate and center ports in order to obtain a ground truth signal. In order to prevent confusion over which lead belonged to which port, the vias were given unique geometries. See FIG. 16A.

Figure 16B:
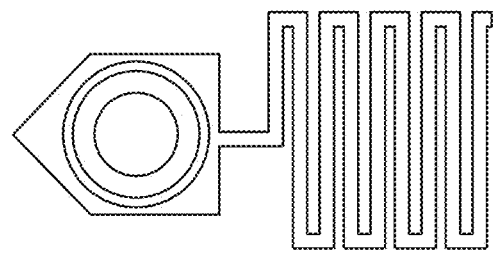
FIG. 16B shows a serpentine trace configuration for deformable interconnects.

There was some fear that the test leads may be easily broken or would easily displace the mote if force was applied on them. Thus, a version with serpentine traces was designed. Serpentine traces (FIG. 16B) have often been used to enable deformable interconnects, as their structure allows them to "accordion" out. Conceptually, the serpentine trace design can be through of a series of cantilevers in series via connector beams.

Along with the presented designs, a miniaturized version of the implantable device using both sides of the substrate was also designed and assembled. In this design, the board measures roughly 1.5 mm by 0.6 mm by 1 mm. Due to the miniaturization of the board, a 5 mil silver wire "tail" was attached to the device for recording. This version was not tested in vivo.

The ASIC and PZT coupon were attached to the PCB substrate using adhesives. There are three majors concerns to choosing an adhesive: 1) the adhesive needs to fix the ASIC and PZT tightly enough that the ultrasonic power from wirebonding does not shake the components, 2) due to the sub-millimeter scales and pitches of the components/substrate pads, application of the adhesive was done in a relatively precise way, and 3) the adhesive must be electrically conductive.

Figure 17:
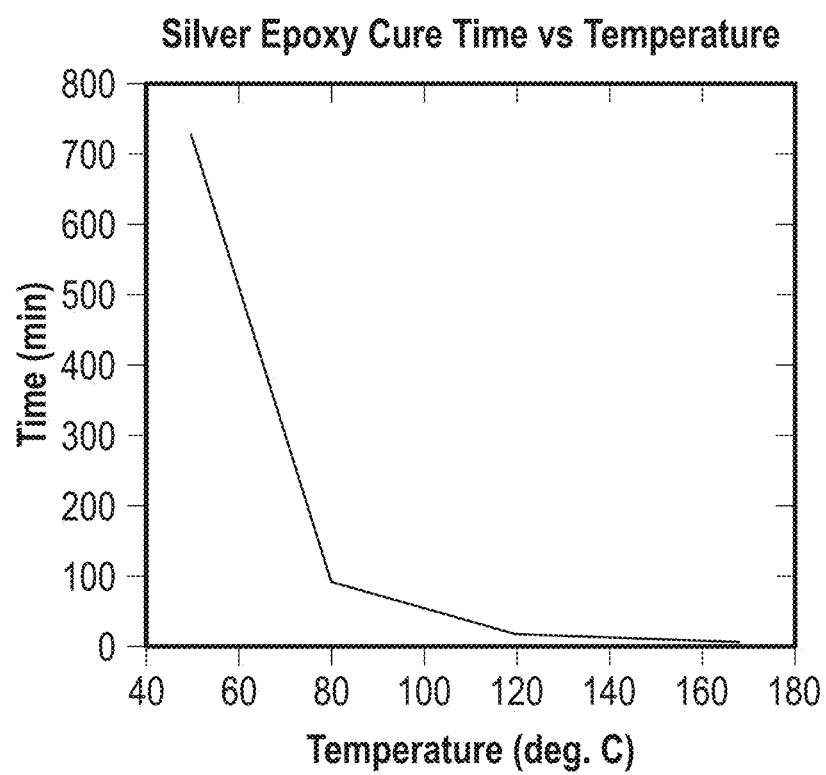
FIG. 17 shows the relationship between time and temperature for curing silver epoxy, an exemplary material for attaching wirebonds during the manufacture of the implantable device.

The ASIC and diced PZT were originally attached to the PCB substrate using a low temperature-curing solder paste. Solder paste consists of powder metal solder suspended as spheres in flux. When heat is applied, the solder balls begin to melt and fuse together. However, it was found that the curing of the solder paste would often result in translating or rotating the PZT coupon or mote during reflow. This presented problems for PZT alignment and power harvesting, as well as problems for wirebonding due to the bondpads no longer being appropriately positioned from the chip. However, it was found that a two-part silver epoxy, which simply consists of silver particles suspended in epoxy was capable of curing without repositioning the chip or PZT coupon. Thus, the ASIC and diced PZT were pasted onto the PCB using a two-part conductive silver epoxy (H20E, Epotek, Billerica, Mass.). The PCBs were then affixed to a glass slide using Kapton tape (Polyimide Film Tape 5413, 3M, St. Paul, Minn.) and put into a convection oven at 150° C. for 15 minutes to cure the epoxy. While higher temperatures could yield faster curing (FIG. 17), care was taken to avoid heating the PZT beyond 160° C., half the Curie temperature of the PZT. Heating the PZT any higher runs the risk of depolarizing the PZT. It was found that the 150° C. cure had no effect on the CMOS performance.

The connections between the top of the PZT and the PCB as well as the ASIC and the PCB were made by wirebonding 1 mil Al wire using an ultrasonic wedge bonder (740DB, West Bond, Scotts Valley, Calif.); in this method of bonding, the Al wire is threaded through the wedge of the bondhead and ultrasonic energy "scrubs" the Al wire against the substrate, generating heat through friction. This heat results in welding the two materials together.

Wirebonding to the ASIC was challenging to avoid shorts due to the size of the CMOS pads and the size of the foot of the wirebond. This problem was accentuated due to the positioning of the wirebonding targets in the first version of the implantable device board, which forced the feet of two bonds to be placed across the smaller width of the ASIC pad rather than the length. While thinner gold wire was available to use for bonding, the difficulty of bonding gold thermosonically with a wedge bonder made it impractical to use gold wires for bonding with this equipment. Furthermore, in order to effectively wirebond, it is important to have a flat and fixed substrate; hence, our original design of having the ASIC and PZT on different sides of the board often caused trouble during the wirebonding process in our first version of implantable boards. Thus, the substrate design choices made in the second iteration of the implantable device (moving ASIC and PZT to the same side, repositioning the pads to provide straight paths to wirebond targets) greatly improved wirebonding yield.

Finally, because an ultrasonic bonder was used, it was found that bonding to the PZT resulted in a charge build up would damage the chip once the PZT was fully bonded to the substrate. To avoid this, the source and drain test leads of the device were discharged to Earth ground directly prior to wirebonding the PZT.

The final step of the implantable device assembly is encapsulation. This step achieves two goals: 1) insulation of the PZT, bondpads, and ASIC from aqueous environments and 2) protection of the wirebonds between the ASIC/PZT coupon and the PCB. At the same time, there must be some method to either remove or prevent the encapsulant from covering the recording electrodes. Additionally, the encapsulant must not impede device implantation. Finally, while it is not crucial, it is of interest to choose an encapsulant that is optically transparent so that the device can be inspected for physical defects if some damage occurred during the encapsulation.

The first encapsulant used was Crystalbond (509', SPI Supplies, West Chester, Pa.). Crystalbond is an adhesive that is solid at room temperature but begins to soften' at 71° C. and melts into a viscous liquid at 121° C. Upon removing heat from the Crystalbond, it re-solidifies within minutes, allowing for good control. To encapsulate the implantable device, a small flake of Crystalbond was shaved off with a razor and placed directly over the device. The board was then heated using a hotplate, first bringing the temperature to around 70° C. when the flake would begin to deform and then slowly increasing the temperature until the Crystalbond became fully liquid. Once the edge of the liquid Crystalbond drop expanded past the furthest wirebond but not the recording pad, the hotplate was turned off and the board was quickly moved off the plate onto a cooling chuck where the Crystalbond would re-solidify.

While Crystal bond was effective, it was found that UV curable epoxide could give us better selectivity and biocompatibility, as well as rapid curing. First, a light-curable acrylic (3526, Loctite, Dusseldorf; Germany) was tested, which cures with exposure to ultraviolet light. A sewing needle was used as an applicator to obtain high precision and the epoxy was cured with a 405 nm laser point for 2 minutes. This epoxy worked well, but was not medical-grade and thus not appropriate for a biological implant. Thus, a medical-grade UV curable epoxy (OG116-31, EPO-TEK, Billercia, Mass.) was tried. The epoxy was cured in a UV chamber (Flash, Asiga, Anaheim Hills, Calif.) with 92 mW/cm$^2$ at 365 nm for 5 minutes. While this epoxy was slightly less viscous than the Loctite epoxy, using a sewing needle again as an applicator allowed for selective encapsulation. As an insulator and protection mechanism for the wirebonds; the epoxy was very effective, but was found to leak during prolonged submersion in water (~1 hour). A second medical grade epoxy which touted stability for up to a year, was considered (301-2, EPO-TEK, Billerica, Mass.), but was found to be not viscous enough and required oven-baking for curing. Despite the instability of the UV epoxy, the duration of use was suitable for acute in vivo experiments.

To improve encapsulant stability, parylene-C was. also. considered as an encapsulation material. Parylene-C is an FDA approved biocompatible polymer which is chemically and biologically inert, a good barrier and electrical insulator, and extremely conformal when vapor deposited). Vapor deposition of Parylene-C is achieved by vaporizing powder Parylene-C dimer at temperatures above 150° C. The vapor Parylene-C dimer is then heated at 690° C. in order for pyrolysis to occur, cleaving the Parylene-C dimer into monomers. The monomer then fills the chamber, which is kept at room temperature. The monomer almost instantaneously polymerizes once it comes into contact with any surfaces. For all devices, Paraylene-C was deposited using a parylene deposition system (SCS Labcoter 2 Parylene Deposition System, Specialty Coating Systems, Indianapolis, Ind.) with the parameters shown in Table 1. Note that the table indicates the chamber gauge temperature as 135° C. This is distinct from the actual chamber temperature; rather the chamber gauge is simply the vacuum gauge of the process chamber. It is important to keep the temperature to at least 135° C. to prevent parylene from depositing onto the gauge. For the first batch of FR-4 boards, parylene was addressed by selectivity by using Kapton tape to mask off the electrodes. However, it was found that due to the small pitch between the recording electrodes and the ASIC wire-bonding targets, there was not enough surface area for the tape to affix well to the board and it often slipped off, resulting in coated electrode pads. In the second iteration of implantable device, a parylene coat was attempted using a strategy in which the entire board was coated, then remove the parylene off the electrodes with a probe tip. In order to assure that parylene was coated onto the entire device, the implantable devices were suspended in air by damping them between two stacks of glass slides.

TABLE 1

Parylene-C Deposition Parameters

| Furnace Temperature | 690 deg. C. |
| Chamber Gauge Temperature | 135 deg. C. |
| Vaporizer Temperature | 175 deg. C. |
| Base Pressure | 14 mTorr |
| Operating Pressure | 35 mTorr |
| Paralyene-C Mass | 5 g |

The following provides additional details for manufacturing the implantable device.

Before beginning to work with the PCBs, ASICs, or PZT coupons, prepare two sample holders for the dust boards. To do so, simply take two glass slides (3 mm×1 mm×1 mm slides work well) and put a strip of double-sided tape on the slide lengthwise. The tape will be used to fix the dust motes in place so that the rest of the steps can be performed. On one of the slides, also add a piece of Kapton tape (3M) sticky-side up on top of the double-sided tape. This slide will be the slide used for curing as the high temperature of the cure can cause problems with the adhesive on the double-sided tape.

Next, mix a small amount of silver paste by weighing out a 1:1 ratio of part A and part B in a weigh boat. A large amount of silver-epoxy is not needed for the assembly process. Shown below is roughly 10 g of epoxy (5 g of each part) which is more than enough for three boards, Note that the mixed-silver epoxy has a shelf life of two weeks if placed at 4° C. So leftover epoxy can and should be refrigerated when not in use. Additionally, older epoxies (several days to a week) tend to be slightly more viscous than fresh epoxy which can make application easier.

The substrates come panelized and will need to be removed. Each board is connected to the panel at several attachment points on the test leads and vias—these attachment points can be cut using a micro-scalpel (Feather Safety Razor Co., Osaka, Japan). Once the PCB has been singulated, using carbon-fiber tipped tweezers. or ESD plastic tweezers, place the singulated PCB onto the high-temperature sample holder.

The diced/thinned die are shipped on dicing tape, which can make it tricky to remove the die. In order to reduce the adhesion between the die and tape, it can be helpful to deform the tape. Using carbon-tipped or ESD plastic tweezers, gently press the tape and work the tweezers in a circular motion around the die. To check if the die has been freed, gently nudge the chip with the tip of the tweezers. If the die does not come off easily, continue to press into tape surrounding the chip. Once the chip has come off, carefully place the chip onto the high-temperature sample holder next to its board. It is advisable to bring the sample holder to the chip rather than the other way around so that the chip is not in transit, Care must be taken in this step to avoid losing or damaging the die. Never force a die off the tape, as excessive force can cause a chip to fly off the tape.

Next, attach the die using silver epoxy. Under a microscope, use a pin or something equally fine to apply a small amount silver epoxy to the CMOS pad on the PCB. In this step, it is better to err on the side of too little epoxy than too much epoxy since more silver paste can always be applied, but removing silver paste is non-trivial. Small amounts of uncured epoxy can be scraped away with the same tool used for application, just ensure the epoxy has been wiped off the tool.

Once the epoxy has been placed on the pad, the ASIC can be placed onto the epoxy. Due to a CAD error, some of the chips have been reflected. It is important to take care that chips which are reflected have been oriented the correct way on the board to ensure no wires need to cross during wirebonding.

Once the ASICs have been situated on the boards correctly, the silver epoxy can be cured by placing it into an oven at 150° C. for 15 minutes. Note that different temperatures can be used if needed. See FIG. 17 for details. After the silver epoxy has been cured, double-check adhesion by gently pushing on each die, If the die moves; a second coat of silver epoxy will be needed.

To prepare for wirebonding, move the devices from the high-temperature sample holder to the regular sample holder. This change is necessary because the adhesion of double-sided tape is stronger than that of the Kapton tape so wirebonding will be made easier. A piece of double-sided tape should be good enough to affix the sample holder to the wirebonder's workholder. It is best to ensure that the workholder has not been previously covered with double-sided tape so that the test leads do not get accidentally stuck to anything. If necessary, clean-room tape can be used to provide additional clamping of the sample holder.

Ensure the wirebonder is in good condition by making bonds on the provided test-substrate using default settings. Ensuring that the wirebonder is in condition is important, as a damaged wedge will not bond well and effectively just damage the ASIC pads. Forward bonds (first bond on the die, second bond on the substrate) should be made in the following order: 1. Gate. 2. Bulk. 3. Center. 4. Drain. 5. Source. While it is not critical that the bonds be made in this order, this order minimizes the number of substrate reorientations and prevents accidental damage to the bonds due to the bondhead. Small angle adjustments of the workholder can be made to facilitate bonding; it is imperative that this bond be as straight as possible. In the case that the foot of the second bond lifts from the substrate, changing the number of bonds to one and bonding the foot again may help. If proper adhesion cannot be made, a potential solution is to connect the foot of the bond and the substrate using silver epoxy. Additionally, shorts caused by two bond-feet touching can be resolved by very carefully cutting away the bridging metal using a microscalpel.

Known working bonding parameters can be found in Table 2, below. These parameters are simply guidelines and should be modified as necessary. Needing excess power (greater than 490) is typically indicative of a problem: substrate fixing (both PCB to glass slide and CMOS to PCB), wedge condition, and pad condition should all be checked. In the case of pad condition, damaged pads due to previous wirebonding attempts will usually require higher power—in some cases, the devices are salvageable, but failed attempts to bond with power higher than 600 usually results in too much damage to the pads for good bonding.

TABLE 2

Westbond 7400B A1 Parameters for ASIC

| Bond # | Power | Time |
|---|---|---|
| 1 (ASIC) | 420 | 40 ms |
| 2 (Substrate) | 420 | 40 ms |

Post-wire bonding, the device should undergo electrical testing to ensure proper bonding. If using a type 1 die, the I-V characteristics should be roughly as shown in Table 3.

TABLE 3

Typical I-V characteristics for Type 1 Die under $V_{ds} = 0.1$ V

| $V_{gs}$ | $I_{ds}$ |
|---|---|
| 0 V | 0.5 µA |
| 0.1 V | 0.74 µA |
| 0.2 V | 10.6 µA |
| 0.3 V | 51.4 µA |
| 0.4 V | 0.192 mA |
| 0.5 V | 0.39 mA |
| 0.6 V | 1.14 mA |
| 0.7 V | 1.55 mA |
| 0.8 V | 1.85 mA |

If the I-V characteristics do not seem correct, a valuable troubleshooting method is checking the resistances between the drain and center, source and center, and drain and source. If the die is working properly, one should expect roughly 90 kΩ resistance between the drain and center and source and center, and roughly 180 kΩ between the drain and source.

After confirmation that the FET is connected properly, the PZT coupon should be attached. This is done in a similar fashion to attaching the ASIC: place a dab of silver epoxy using a sewing needle on the appropriate pad. It is best to put the epoxy dab on the back edge of the pad (towards the end of the board) since the PZT coupon will not be centered on the pad, but pushed back so that the coupon hangs off the board. Keep in mind that the polarity of the PZT coupon has a small effect on its efficiency. To determine whether or not the coupon is in the correct position, check if the bottom face is larger than the top face. Due to the path of the dicing saw, the bottom of the coupon, is slightly larger than the top of the coupon. Thus, the edges of the bottom face can be seen from a top down view, then the coupon has been placed in the same orientation as it was when the disk was diced.

Wirebonding the PZT is done in a similar manner to the ASIC (forward bonding, the PZT to the PCB). However, one crucial change is that the drain and source vias should be grounded. There is an earth ground port next to Westbond which can be accessed via a banana connector. As a guideline, the parameters shown in Table 4 have been known to work.

TABLE 4

Westbond 7400B A1 Parameters for PZT

| Bond # | Power | Time |
|---|---|---|
| 1 (PZT) | 390 | 40 ms |
| 2 (Substrate) | 490 | 40 ms |

A successful bond may require several attempts depending on how well the PZT coupon is attached to the substrate. The more attempts that are made, the worse the mechanical structure of the PZT becomes (the silver coating will become damaged) so it is best to try to very quickly optimize the process. Bonds that fail due to foot detachment generally imply not enough power. Bonds that fail due to the wire breaking at the foot generally imply too much power.

After a successful bond is made, it is always good to do another electrical test to ensure that bonding the PZT has not damaged the ASIC.

As a final step, test wires were soldered to the vias and encapsulate the device, The test wires are 3 mil silver wires. Nate that these wires are insulated: the insulation can be removed by putting the wire close to a flame (not in the flame) and watching the plastic melt and recede.

After soldering wires, the device can now be encapsulated. The encapsulant is OG116-31 medical-grade UV curable epoxy and should be dispensed using a sewing needle. An effective method is to put a large drop of epoxy over the PZT coupon and a large drop over the ASIC. Using a clean needle, push the droplet over the board so that the entire topside of the board is coated. The epoxy should wet the board, but not spill over due to its surface tension. Once the main body of the board is coated, the vias should also be coated, as well as the side faces of the piezo. The board can then be cured in a UV chamber for roughly 5 minutes. It has been found that the test wires can occasionally contact something in the UV chamber and short the ASIC. Thus, prior to putting the board in the chamber, it is good to wrap the wires down or place it on some tape in order to isolate them from any chamber surfaces.

Following curing, the backside should be coated. In particular the exposed PZT coupon which hangs over the board as well as the backside of the test vias and the two vias on the backside of the board which connect the electrodes to the topside of the board. This part can be a little tricky due to the small space between the backside vias and the electrodes, so it is best to start with a very small amount of epoxy and place it near the edge of the board, then drag the epoxy up towards the vias. The backside of the board should be cured in the same manner as the topside. Once the board is fully encapsulated, a final electrical test should be done, and upon passing, the implantable device is now complete.

Example 2—Set-Up for Testing Implantable Devices

Testing of implantable has always been tricky due to the thinness of the test leads that extend out from the board.

Clipping onto and off of these vias for I-V measurements has often resulted in pulling the leads off the body of the device. Furthermore, due to the test leads, it is difficult to perform water-tank test measurements; as exposed electronics in water would result in shorts. In order to circumvent this issue, a PCB was designed to serve as a testbed for implantable device measurements. The PCB (Bay Area Circuits, Fremont, Calif.) was made of FR-4 and 60 mil thick; it includes four vias, distributed on the board to match the layout of the version two implantable device boards.

Gold header pins (Pin Strip Header, 3M, Austin, Tex.) were soldered into the vias so that they extended from the board on both sides of the board. This enabled us to place our devices onto the test bed, and tap into the implantable by accessing the header pins. Next, to insulate the vias, plastic caps made out of polyethylene terephthalate (PETG) were 3D printed (Flashforge Creator X, FlashForge, Jinhua, China). These caps were printed with a groove so that an O-ring could be placed inside the groove and create a waterproof seal around the header pins. The caps were connected to the board and compression was created by drilling 2 mm holes through the PCB and cap using a micro-mill (47158, Harbor Freight, Camarillo, Calif.) and screwing the cap and board together. Wires extending from the testbed were soldered to the header pins and the pins were then encapsulated. To measure the effectiveness of the seal, the boards were submerged in an aqueous 6 M NaCl solution and the resistance between the pins was measured using a Keithley 2400. A MATLAB script was written to automatically record and plot the resistance over time. A drop in the resistance would indicate that the seal was broken. As an additional test, a piece of litmus paper was also put under the plastic cap with the intention that if the cap leaked, the litmus paper would change color. The pins were encapsulated using the same medical grade epoxy used to encapsulate the implantable device boards, and parylene was deposited over the epoxy on the back side of the testboards for a completely waterproof barrier. The resistance between the two neighboring pins of the testbed submerged in salt water solution as a function of time for only epoxy insulation and epoxy plus parylene insulation was measured. Without a parylene barrier, the epoxy began to leak, allowing salt water to short out the pins of the testbed.

Example 3—Implantable Devices Encapsulated in Silicon Carbide

Rather than an epoxy encapsulant, silicon carbide (SiC) may be a more effective material for insulating and protecting the implantable device. SiC is formed by the covalent bonding of Si and C, forming tetrahedrally oriented molecules with short bond length and thus, high bond strength, imparting high chemical and mechanical stability. Amorphous SiC (a-SiC) has been welcomed by the biomedical community as a coating material as it can be deposited at much lower temperatures than ordinarily required by crystalline SiC and is an electrical insulator. Deposition of a-SiC is generally performed via plasma enhanced chemical vapor deposition (PECVD) or sputtering. Ongoing research using sputtered a-SiC has shown that it is difficult to achieve a pinhole free layer of SiC. Rather, PECVD using $SiH_4$ and $CH_4$ as precursors is capable of yielding impressive, pinhole free SiC films.

Furthermore, implanted a-SiC has shown impressive biocompatibility. Previous studies have shown that a 50 µm iridium shaft coated with a-SiC implanted in the rabbit cortex for ~20 days did not show the usual chronic inflammatory response of macrophage, lymphocyte, monocyte recruited to the insertion site. See Hess et al., *PECVD silicon carbide as a thin film packaging material for microfabricated neural electrodes*, Materials Research Society Symposium Proceedings, vol. 1009, doi: 10.1557/PROC-1009-U04-03 (2007).

Figure 18:
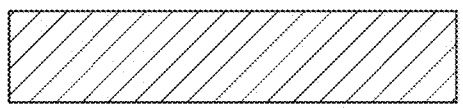
FIG. 18 illustrates a schematic for encapsulating an implantable device in silicon carbide.
Figure 18:
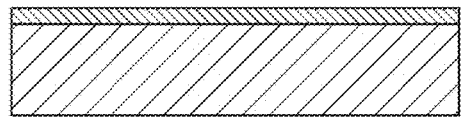
Figure 18:
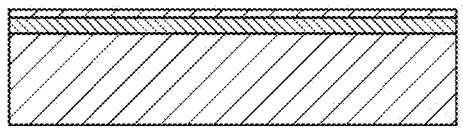
Figure 18:
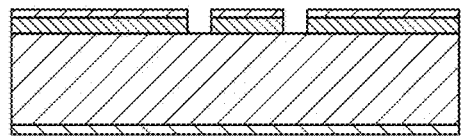
Figure 18:
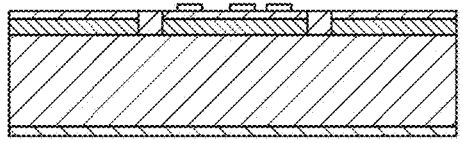
Figure 18:
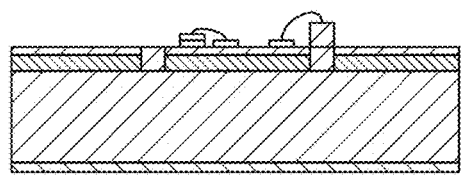
Figure 18:
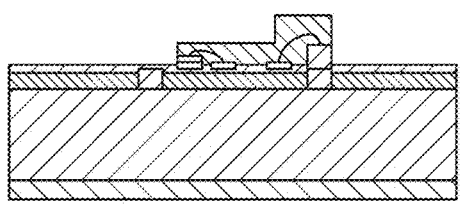
Figure 18:
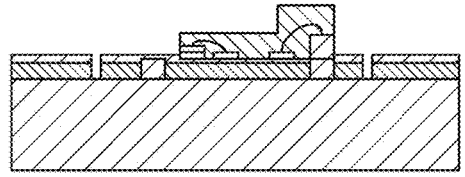
Figure 18:

It is interesting to consider an approach to implantable devices that would involve constructing the devices on silicon with a silicon carbide encapsulant for a truly chronic implant. A possible process is shown in FIG. 18. One of the largest challenges here is ensuring that the PECVD of SiC dues not depole the piezoelectric material. In order to have contamination-free films, it is important to deposit at a minimum temperature of 200° C., but below the Curie temperature of the piezoelectric transducer.

Example 4—Power Transfer to and Backscatter of a Miniaturized Ultrasonic Transducer A set of experiments were carried out with PZT due to the relative ease of obtaining PZT crystals with varying geometry. Metalized PZT sheets of several thicknesses were obtained (PSI-5A4E, Piezo Systems, Woburn, Mass. and PZT 84, APC Internationals, Mackeyville, Pa.), with a minimum PZT thickness of 127 µm. The PZT was fully encapsulated in PDMS silicon for biocompatibility.

The most commonly used method to dice PZT ceramics is to use a wafer dicing saw with an appropriate ceramic blade to cut PZT sheets into individual PZT crystals. The minimum resolution of the cut is determined by the kerf of the blade and can be as small as 30 µm.

Another possible option is to use a laser cutter. Unlike the dicing saw, laser cutting realizes the cuts by focusing a high-power laser beam onto a material, which melts, vaporizes, removes, and scribes the piece. The precision of laser cutting can be down to 10 µm and is limited by the wavelength of the laser. However, for treating sensitive samples such as PZT ceramics, the temperature at the site of cuts can be damaging to the piezoelectric performance of the material. Excimer laser cutting of ceramics uses UV laser to cut with excimer from noble gases, but such laser cutter is extremely expensive and no suitable services are currently available. As a result, a dicing saw was used to perform all the cuts.

In order to drive or extract electrical energy from the PZT, an electrical connection is made to both the top and bottom plates. The materials typically used as an electrode for PZT are silver or nickel. Silver is generally used for a wide variety of non-magnetic and AC applications and silver in the form of flakes suspended in a glass frit is usually screened onto the ceramic and fired. For high electric field DC applications, silver is likely to migrate and bridge the two plates. As a result, nickel, which has good corrosion resistance and does not electro-migrate as readily can be electroplated or vacuum deposited as an alternative.

Both materials can be soldered onto with the appropriate solder and flux. For instance, silver is soluble in tin, but a silver loaded solder can be used to prevent scavenging of silver in the electrode. Phosphor content from the nickel plating can make soldering tricky, but the correct flux can remove surface oxidation. However, when soldering, in order to avoid exceeding the Curie point and depoling the PZT sample, the soldering temperature must be between 240 and 300° C. Even at these temperatures, since the PZT is also pyroelectric, one must be careful not to exceed 2-4 seconds of soldering time.

Alternatively, an electrical connection can be made using either silver epoxy or low temperature soldering using solder paste. Standard two-part silver epoxy can provide a sufficient electrical conductivity and can be cured even at room temperature overnight. However, the joints tend to be fragile and can easily break during testing. The bond can be reinforced by using a non-conductive epoxy as an encapsulation but this additional layer presents a mechanical load to the PZT and can significantly dampen its quality factor. Low-temperature solder paste on the other hand undergoes a phase change between the temperature of 150 and 180° C. and can provide great electrical connection and a bond strength that is comparable to that achieved with flash soldering. Therefore, the low-temperature soldering approach was used.

Wafer dicing is capable of cutting PZTs into small crystals of 10's of µm. However, samples that are smaller than 1 mm in dimension are extremely difficult to handle with tweezers and bond to. In addition, due to the variation in the length of wire used to interface with top and bottom plates of PZT crystals (and therefore parasitic inductance and capacitance introduced by the wire) and the amount of solder paste dispensed across a number of samples, the impedance spectroscope measurements were inconsistent.

Figure 19:
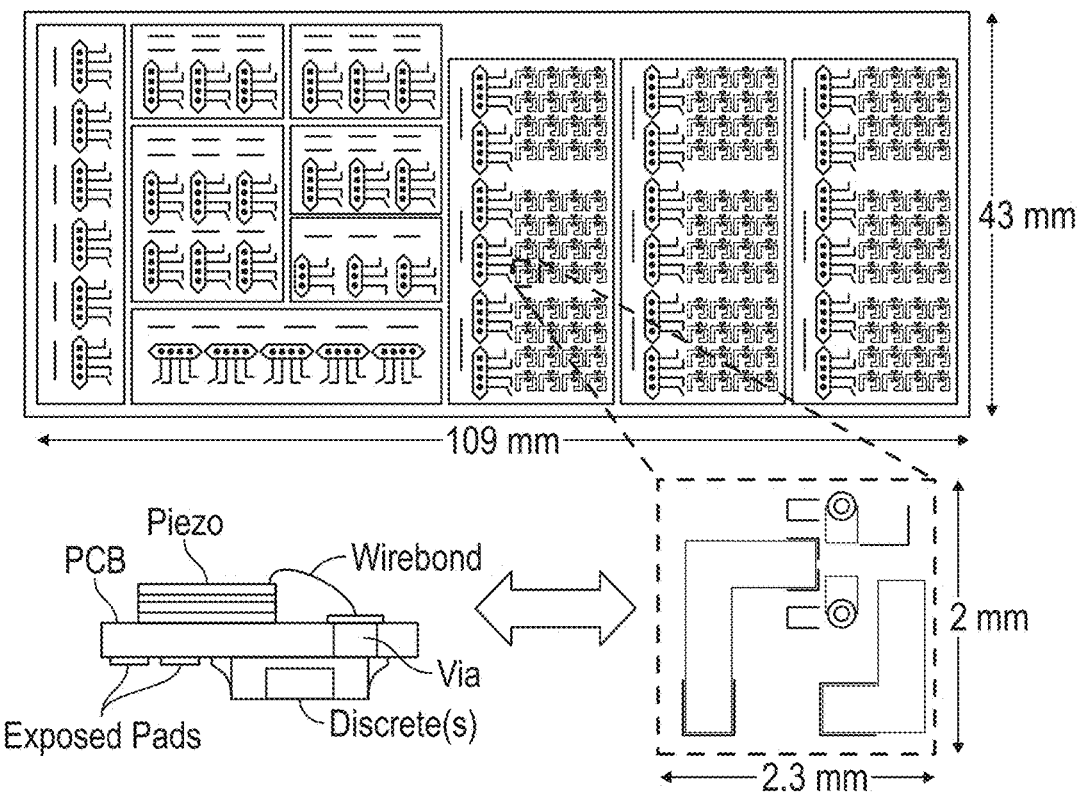
FIG. 19 shows an assembly prototype schematic and PCB.

Therefore, a 31 mil thick two-layer FR-4 PCB where all of the electrical interconnects short and de-embed out the parasitics from the wires and the board was fabricated. The fabricated board, which includes numerous test structures and a module for individually characterizing 127 µm, 200 µm, and 250 µm thick PZT crystals are shown with dimensions in FIG. 19. Each unit cell in the test module contains two pads with specified dimensions on one side of the PCB to interface with the PZT crystals and pads for discrete components for backscattering communication on the opposite side. The pitch between the unit cells is limited by the size of the discrete components and is roughly 2.3 mm×2 mm.

Figure 20A:
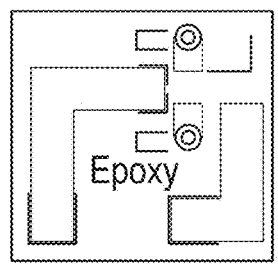
FIG. 20A-E show processing steps to ensure that the desired miniaturized ultrasonic transducer (PZT) dimension is assembled on the PCB. At FIG. 20A, epoxy solder paste is dispensed onto the board. At FIG. 20B, a piezoelectric material is attached to the PCB. At FIG. 20C, the piezoelectric material is diced to form a bulk piezoelectric ultrasonic transducer of the desired size. At FIG. 20D, the ultrasonic transducer is wirebonded to the PCB. At FIG. 20E, the PCB and ultrasonic transducer is encapsulated in PDMS.
Figure 20B:
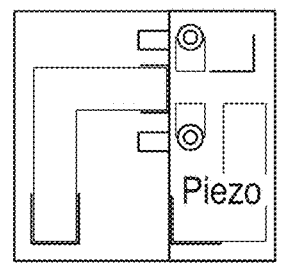
Figure 20C:
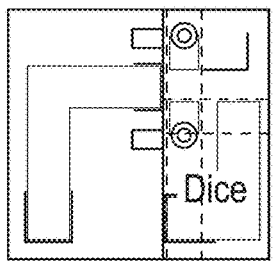
Figure 20D:
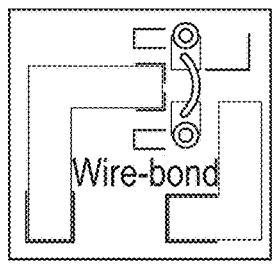
Figure 20E:
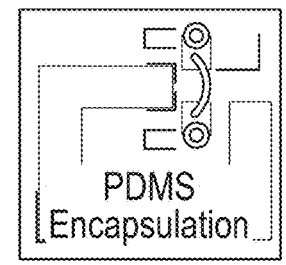

In order to avoid directly handling tiny PZT crystals, FIGS. 20A-E outline a scalable process flow to bond PZT onto the PCB. As shown in FIG. 20A, the solder paste is dispensed using a pump at a constant pressure and for a controlled amount of time on one of the pads on the top side. The pads are either 250 µm$^2$, 200 µm$^2$, or 127 µm$^2$ based on the thickness of the PZT used. FIG. 20B shows a PZT piece larger than the pad (that can be easily handled) is placed on top to cover the pads. The board and piezo assembly are baked in an oven to cure the solder paste. Therefore, PZT crystals are now bonded to pre-soldered bumped electrodes. FIG. 20C shows a wafer dicing saw makes a total of four cuts along the edges of the pad with the solder paste using alignment markers on the board, with non-bonded areas dropping off and leaving an array of small PZT crystals bonded to the PCB. FIG. 20D shows single wirebond makes an electrical contact between the top plate of the PZT and an electrode on the PCB, completing the circuit. Finally, FIG. 20E shows the entire assembly is encapsulated in PDMS (Sylgard 184, Dow Corning, Midland, Mich.) to protect the wirebond and provide insulation.

Since piezoelectric material is an electro-mechanical structure, its electrical and mechanical properties were characterized. The following details the test setup and techniques to perform such measurements.

Any electrical device can be modeled as a black box using a mathematical construct called two-port network parameters. The properties of the circuits are specified by a matrix of numbers and the response of the device to signals applied to its input can be calculated easily without solving for all the internal voltages and currents in the network. There are several different types of two-port network parameters, such as Z-parameters, Y-parameters, S-parameters, and ABCD-parameters, etc. and the conversion between different parameters can be easily derived. The apparatus that enables us to extract these parameters is called a vector network analyzer (VNA). A VNA incorporates directional couplers to decompose the voltage in each port into incident and reflected waves (based on impedance mismatching), and calculate the ratio between these waves to compute scattering or S-parameters.

Figure 21:
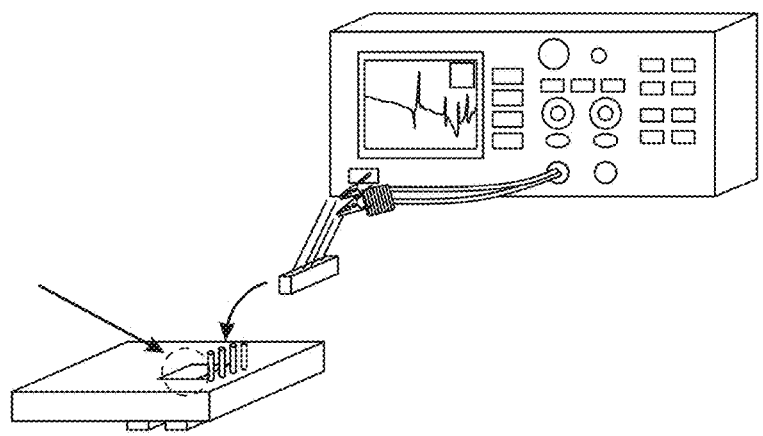
FIG. 21 shows a schematic for measuring electrical impedance with a vector network analyzer (VNA).

Before performing measurements using a VNA, one must calibrate the instrument since the internal directional couples are non-ideal. Calibration also allows us to move the reference plane of the measurement to the tips of the cable, i.e., calibrate out parasitics from the cable. There are several calibration standards but the most commonly used is open, short, and load calibration procedures. The measurement schematic is shown in FIG. 21. Alligator clips, which are soldered onto the ends of the coaxial cable, are used to interface with the top/bottom plates. The parasitics from the clips were not significant below 100 MHz.

As an example, a VNA (E5071C ENA, Agilent Technologies, Santa Clara, Calif.) was used to measure the electrical properties of a (250 µm)$^3$ PZT crystal. It was noted that the measured capacitance of the PZT crystal vastly differs from the capacitance expected from a simple parallel-plate capacitance model due to significant parasitic capacitances from the PCB and the fixture (clip and connector). Since the VNA coefficients from the calibration step previously outlined only moved the measurement plane to the tips of the cable, open/short/load calibration structures fabricated on the same board were used to include the board and fixture parasitics. The measured PZT response matched the expected response after calibration.

Figure 22A:
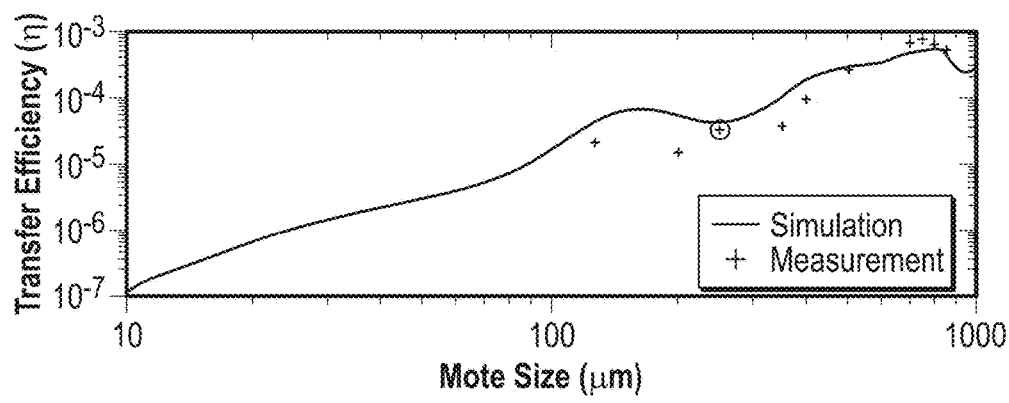
FIG. 22A shows that the measured power transfer efficiency at various bulk piezoelectric ultrasonic transducer sizes matches simulated behavior.
Figure 22B:
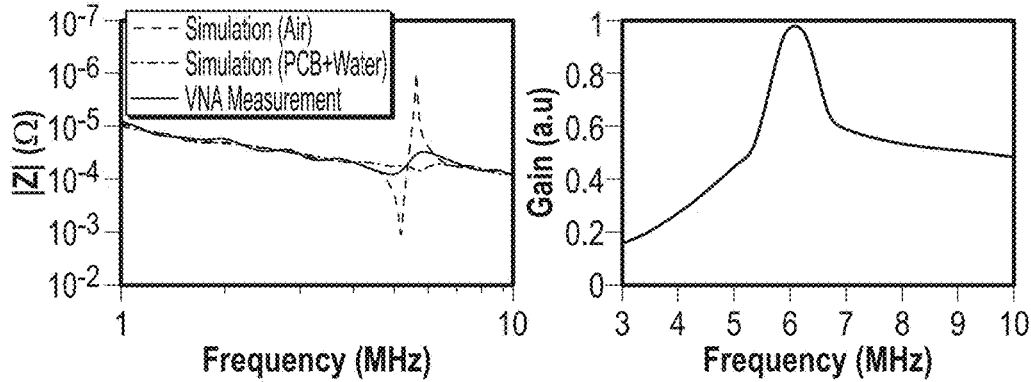
FIG. 22B shows that the measured impedance spectroscopy of a PZT crystal matches a simulation.

Using this calibration technique, the impedance of the PZT can be plotted as a function of frequency, as shown in FIG. 22B. From this plot, however, it is extremely difficult to determine whether there is any electro-mechanical resonance. When the simulation result with air backing (no mechanical clamping) was overlaid, it was noticed that the impedance spectroscopy matches well with the measurement at low and high frequencies, with the exception of noticeable peak at resonant frequency of roughly 6 MHz and its harmonics. Upon clamping and loading one side of PZT with PCB (FR-4), it was seen that a significant dampening of the resonant peaks from air backing. Despite a lack of observable resonance in the measurement, a small blimp around 6 MHz was observed, and the mechanical quality factor $Q_m$ can be calculated using the following equations, $$Q_m = \frac{f_a^2}{2Z_rC_p(f_a^2 - f_r^2)}$$

where $f_a$ and $f_r$ represent anti-resonant (where impedance is maximized) and resonant frequency (where impedance is minimized), $Z_r$ represents an impedance at resonance, and $C_p$ is the low-frequency capacitance. The calculated quality factor from the measurement is roughly 4.2 compared to 5.1 in simulation. According to the datasheet, the unloaded Q of the PZT is ~500, indicating that FR-4 backing and wirebonds are causing significant degradation of the quality factor. Despite the drastic reduction in the mechanical Q of the PZT crystals, experiments showed that the backscattered signal level only decreased by roughly ~19.

In the electrical characterization setup, the VNA has a built-in signal generator to provide the input necessary for characterization. In order to perform acoustic characterization of PZT, acoustic waves were generated and launched onto the sample to use as an input. This can be achieved with commercially available broadband ultrasonic transducers.

Figure 23:
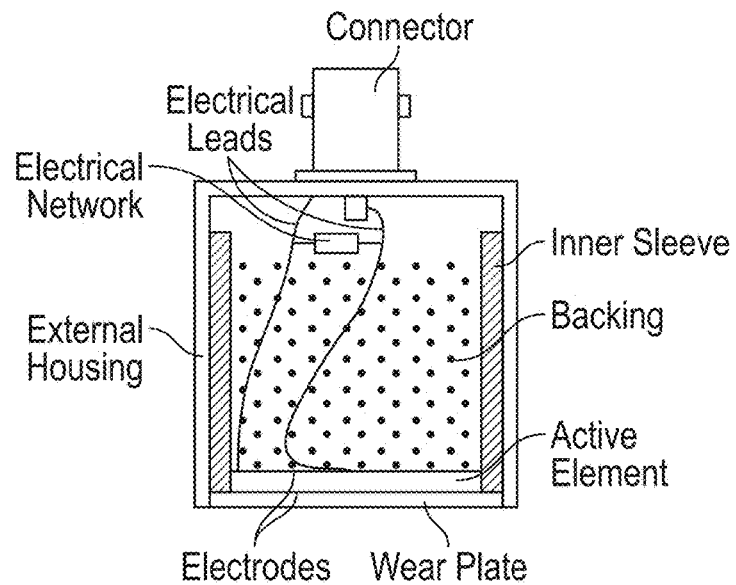
FIG. 23 is a schematic of an exemplary ultrasonic transducer that can be used as part of an interrogator.

FIG. 23 shows the composition of a representative transducer, which consists of a piezoelectric active element, backing, and wear plate. The backing is usually made from a material with high attenuation and high density to control the vibration of the transducer by absorbing the energy radiating from the back face of the active element while the wear plate is used to protect the transducer element from the testing environment and to serve as a matching layer.

Figure 24:
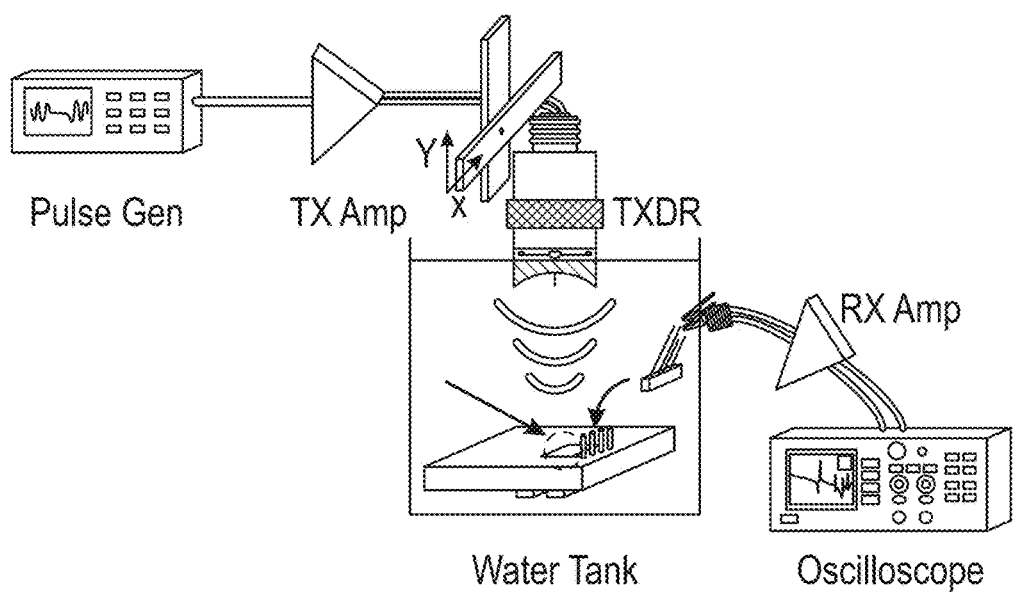
FIG. 24 is a schematic of a setup for acoustic characterization with a calibrated ultrasonic transducer for power delivery verification. The ultrasonic wave receiver is separate from the ultrasonic wave transmitter.

Ultrasonic power transfer tests were performed using the home-built setup shown in FIG. 24. A 5 MHz or 10 MHz single element transducer (6.3 mm and 6.3 mm active area, respectively, ~30 mm focal distance, Olympus, Waltham, Mass.) was mounted on a computer-controlled 2-axis translating stage (VelMex, Bloomfield, N.Y.). The transducer output was calibrated using a hybrid capsule hydrophone (HGL-0400, Onda, Sunnyvale, Calif.). Assembly prototypes were placed in a water container such that transducers could be immersed in the water at a distance of approximately 3 cm directly above the prototypes. A programmable pulse generator (33522B, Agilent Technologies Santa Clara, Calif.) and radio frequency amplifier (A150, ENI, Rochester, N.Y.) were used to drive transducers at specified frequencies with sinusoidal pulse trains of 10-cycles and a pulse-repetition frequency (PRF) of 1 kHz. The received signals were amplified with a radio frequency amplifier (BT00500-AlphaS-CW, Tomco, Stepney, Australia), connected to an oscilloscope (TDS3014B, Tektronix, Beaverton Oreg.) to collect ultrasound signal and record them using MATLAB.

Figure 25A:
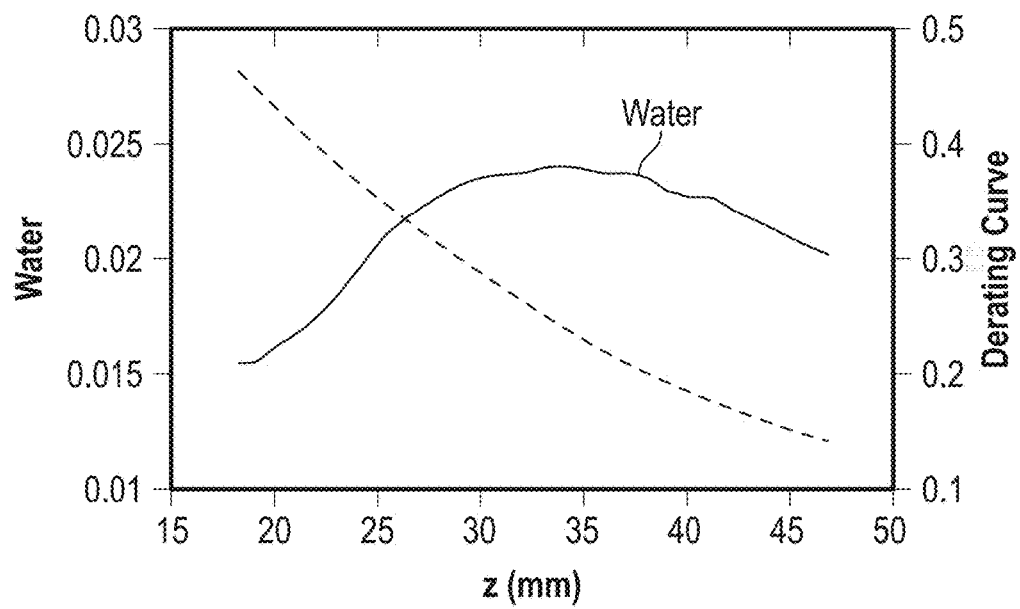
FIG. 25A shows the output power of a 5 MHz transducer as the hydrophone is moved away from the transducer's surface.
Figure 25B:
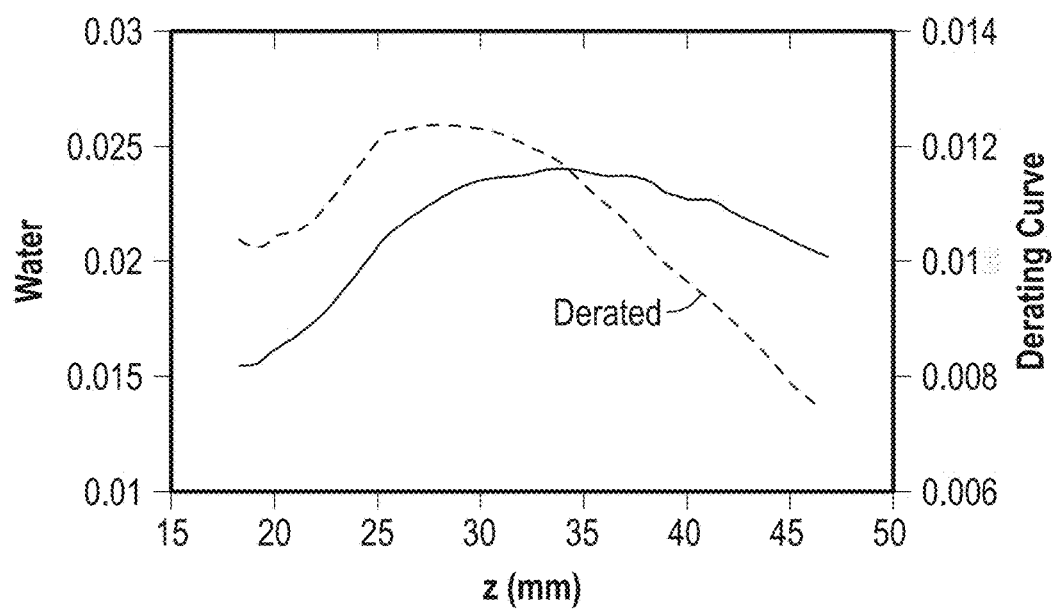
FIG. 25B shows that the de-rated peak is shifted to the left in relation to the water peak.
Figure 26A:
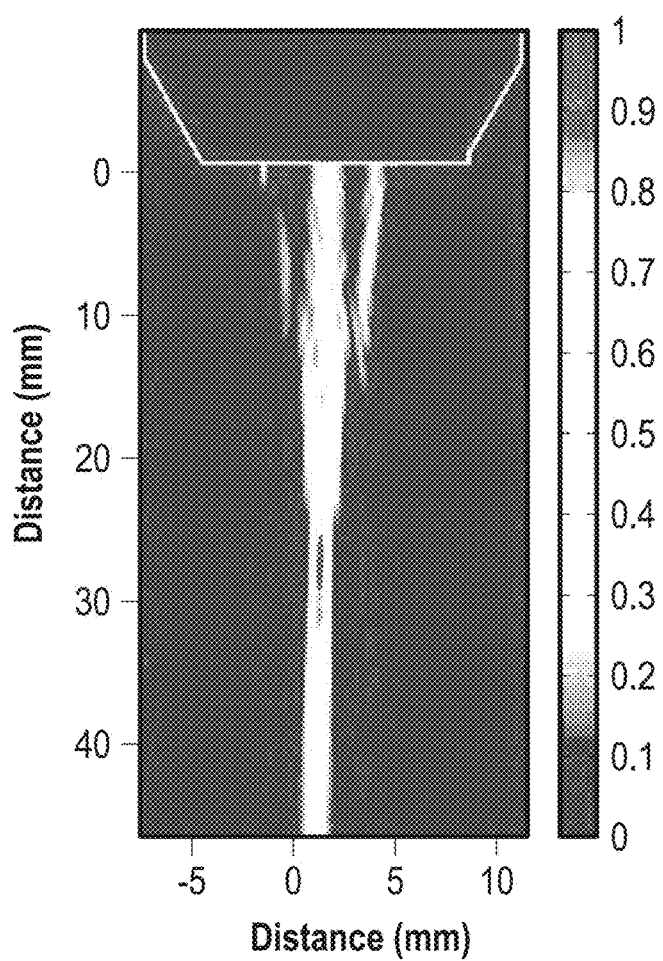
FIG. 26A shows the XZ cross-section of the transducer output, illustrating a Rayleigh distance and a clear transition from the near-field to far-field propagation.
Figure 26B:
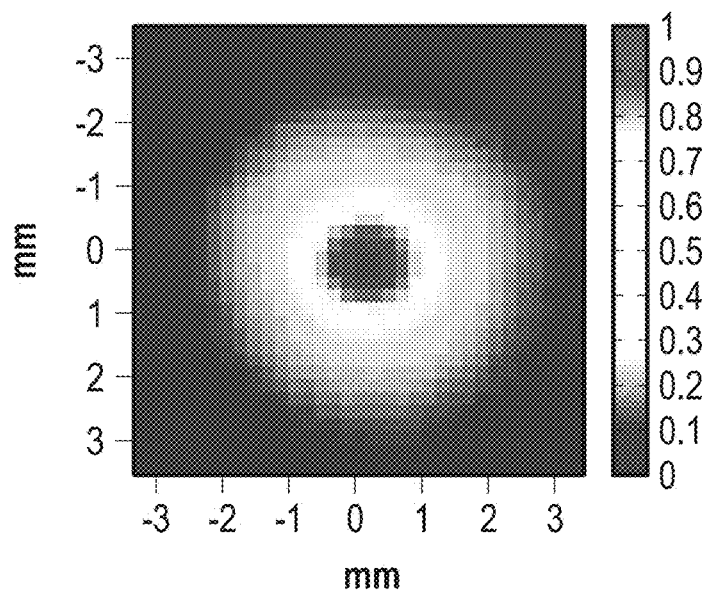
FIG. 26B shows the XY beam cross-section showing a 6 dB bandwidth of the beam at 2.2 mm.

FIG. 25A and FIG. 25B show a representative measurement of the output power of the 5 MHz transducer as a function of the distance between the surface of the transducer and the hydrophone (z-axis). The peak pressure in water was obtained at ~33 mm away from the transducer's surface (FIG. 25A), while the de-rated peak (with 0.3 dB/cm/MHz) was at ~29 mm (FIG. 25B). FIG. 26A shows the de-rated XZ scan of the transducer output, which show both near-field and far-field beam patterns and a Rayleigh distance or a focal point at ~29 mm, matching the de-rated peak in FIG. 25B. FIG. 26B shows a XY cross-sectional scan of the beam at the focal point of ~29 mm, where the 6 dB beamwidth measured roughly 2.2 mm.

The total integrated acoustic output power of the transducer at various frequencies over the 6 dB bandwidth of the beam was nominally kept at a spatial-peak temporal-average $I_{SPTA}$ of 29.2 µW/cm², resulting in a total output power of ~1 µW at the focal point, with a peak rarefaction pressure of 25 kPa and a mechanical index (MI) of 0.005. Both the de-rated $I_{SPTA}$ and MI were far below the FDA regulation limit of 720 mW/cm² and 1.9, respectively (FDA 2008).

FIG. 22A shows the measured power delivery efficiency of the fully assembled prototype with cable loss calibrated out for various neural dust node sizes as compared to analytical predictions made for this same setup. Measured results matched the simulated model behavior very closely across all transducer sizes, with the exception of a few smaller transducer dimensions, likely due to the sensitivity to transducer position and the ultrasound beamwidth. The measured efficiency of the link for the smallest PZT crystal (127 µm)³ was 2.064×10⁻⁵, which resulted in 20.64 pW received at the transducer nominally. A maximum of 0.51 µW can be recovered at the transducer if the transmit output power density was kept at 720 mW/cm². Such low power level harvested by the PZT is mainly due to the extreme inefficiency of broadband transducers that were used for the experiments; dedicated, custom-made transducers at each transducer dimension with optimal electrical input impedance could result in more than 2 orders of magnitude improvement in the harvested power level as predicted by the simulation model.

Figure 22C:
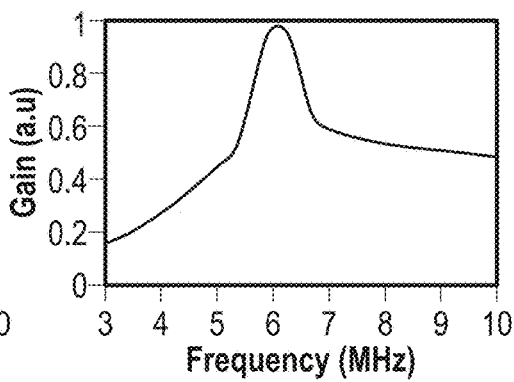
FIG. 22C show that the frequency response of harvested power of the miniaturized ultrasonic transducer is approximately 6.1 MHz.

The frequency response of electrical voltage harvested on a (250 µm)³ PZT crystal is shown in FIG. 22C. The resonant frequency was measured to be at 6.1 MHz, which matches the shift in the resonant frequency predicted for a cube due to Poisson's ratio and the associated mode coupling between resonant modes along each of the three axes of the cube. Furthermore, the calculated Q of 4 matched the electrically measured Q of the PZT.

The experimental result indicate that the analytical model for power coupling to very small PZT nodes using ultrasound is accurate down to at least ~100 µm scale and likely lower. It remains to be seen just how mall a transducer can be fabricated before loss of function. Note that measurements of even smaller nodes (<127 µm) were limited not by the prototype assembly process but by commercial availability of PZT substrates. Moving forward, the considerable volume of research and techniques that has gone into micro- and nanoelectromechanical RF resonators was be used (see Sadek et al., *Wiring nanoscale biosensors with piezoelectric nanomechanical resonators*, Nano Lett., vol. 10, pp. 1769-1773 (2010); Lin et al., *Low phase noise array-composite micromechanical wine-glass disk oscillator*, IEEE Elec. Dev. Meeting, pp. 1-4 (2005)) and thin-film piezoelectric transducer (see Trolier-McKinstry et al., *Thin film piezoelectrics for MEWS*, J. Electroceram., vol. 12, pp. 7-17 (2004)) to facilitate extremely small (10's of µm) transducers and to truly assess the scaling theory.

Example 5—Beamforming Using Interrogator Ultrasonic Transducer Array

In this example, an ultrasonic beamforming system capable of interrogating individual implantable sensors via backscatter in a distributed, ultrasound-based recording platform is presented. A custom ASIC drives a 7×2 PZT transducer array with 3 cycles of 32V square wave with a specific programmable time delay to focus the beam at the 800 µm neural dust mote placed 50 mm away. The measured acoustic-to-electrical conversion efficiency of the receive mote in water is 0.12% and the overall system delivers 26.3% of the power from the 1.8V power supply to the transducer drive output, consumes 0.75 µJ in each transmit phase, and has a 0.5% change in the backscatter per volt applied to the input of the backscatter circuit. Further miniaturization of both the transmit array and the receive mote can pave the way for a wearable, chronic sensing and neuromodulation system.

In this highly distributed and asymmetric system, where the number of implanted devices outnumbers the interrogating transceivers by an order of magnitude, beamforming can be used to efficiently interrogate a multitude of implantable devices. Research into beamforming algorithms, trade-offs, and performance in the implantable device platform has demonstrated that cooperation between different interrogators is useful for achieving sufficient interference suppression from nearby implantable devices. See Bertrand et al., *Beamforming approaches for untethered ultrasonic neural dust motes for cortical recording: a simulation study*, IEEE EMBC, 2014, pp. 2625-2628 (August 2014). This example demonstrates a hardware implementation of an ultrasonic beamforming system for the interrogator and implantable device system shown in FIG. 2A. The ASIC (see, e.g., Tang et al., *Integrated ultrasonic system for measuring body fat composition*, 2015 IEEE International Solid-State Circuits Conference—(ISSCC) Digest of Technical Papers, San Francisco, Calif., 2015, pp. 1-3 (February 2015); Tang et al., *Miniaturizing Ultrasonic System for Portable Health Care and Fitness*, IEEE Transactions on Biomedical Circuits and Systems, vol. 9, no. 6, pp. 767-776 (December 2015)), has 7 identical channels, each with 6 bits of delay control with 5 ns resolution for transmit beam-forming, and integrates high-voltage level shifters and a receive/transmit switch that isolates any electrical feed-through.

The ASIC operates with a single 1.8V supply and generates a 32V square wave to actuate piezoelectric transducers using integrated charge pumps and level shifters. The system delivers ~32.5% of the power from the 1.8V supply to the 32V output voltage and ~81% from 32V to the output load (each transducer element is 4.6 pF). The ASIC block diagram is shown in FIG. 2A; the circuit details to enable such low energy consumption per measurement can be found in Tang et al., *Integrated ultrasonic system for measuring body-fat composition*, 2015 IEEE International Solid-State Circuits Conference—(ISSCC) Digest of Technical Papers, San Francisco, Calif., 2015, pp. 1-3 (February 2015). The ASIC is fabricated in 0.18 μm CMOS with high voltage transistors. The chip area is 2.0 mm² and includes the complete system except for the digital controller, ADCs, and two off-chip blocking capacitors.

The design of a transducer array is a strong function of the desired penetration depth, aperture size, and element size. Quantitatively, the Rayleigh distance, R, of the array can be computed as follows:

$$R = \frac{D^2}{4\lambda}$$

where D is the size of the aperture and λ is the wavelength of ultrasound in the propagation medium. By definition, Rayleigh distance is the distance at which the beam radiated by the array is fully formed; in other words, the pressure field converges to a natural focus at the Rayleigh distance and in order to maximize the received power, it is preferable to place the receiver at one Rayleigh distance where beam spreading is the minimum.

The frequency of operation is optimized to the size of the element. A preliminary study in a water tank has shown that the maximum energy efficiency is achieved with a (800 μm)³ PZT crystal, which has a resonant frequency of 1.6 MHz post-encapsulation, resulting in λ~950 μm. The pitch between each element is chosen to be an odd multiple of half wavelength in order to beamform effectively. As a result, for this demonstration of beamforming capabilities, the overall aperture is ~14 mm, resulting in the Rayleigh distance of 50 mm. At 50 mm, given the element size of 800 μm, each element is sufficiently far from the field (R=0.17 mm); therefore, the beam pattern of an individual element should be omni-directional enough to allow beamforming.

There are several transmit and receive beamforming techniques that can be implemented. In this example, time delay-and-sum transmit beamforming algorithm is chosen, such that the signals constructively interfere in the target direction. This algorithm is capable of demonstrating beam-steering and maximal power transfer to various implantable devices. In order to accommodate backscatter communication to multiple implantable devices simultaneously, more sophisticated algorithms may be required. These can include delay-and-sum beamforming, linearly constrained minimum-variance beamforming, convex-optimized beamforming for a single beam, 'multicast' beamforming w/convex optimization, maximum kurtosis beamforming, minimum variance distortionless response robust adaptive beamforming, polyadic tensor decomposition, and deconvolution of mote impulse response from multi-Rx-channel time-domain data. The detailed treatment of one aspect of this problem is described in Bertrand et al., *Beamforming approaches for untethered ultrasonic neural dust motes for cortical recording: a simulation study*, IEEE EMBC, 2014, pp. 2625-2628 (August 2014).

Each of the 7 channels is driven by 3 cycles of 32V square wave with a specific programmable time delay such that the energy is focused at the observation distance of 50 mm. The time delay applied to each channel is calculated based on the difference in the propagation distance to the focus point from the center of the array and the propagation speed of the ultrasound wave in the medium.

Ultrasim was used to characterize the propagation behavior of ultrasound wave in water with the 1D array described above. Simulated XY (FIG. 27A) and XZ (FIG. 27B) cross-sectional beam patterns closely match the measurement as shown, despite not modeling the PDMS encapsulation.

Water is used as the medium for measuring the beamforming system as it exhibits similar acoustic properties as the tissue. Pre-metalized Lead Zirconate Titanate (PZT) sheets (APC International, Mackeyville, Pa.) are diced with a wafer saw to 800 μm×800 μm×800 μm crystals (parallel capacitance of 4.6 pF each), which is the size of each transmit element. Each PZT element is electrically connected to the corresponding channel in the ASIC by using a conductive copper foil and epoxy for the bottom terminal and a wirebond for the top terminal. The array is encapsulated in PDMS (Sylgard 184, Dow Corning, Midland, Mich.) to protect the wirebond and provide insulation. The quality factor of the PZT crystal post encapsulation is ~7. The array is organized into 7 groups of 2×1 elements, with the pitch of ~5/2λ~2.3 mm. The array measures approximately 14 mm×3 mm. Finally, the entire assembly is encased in a cylindrical tube with the diameter of 25 mm and the height of 60 mm and the tube is filled with water.

The transducer array's 2D beam pattern and output are calibrated using a capsule hydrophone (HGL-0400, Onda, Sunnyvale, Calif.). The hydrophone is mounted on a computer-controlled 2D translating stage (VelMex, Bloomfield, N.Y.). The hydrophone has an acceptance angle (−6 dB at 5 MHz) of 30°, which is sufficient to capture the beam given the transmission distance of 50 mm and the scan range (±4 mm).

Figure 27A:
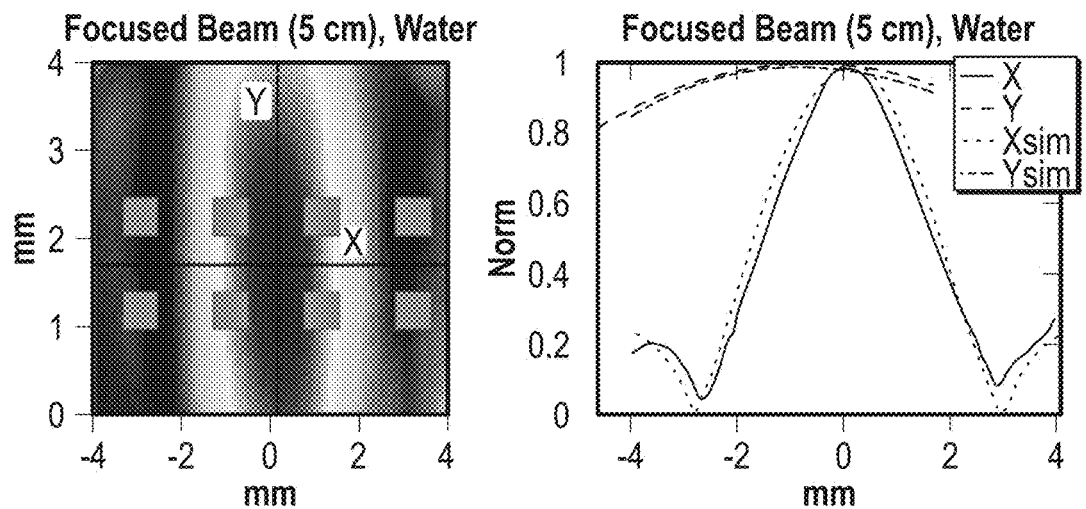
FIG. 27A shows a focused 2D beam pattern from a transducer array in the XY plane. The measured beam approximates the simulated beam in both the X and Y dimensions.
Figure 27B:
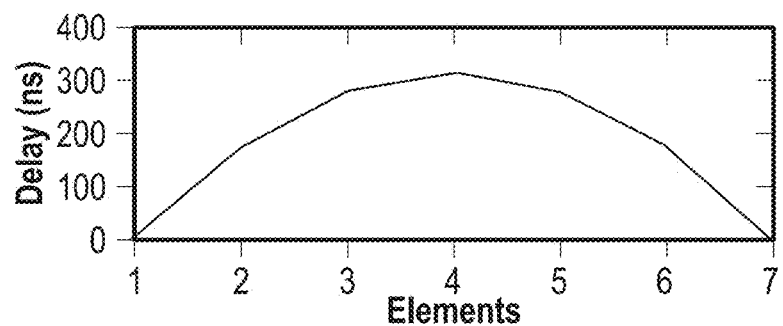
FIG. 27B shows the delay time applied to each transducer element in the ultrasonic transducer array.
Figure 27C:
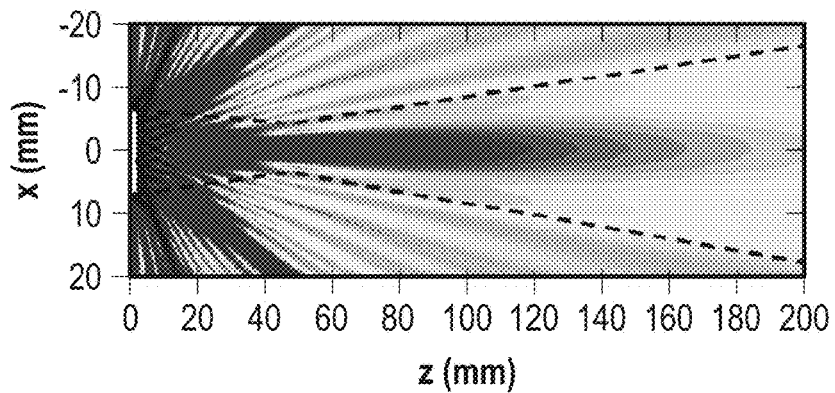
FIG. 27C shows a simulated 2D XZ cross-sectional beam pattern.

The measured XY cross-sectional beam pattern with the overlay of the array is shown in FIG. 27A. The applied delay for each transducer in the array (element) is shown in FIG. 27B. The −6 dB beamwidth at the focal point is 3.2 mm~3λ. The flexibility of the ASIC allows for both wide and granular programming of the delays. The peak pressure level of the array at 50 mm before and after beamforming is ~6 kPa and ~20 kPa, respectively. The 3× in the transmitted output pressure wave after beamforming matches the simulation. The simulation also verifies that the Rayleigh distance of the array is at 50 mm as shown in FIG. 27C.

Figure 28A:
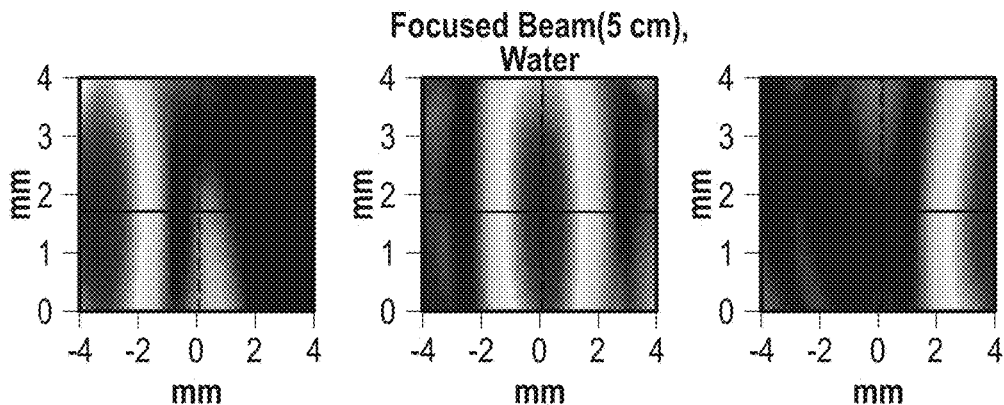
FIG. 28A shows beam steering of an ultrasonic wave beam transmitted from a transducer array. Underneath each beam pattern is the delay for each transducer in the array to obtain the measured beam pattern, as shown in FIG. 28B.
Figure 28B:
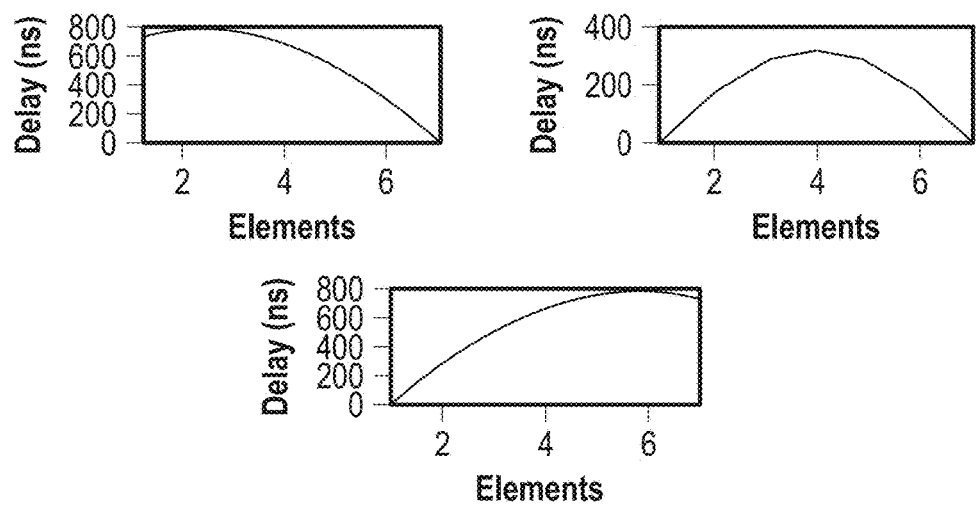
FIG. 28C shows the 1D beam pattern in the X-axis for each beam pattern shown in FIG. 28A. The measured beam pattern closely approximates the simulated beam pattern.
Figure 28C:
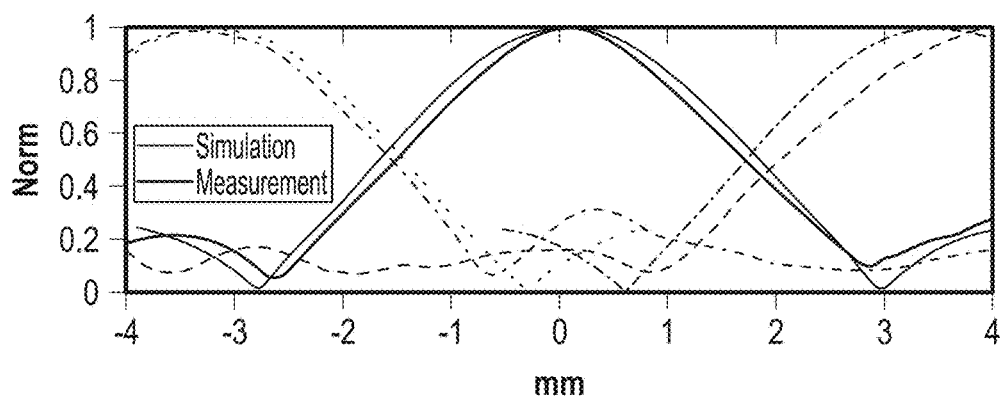

Additionally, in order to verify the capability to interrogate multiple implantable devices, it was verified verified the beam steering capability of the array as shown in FIG. 28A (showing beam steering at three different positions in the XY-plane), with the time delay for each beam position shown underneath in FIG. 28B. The 1D beam steering matches very closely with the simulation, as shown in FIG. 28C. Note that the beam steering range is limited to ±4 mm due to the mechanical construct of the array, rather than the electronic capability.

The hydrophone is replaced with an implantable device (with a 800 µm×800 µm×800 µm bulk piezoelectric transducer) and placed at the transmission distance of 50 mm to verify the power link. The open-circuit peak-to-peak voltage measured at the mote is 65 mV, for a transmit pulse-duration of 2.56 µs. The spatial peak average acoustic power integrated over the −6 dB beamwidth at the focal point is 750 µW, which is 0.005% of the FDA safety limit. The maximum harvestable power at the mote is 0.9 µW, resulting in the measured acoustic-to-electrical conversion efficiency of 0.12%. The measured result is in agreement with the link model (see Seo et al., *Model validation of untethered ultrasonic neural dust motes for cortical recording*, J. Neurosci. Methods, vol. 244, pp. 114-122 (2015)). The system delivers 26.3% of the power from the 1.8V power supply to the transducer drive output (defined as driving efficiency) and consumes 0.75 µJ in each transmit phase.

The ultrasonic backscatter communication capability of the system is verified by measuring the difference in the backscattered voltage level as the input to the backscatter circuit (see Seo et al., *Model validation of untethered ultrasonic neural dust motes for cortical recording*, J. Neurosci. Methods, vol. 244, pp. 114-122 (2015)), and is adjusted with a DC power supply. The transmit time and the period of the system are 3 µs and 80 µs, leaving a ~77 µs window for reception. A 2×1 element in the center of the array is used for receiving the backscatter. The output of the receive crystals is amplified and digitized for processing. The measured backscatter sensitivity is ~0.5% per volt applied to the input of the backscatter circuit, which is in agreement with the simulation. The overall performance of the system is summarized in Table 4.

TABLE 4

Summary of System Performance

| | |
|---|---|
| Supply voltage | 1.8 V |
| Output voltage | 32 V |
| Number of channels | 7 |
| Operating frequency | 1.6 MHz |
| Charge pump + level shifter efficiency | 26.3% |
| Acoustic-to-Electrical efficiency | 0.12% |
| Backscatter change | 0.5%/V |
| Energy per transmit phase | 0.75 µJ |

Our measurements with the ultrasonic beamforming system suggest that transmit beamforming alone can provide sufficient signal-to-noise ratio (SNR) to enable multiple sensors interrogation in the neural dust platform. The decrease in the SNR with the miniaturization of the dust mote can be largely mitigated by implementing receive beamform. Furthermore, in order to increase the rate of interrogation, one could explore an alternative means of multiplexing, such as spatial multiplexing where multiple motes are interrogated simultaneously with the same transmit beam. However, it is important to consider the system design tradeoff between processing/communication burden to power consumption. Additionally, sufficient suppression of interferences from nearby dust motes is necessary to achieve the required SNR.

The acoustic-to-electrical efficiency at 0.12% currently dominates the efficiency $$\left(\frac{P_{harvested}}{P_{1.8\,V\,supply}}\right)$$

of the overall system. Despite such low efficiency of the power link, if ~1% of the FDA safety regulation (spatial peak average of 1.9 W/cm$^2$) can be outputted, it is possible harvest up to 0.92V peak-to-peak voltage and 180 µW at the 800 µm ultrasonic transducer 50 mm away in water.

Furthermore, the low efficiency of the power link in this demonstration is attributed to such large transmission distance, as determined by the array aperture and the element size. For peripheral nerve intervention, for example, the desired transmission distance is approximately 5 mm, which includes the thickness of skin, tissue, etc. In order to be at the far field of the array, the aperture should be ~4.4 mm. Further scaling of each element can reduce the overall dimensions of the array aperture and the transmission distance down to the desired 5 mm. Simulation indicates that acoustic-to-electrical efficiency up to 1% can be achieved in water with a 100 µm receive ultrasonic transducer.

Figure 29:
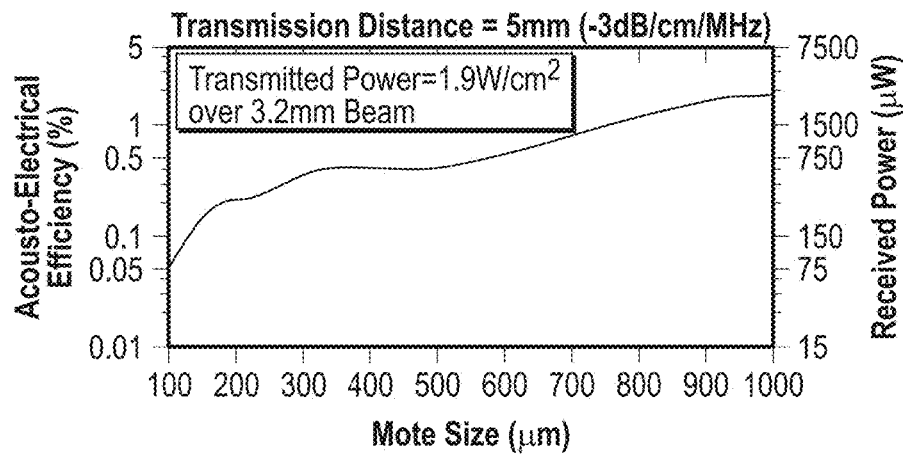
FIG. 29 shows a simulated scaling of miniaturized ultrasonic transducer link efficiency and received power at 5 mm in tissue.

For transmission in tissue, assuming 3 dB/cm/MHz loss in tissue, FIG. 29 shows the scaling of both link efficiency and received power level given operation at 1% of the FDA safety limit. Despite this rather conservative loss, at 100 µm, the simulation indicates that it is possible to harvest up to 0.6V peak-to-peak voltage and 75 µW. Therefore, wireless power transfer in tissue using this platform is feasible. Furthermore, this power level is sufficient to operate highly efficient, low-power energy harvesting circuits and charge pumps, similar to the ASIC presented here, to output voltages that are suitable for electrically stimulating nearby neurons and detecting physiological conditions using sensors.

Example 6—Tracking of Movement and Temperature Drift of Implantable Devices

An implantable device was manufactured with on a 50 µm thick polyimide flexible printed circuit board (PCB) with a ultrasonic transducer piezocrystal (0.75 mm×0.75 mm×0.75 mm) and a custom transistor (0.5 mm×0.45 mm) attached to the topside of the board with a conductive silver paste. Electrical connections between the components are made using aluminum wirebonds and conductive gold traces. Exposed gold recording pads on the bottom of the board (0.2 mm×0.2 mm) are separated by 1.8 mm and make contact on the nerve or muscle to record electrophysiological signals. Recorded signals are sent to the transistor's input through micro-vias. Additionally, some implants were equipped with 0.35 mm-wide, 25 mm-long, flexible, compliant leads with test points for simultaneous measurement of both the voltage across the piezocrystal and direct wired measurement of the extracellular potential across the electrode pair used by the ultrasonic transducer (this direct, wired recording of extracellular potential as the ground truth measurement is referred to below, which is used as a control for the ultrasonically reconstructed data). The entire implant is encapsulated in a medical grade UV-curable epoxy to protect wirebonds and provide insulation. A single implantable device measures roughly 0.8 mm×3 mm×1 mm. The size of the implants is limited only by our use of commercial polyimide backplane technology, which is commercially accessible to anyone; relying on more aggressive assembly techniques with in-house polymer patterning would produce implants not much larger than the piezocrystal dimensions (yielding a ~1 mm$^3$ implant).

Figure 30A:
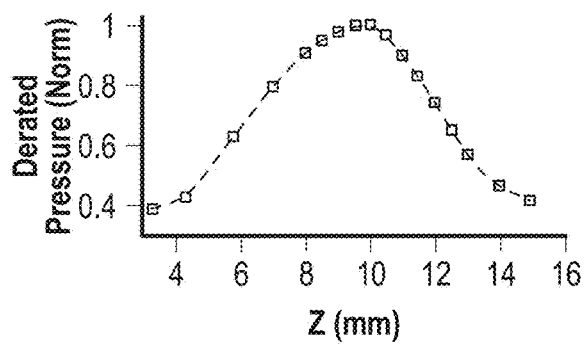
FIG. 30A shows the de-rated normalized peak pressure as a function of distance from the surface of an exemplary transducer has a de-rated focus at about 8.9 mm at 1.85 MHz.
Figure 30B:
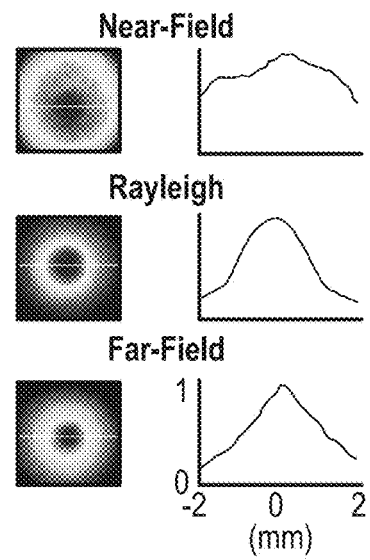
FIG. 30B shows the XY cross-sectional beam patterns and the corresponding 1D voltage plot at y=0 at near-field, Rayleigh distance, and far-field. The patterns show the beam focusing at the Rayleigh distance.
Figure 30C:
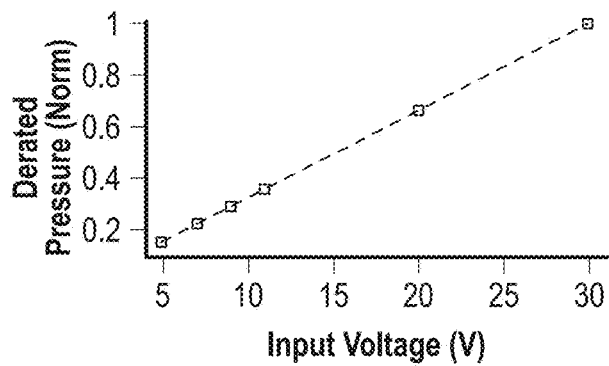
FIG. 30C shows that the transducer's output pressure was a linear function of input voltage (up to 32 V peak-to-peak).

An external, ultrasonic transceiver board interfaces with the implantable device by both supplying power (transmit (TX) mode) and receiving reflected signals (receive (RX) mode). This system is a low-power, programmable, and portable transceiver board that drives a commercially available external ultrasonic transducer (V323-SU, Olympus, Waltham, Mass.). The transceiver board exhibited a de-rated pressure focus at ~8.9 mm (FIG. 30A). The XY cross-sectional beam-pattern clearly demonstrated the transition from the near-field to far-field propagation of the beam, with the narrowest beam at the Rayleigh distance (FIG. 30B). The transducer was driven with a 5 V peak-to-peak voltage signal at 1.85 MHz. The measured de-rated peak rarefaction pressure was 14 kPa, resulting in a mechanical index (MI) of 0.01. De-rated spatial pulse peak average ($I_{SPPA}$) and spatial peak time average ($I_{SPTA}$) of 6.37 mW/cm$^2$ and 0.21 mW/cm$^2$ at 10 kHz pulse repetition were 0.0034% and 0.03% of the FDA regulatory limit, respectively (Food and Drug Administration, 2008). The transceiver board was capable of outputting up to 32 V peak-to-peak and the output pressure increased linearly with the input voltage (FIG. 30C).

Figure 31A:
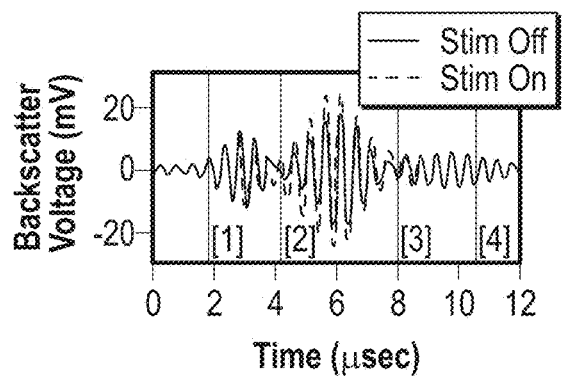
FIG. 31A (duplicate of FIG. 5E shown in different context) shows example backscatter waveform showing different regions of backscatter. The backscatter waveform is found flanked (in time) by regions which correspond to reflections arising from non-responsive regions; these correspond to reflected waveforms from other implantable device components. The measurement from the non-responsive regions (which do not encode biological data) can be used as a reference. As a result of taking this differential measurement, any movements of the entire structure relative to the external transducer during the experiment can be subtracted out.
Figure 31B:
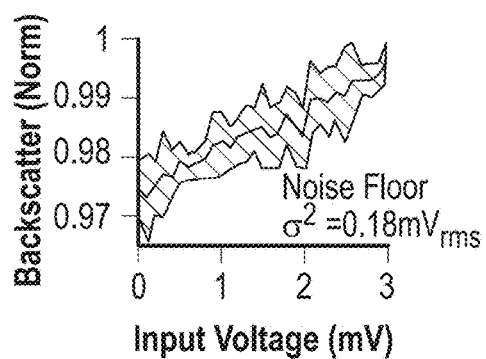
FIG. 31B is a calibration curve obtained from the custom water tank setup, which show the noise for of $0.18$ mV$_{rms}$.
Figure 31C:
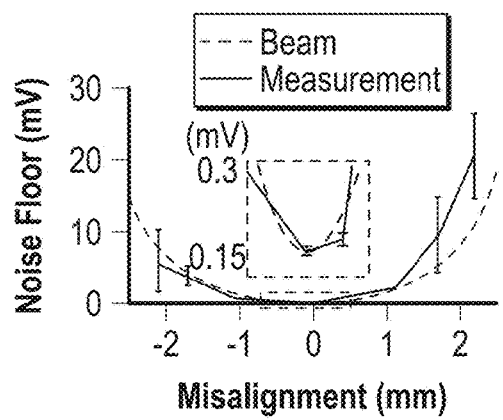
FIG. 31C shows the effect of noise floor as a function of lateral misalignment following the beam pattern power fall-off.
Figure 31D:
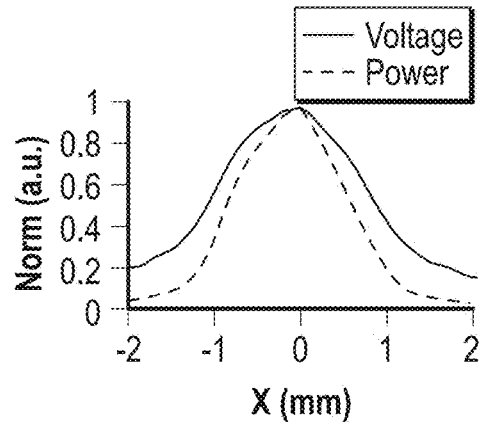
FIG. 31D shows a 1-D plot of the transducer's off-axis voltage and power drop off at y=0 at Rayleigh distance.
Figure 31E:
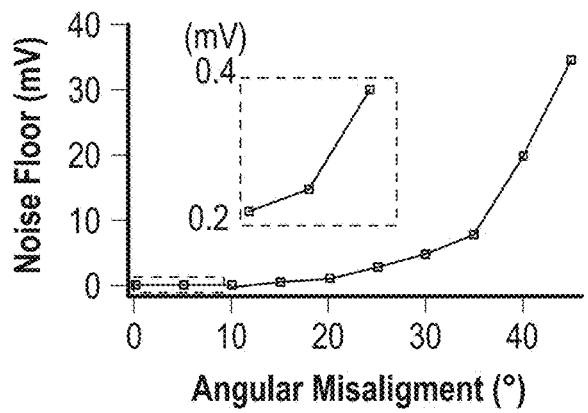
FIG. 31E shows a plot of drop in the effective noise floor as a function of angular misalignment. Angular misalignment results in a skewed beam pattern: ellipsoidal as opposed to circular. This increases the radius of focal spot (spreading energy out over a larger area); the distortion of the focal spot relaxes the constraint on misalignment.

The entire system was submerged and characterized in a custom-built water tank with manual 6 degrees-of-freedom (DOF) linear translational and rotational stages (Thorlabs Inc., Newton, N.J.). Distilled water was used as a propagation medium, which exhibits similar acoustic impedance as tissue, at 1.5 MRayls. For initial calibration of the system, a current source (2400-LV, Keithley, Cleveland, Ohio) was used to mimic extracellular signals by forcing electrical current at varying current densities through 0.127 mm thick platinum wires (773000, A-M Systems, Sequim, Wash.) immersed in the tank. The neural dust mote was submerged in the current path between the electrodes. As current was applied between the wires, a potential difference arose across the implant electrodes. This potential difference was used to mimic extracellular electrophysiological signals during tank testing. To interrogate the neural dust mote, six 540 ns pulses every 100 μs were emitted by the external transducer. These emitted pulses reflect off the neural dust mote and produce backscatter pulses back towards the external transducer. Reflected backscatter pulses were recorded by the same transceiver board. The received backscatter waveform exhibits four regions of interest; these are pulses reflecting from four distinct interfaces (FIG. 31A): 1) the water-polymer encapsulation boundary, 2) the top surface of the piezoelectric crystal, 3) the piezo-PCB boundary, and 4) the back of the PCB. As expected, the backscatter amplitude of the signals reflected from the piezoelectric crystal (second region) changed as a function of changes in potential at the recording electrodes. Reflected pulses from other interfaces did not respond to changes in potential at the recording electrodes. Importantly, pulses from the other non-responsive regions were used as a signal level reference, making the system robust to motion or heat-induced artifacts (since pulses reflected from all interfaces change with physical or thermal disturbances of the neural dust mote but only pulses from the second region change as a function of electrophysiological signals). In a water tank, the system showed a linear response to changes in recording electrode potential and a noise floor of ~0.18 mVrms (FIG. 31B). The overall dynamic range of the system is limited by the input range of the transistor and is greater than >500 mV (i.e., there is only an incremental change in the current once the transistor is fully on (input exceeds its threshold voltage) or fully off). The noise floor increased with the measured power drop-off of the beam; 0.7 mm of misalignment degraded it by a factor of two (N=5 devices, FIG. 31C). This lateral mis-alignment-induced increase in the noise floor constitutes the most significant challenge to neural recordings without a beamsteering system (that is, without the use of an external transducer array that can keep the ultrasonic beam focused on the implanted dust mote and, thus, on-axis). On axis, the implantable device converted incident acoustic power to electrical power across the load resistance of the piezo with ~25% efficiency. FIG. 31D plots the off-axis drop-off of voltage and power at one Rayleigh distance for the transducer used in this example. Likewise, FIG. 31E plots the change in effective noise floor as a function of angular misalignment.

Example 7—Digital Communication Link Between Implantable Device and Interrogator A system including an implantable device and an interrogator having a transducer array is validated with a benchtop setup mimicking an in-vivo environment. Ultrasound coupling gel serves as a tissue phantom due to its acoustic impedance which is similar to that of target biological tissues (approximately 1.5 MRayl). An implantable device with a bulk piezoelectric transducer with direct connections to the two electrodes contacting the transducer is placed in the tissue phantom, and the interrogator transducer array is coupled to the gel. Both elements are attached to precision controlled stages for accurate positioning. The transducer array is placed 14 mm away from the dust mote, which corresponds to a 18.6 μs round-trip time of flight assuming an acoustic velocity of 1,540 m/s in ultrasound coupling gel. The transducer array is excited with six 1.8 MHz, 0-32 V rectangular pulses, and the backscatter signal is digitized with 2000 samples at 17 Msps and 12-bits of resolution. For time-domain backscatter inspection, complete backscatter waveforms are filtered in real time on the device and sent to the client through a wired, serial connection. In normal operation, the complete modulation extraction algorithm is applied to the backscatter data on the device in real-time, compressing the backscatter signal to four bytes. The processed data is transmitted through Bluetooth's SSP protocol to a remote client and streamed through the GUI in real-time.

Figure 32A:
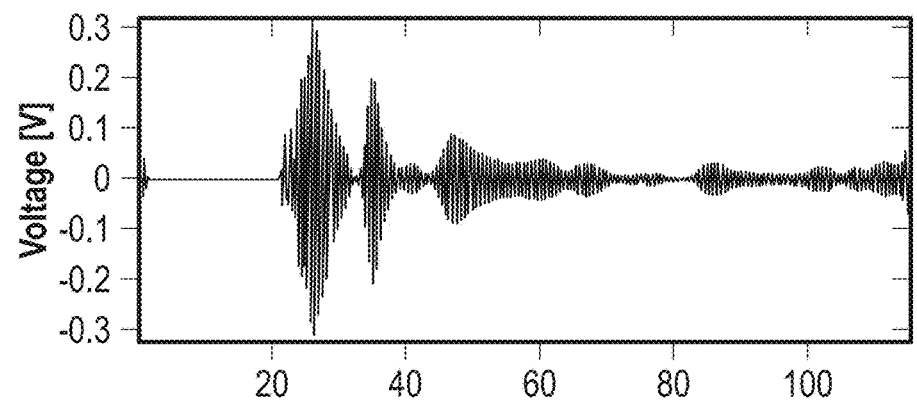
FIG. 32A shows ultrasonic backscatter from an implantable device, with the implantable device implanted inn ultrasound coupling gel used to mimic tissue. The backscatter includes a transmit feedthrough and ring-down centered at 26 microseconds, and the miniaturized ultrasonic transducer backscatter centered around 47 microseconds.
Figure 32B:
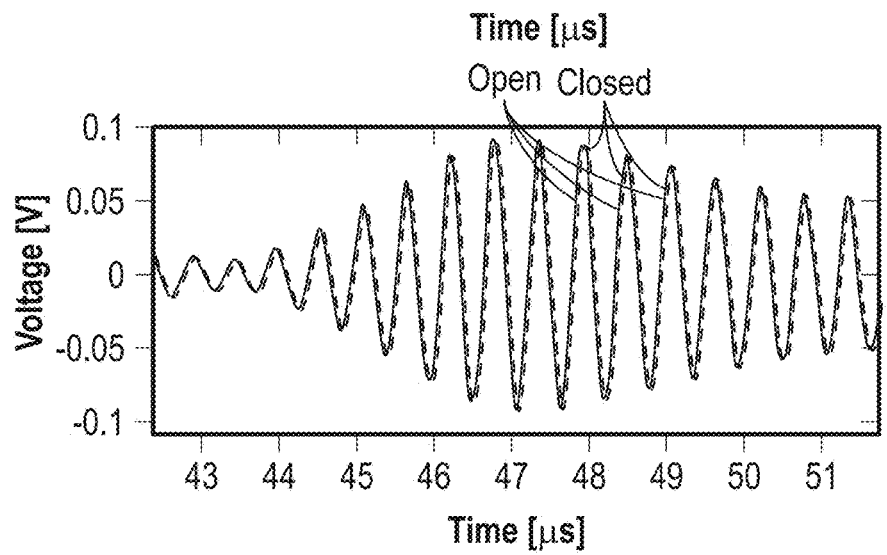
FIG. 32B shows a close-up on the backscatter region from the miniaturized ultrasonic transducer (the responsive region), which shows amplitude modulation as a result of a signal input to the implantable device.

FIG. 32A shows the filtered backscatter signals collected with the described experimental setup. Signals are collected while the dust mote piezocrystal electrodes are in the shorted and opened configurations. The change in impedance due to the switch activity results in a backscatter peak amplitude that is 11.5 mV greater in the open switch configuration, a modulation depth of 6.45%. (FIG. 32B). The long duration of the echo from the mote indicates transducer ringing despite a damping backing layer. While the under-damped transducer system response does spread out the backscatter signal in the time-domain, demodulation is successful as long as the backscatter from the implanted device is captured within the ROI.

Figure 33:
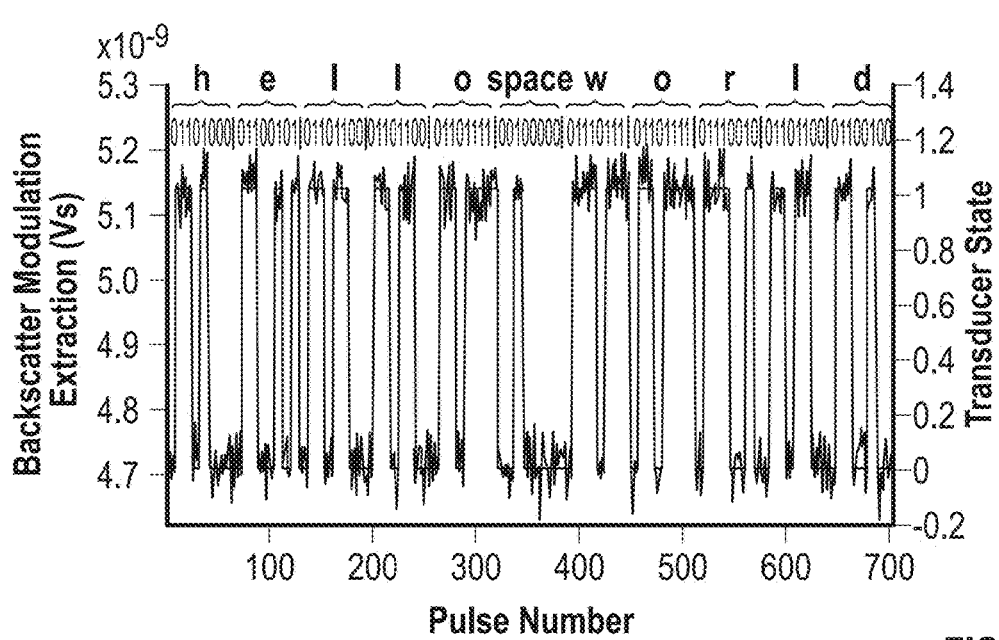
FIG. 33 shows digital data corresponding to ASCII characters 'hello world' wirelessly ready from the implantable device through pulse amplitude backscatter modulation with unipolar encoding.

Using pulse-amplitude-modulated non-return to zero level coding, a backscatter sensor mote is modulated to send a predetermined 11-character ASCII message ("hello world"). The modulation of the device's acoustic impedance is achieved by shunting the piezoelectric transducer across a digitally controlled switch where a high level corresponds to the open configuration and a low level corresponds to the closed configuration. FIG. 33 shows the modulated values on the transducer and the corresponding extracted modulation values of the interrogator. The absolute value and noise margin of the extracted signal values depend on a variety of factors such as mote distance, orientation, and size; however, the extracted waveform remains representative of the modulated signal on the dust mote, varying by a linear scaling factor.

Wirelessly transmitting the extracted backscatter value of the implantable device modulated by "hello world" demonstrates the device's real time communication link with implanted devices. Interrogation of a two state backscatter system provides a robust demonstration of the system's wireless communication link with both an implantable sensor and a remote client. This wireless communication link invites developments toward closed-loop neuromodulation systems to connect the brain with external devices.

Example 8—Temperature Sensor

This example demonstrates an implantable device comprising a bulk piezoelectric transducer with a temperature sensor, namely a thermistor. The system uses an interrogator to power the implantable device using ultrasonic waves, and records ultrasonic backscatter from the implantable device modulated according to the temperature detected by the sensor. This example demonstrates two sizes of sensors based on available components with volumes of 1.45 mm$^3$ and 0.118 mm$^3$. The bulk piezoelectric transducer can be as small as 700 µm in the largest dimension. The individual sensors are able to resolve ±0.5° C. changes in temperature, suitable for medical diagnostic and monitoring purposes. There is less than 0.3° C. drift in temperature readings over 14 days in physiological conditions. This approach is also compatible with more sophisticated temperature sensors such as classic proportional to absolute temperature (PTAT) integrated circuits, as well as digital backscatter approaches.

Each implantable device comprises a surface mount thermistor whose electrodes are electrically connected to the two terminals of a lead zirconate titanate (PZT) piezoelectric cube with 750 µm edges that are perpendicular to the axis of polarization. The thermistor is a negative temperature coefficient (NTC) thermistor in order to vary the current flowing through the two terminals of the piezoelectric crystal as a function of ambient temperature. Electrical contact and adhesion between the electrode pairs of the thermistor and the piezoelectric crystal are established through the application of two distinct, continuous layers of EPO-TEK H20E electrically conductive silver epoxy. PFA-insulated silver wire from A-M Systems with an uncoated diameter of 3 mils (5.5 mil coated diameter) was attached to each electrode of the thermistor using silver epoxy in order to measure the voltage harvested by the piezoelectric cube during water tank characterization. The entire implantable device, excluding the leads, was then coated with a thin layer of EPO-TEK OG116-31 UV curable epoxy in order to prevent water permeation that could lead to shorts.

In order to assess the backscatter modulation that occurs in the received backscatter signal from the implantable device as a function of temperature, a miniature water tank was made out of polylactic acid using an additive manufacturing process. The tank was constructed such that there is a stage to hold a sensor mote adjacent to a thermocouple that is used as an input to an Omega Systems CSI32K benchtop PID controller for temperature monitoring and feedback purposes. An NPT-threaded screw hole was manufactured into the wall of the tank for the insertion of a heating element into the tank. A second piece of the tank was designed to fit on top of the first component in order to seal the tank shut and maintain the transducer at one focal distance away from the mote. The base and top of the tank were sealed together using silicone, and the top of the tank was sealed with a square of 0.5 mil thick PET film in order to thermally isolate the transducer from the tank in an acoustically transparent manner, thereby circumventing artifact superimposition issues that were observed when the transducer was immersed into the tank at higher water temperatures.

Figure 34A:
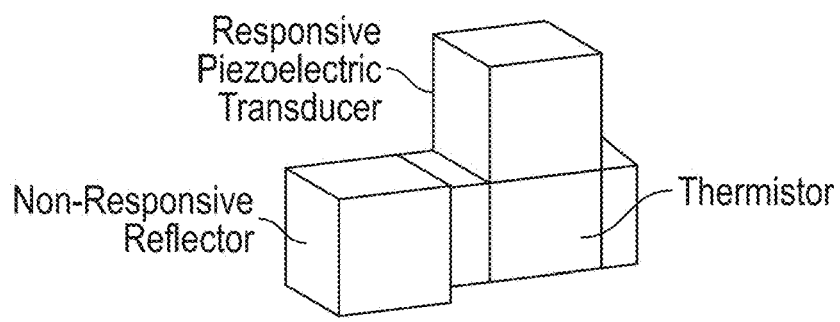
FIG. 34A shows an illustration of an implantable device with a miniaturized ultrasonic bulk piezoelectric transducer and a thermistor. A non-responsive reflector is attached to the implantable device to reflect non-responsive backscatter waves.

The simplest method to eliminate changes in signal arising from motion artifact in analog backscatter systems like this one is to provide two interfaces in the implant that produce backscatter: one interface at the responsive piezoelectric transducer and a second interface at some invariant material junction. Changes in position or orientation that affect the entire implant will cause known changes in backscatter from both interfaces (i.e., the responsive backscatter and the non-responsive backscatter), whereas changes in the measured quantity will produce changes only in the backscatter signal from the responsive interface (i.e., the responsive backscatter). The non-responsive region (that is, the region that does not vary relative to temperature) of the received backscatter is determined based on calibration experiments (and time-of-flight calculations), and changes in the area under the curve of this region are compared to the responsive backscatter modulation in the sensor output waveform. In addition, clustering algorithms can be used to automatically detect a misalignment and to map the changes in backscatter change to a corresponding change in the measurand (in preparation). In order to create a non-responsive region of backscatter in the sensor output, a non-responsive reflector, namely a cube of silicon, was affixed to the implantable device using UV-curable epoxy. The newly-added cube was electrically isolated from the thermistor in order to create a fixed region of backscatter in the sensor output waveform. The implantable device is shown in FIG. 34A, with relative sizes of the two implantable devices (with volumes of 1.45 mm$^3$ and 0.118 mm$^3$) shown in FIG. 34B.

Figure 35:
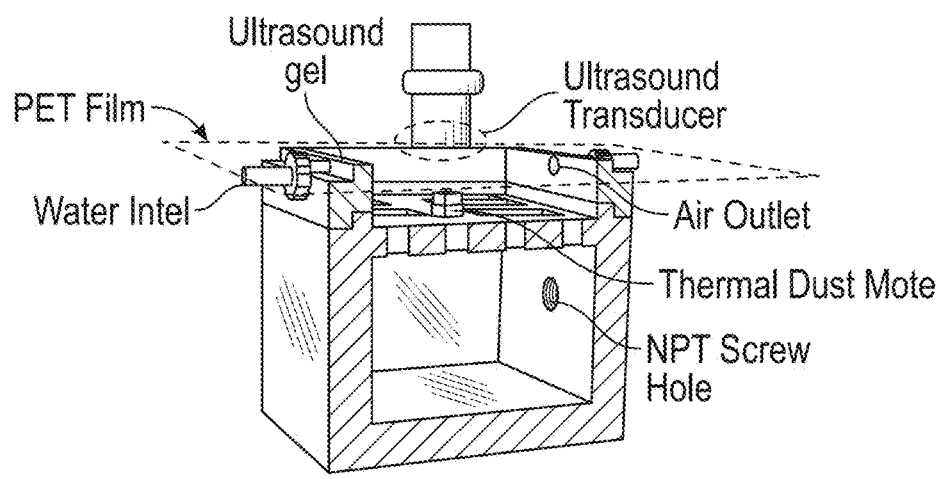
FIG. 35 shows a cross-sectional rendering of an experimental design for backscatter characterization of individual implantable devices with temperature sensors. A sheet of 0.5 mil thick PET was glued onto the top piece of the water tank, which serves to contain the water within the tank while thermally isolating the implantable device.

The experimental setup for backscatter characterization of individual implantable devices is shown in FIG. 35. In order to ensure standardization in the backscatter collection protocol and to maximize the magnitude of the expected response, the implantable devices were aligned to the ultrasonic beam produced by the commercially available single element transducer (V323-SU, Olympus) as assessed by the maximization of the peak voltage being harvested by the piezoelectric crystal on the implantable device. The implantable devices were interrogated at a frequency of 1.8 MHz, and the backscatter was sampled at 1 kHz, although lower sampling rates are possible. The transducer's focal length is 0.9 cm; the distance between the transducer and the motes was set so that the motes were at the focus point. The temperature within the tank was tightly regulated using the benchtop PID controller and varied from 34.5° C. to 45.5° C. in increments of 0.5° C. At each temperature value, ten backscatter waveforms were recorded using an Agilent Tech InfiniiVision DSO-X3024A digital storage oscilloscope. It was observed that the time of flight of the ultrasonic backscatter increases as a function of temperature due to the change of acoustic velocity in water. Thus, the waveform features of interest were temporally aligned to a reference waveform for each backscatter dataset. The reference waveform was selected to be the backscatter waveform at 44.5°

C. for each run. The index of maximum change in backscatter voltage with respect to the reference waveform was found for each trial waveform, the signal was then rectified, filtered and integrated over specified time indices of interest where the maximum change in backscatter amplitude occurs. The same integration bounds were utilized for every temperature that was tested for an individual mote, and the obtained integrals were then normalized with respect to the integral obtained from the reference measurement.

In order to verify that the effects observed in backscatter modulation are not due to changes in external transducer properties as a function of temperature, backscatter tests were conducted in an empty water tank over the temperatures of interest. No significant temperature effects on the received backscatter waveforms were found under these test conditions. Also assessed was the long term drift of the thermistors. Five Panasonic ERT-J1VR682J thermistors were mounted on individual prototyping printed circuit boards (Chip Quik Inc., DC0603T), soldered to leads and covered with UV-curable epoxy. Thermistors were then placed in a beaker containing deionized water; a closed loop temperature control system consisting of a 55 W compact immersion heater (McMaster-Carr, 4668T51), an Omega Systems CSI32K benchtop PID controller and a thermocouple were used to keep the water temperature at 45.5° C. Resistance values were measured from each thermistor at approximately 24-hour intervals over 14 days and percent change in the average value was calculated for each thermistor.

Figure 34B:
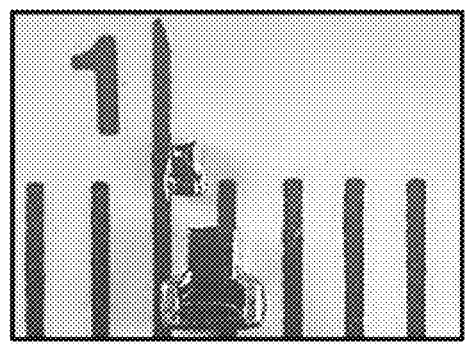
FIG. 34B shows two implantable devices, each with a miniaturized ultrasonic bulk piezoelectric transducer and a thermistor. The top device has an approximate volume of $0.118$ mm$^3$, and the bottom device has an approximate volume of $1.45$ mm$^3$.

The implantable devices include a 0201 SMD packaged thermistor (Panasonic ERT-JZET202J) and a PZT piezocrystal having an edge length of 400 μm (FIG. 34B, top), or a 0603 thermistor and a PZT piezocrystal having an edge length of 750 μm (FIG. 34B, bottom).

Figure 36:
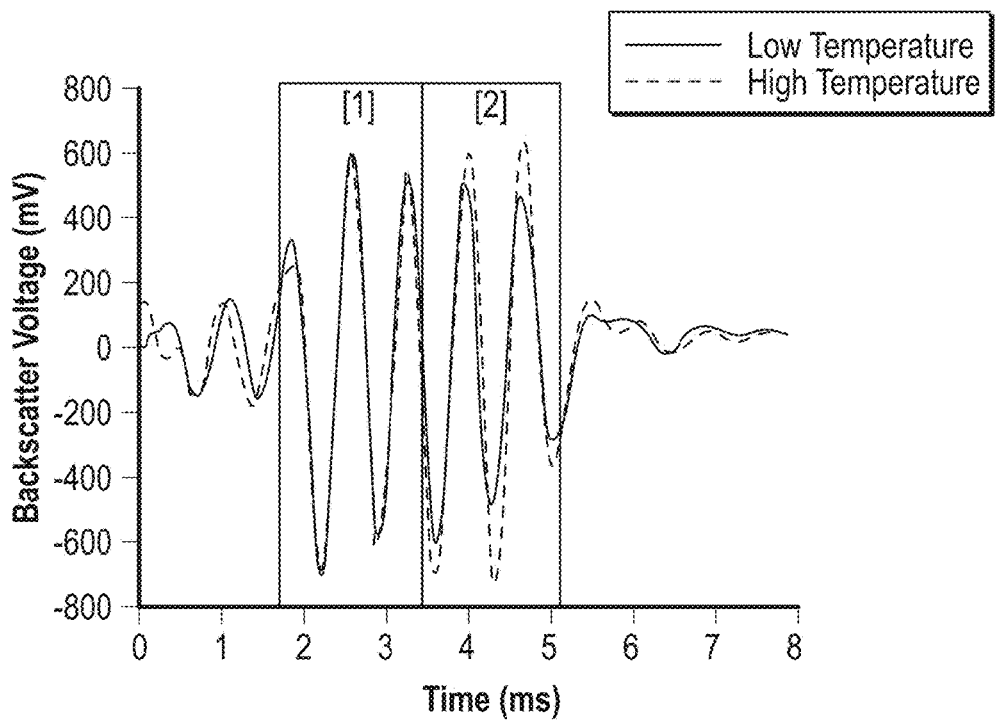
FIG. 36 shows ultrasonic backscatter from an implantable device with a miniaturized ultrasonic bulk piezoelectric transducer, a thermistor, and a non-responsive reflector at high temperature and low temperature. The implantable device was interrogated at 3.35 MHz. Region [1] corresponds to the contribution of the non-responsive reflector, whereas region [2] corresponds to the contribution of the thermally modulated transducer on the implantable device. The temperature dependent changes can be seen as an increase in signal amplitude (and thus area under the curve for rectified signals) in region [2]. Region does not exhibit such changes.

FIG. 36 shows a typical backscatter profile from an implantable device comprising both a non-responsive reflector and a bulk piezoelectric transducer connected to a thermistor. Region 1 arises from the non-responsive reflector and region 2 arises from the responsive piezoelectric transducer. Both regions vary with displacement and rotation while only the responsive region varies with temperature changes, as shown.

Figure 37:
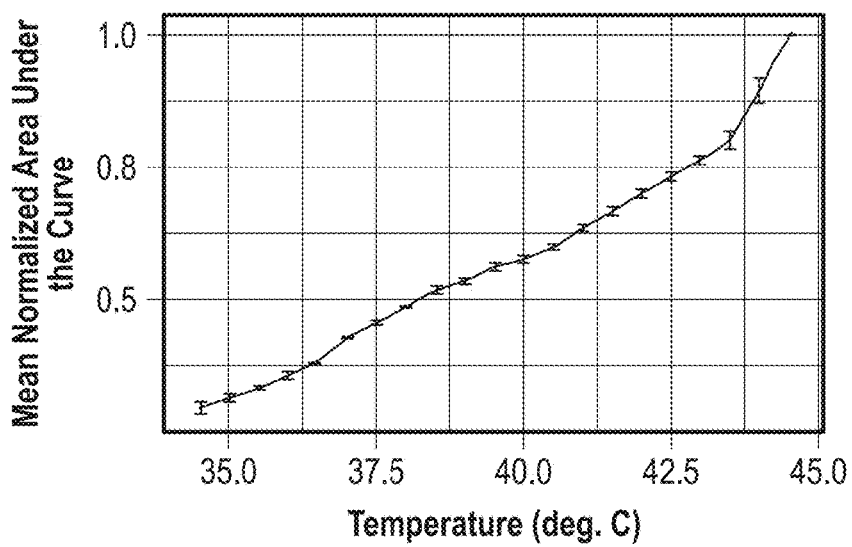
FIG. 37 shows mean normalized area under the curve for the ultrasonic backscatter of a single implantable device with a thermistor as a function of temperature from 34.5° C. to 44.5° C. Temperature was increased at 0.5° C. intervals, and ten collected backscatter waveforms areas were normalized to those at 44.5° C. Error bars represent standard deviation of the ten measurements at each temperature.

A single implantable device with an temperature sensor is capable of producing a monotonically varying temperature-dependent change in backscatter for physiologically-relevant temperatures with a 0.5° C. precision, as shown in FIG. 37. Over 14 days, the maximum deviation in the mean recordings for a thermistor was found to be 34Ω. The Steinhart-Hart equation models the relationship between temperature and resistance for an NTC thermistor:

$$R = R_0 \exp[-\beta(1/T_0 - 1/T)]$$

where R is the measured resistance value at temperature T. For the used 0603 thermistors, the decay parameter β is 4250 $K^{-1}$, and $R_0$ was reported to be 6.8 kΩ for an initial temperature $T_0$=298 K. The temperature change that corresponds to a change in resistance can be found by applying the Steinhart-Hart equation twice and rearranging:

$$T_2 = \beta T_0 / [T_0 \ln(\Delta R/R_0 + \exp[-\beta(1/T_0 - 1/T_1)]) + \beta]$$

where ΔR is the change in resistance values $R_2-R_1$ at temperatures $T_2$ and $T_1$ respectively. It was found that the change in resistance of 34Ω corresponds to a temperature change of 0.296 K. This temperature change is within the measurement error for the PID controller.

This example demonstrates that the implantable device with a thermal sensor in an ultrasonically addressable system with a miniaturized ultrasonic transducer as small as 700 μm in their largest dimension using commercially available components. This method does not depend on empirical heat exchange models for the determination of temperature measurements, and as such could become a useful tool in deep tissue temperature measurements. For completeness, it was verified that thermistors, which are a skin temperature acquisition standard in clinical medicine, do not exhibit significant drift when exposed to physiological temperatures over extended periods of time. Individual implantable devices were able to resolve changes in temperature with good precision at 1 cm from the transducer, which is significant for medical diagnostic and monitoring purposes. Lastly, it was demonstrated that the implantable devices can be assembled using smaller readily available components to create a fully sub-millimeter sensor. Given the ability to penetrate centimeters deep into tissue, this approach provides a straightforward way to sense deep-tissue temperature.

What is claimed is:

1. A system, comprising:
   (a) an implantable device, comprising:
      a sensor configured to detect a pH; and
      an ultrasonic transducer with a length of 5 mm or less in the longest dimension, the ultrasonic transducer configured to receive ultrasonic waves that power the implantable device, receive a current modulated based on the pH detected by the sensor, and emit a pH-dependent ultrasonic backscatter based on the current received by the ultrasonic transducer; and
   (b) an interrogator comprising one or more ultrasonic transducers configured to transmit the ultrasonic waves that power the implantable device, and receive the ultrasonic backscatter from the implantable device.

2. The system of claim 1, wherein the sensor is an optical sensor.

3. The system of claim 2, wherein the optical sensor comprises a light source and an optical detector.

4. The system of claim 2, wherein the optical sensor comprises a matrix comprising a fluorophore, and wherein fluorescence intensity or fluorescence lifetime of the fluorophore depends on the pH.

5. The system of claim 2, wherein the optical sensor comprises a matrix comprising a fluorophore and an oscillating or pulsating light source, where a phase shift or time delay between light emitted from the light source and fluorescence detected by a fluoresce sensor is based on the pH.

6. The system of claim 1, wherein the sensor is a potentiometric chemical sensor or an amperometric chemical sensor.

7. The system of claim 1, wherein the ultrasonic transducer is a bulk piezoelectric transducer, a piezoelectric micro-machined ultrasonic transducer (PMUT) or a capacitive micro-machined ultrasonic transducer (CMUT).

8. The system of claim 1, wherein the implantable device is 5 mm or less in the longest dimension.

9. The system of claim 1, wherein the volume of the implantable device is 5 $mm^3$ or less.

10. The system of claim 1, wherein the implantable device is implanted in a subject.

11. The system of claim 10, wherein the subject is an animal or a plant.

12. The system of claim 1, wherein the implantable device further comprises an integrated circuit.

13. The system of claim 12, wherein the integrated circuit comprises a power circuit.

14. The system of claim 12, wherein the integrated circuit comprises a driver configured to provide current to the sensor.

15. The system of claim 12, wherein the integrated circuit comprises a front end configured to receive a signal from the sensor.

16. The system of claim 12, wherein the integrated circuit comprises a digital circuit.

17. The system of claim 16, wherein the digital circuit is configured to operate a modulation circuit.

18. The system of claim 17, wherein the digital circuit is configured to transmit a digitized signal to the modulation circuit, and wherein the digitized signal is based on the detected pH.

19. The system of claim 1, wherein the implanted device is at least partially encapsulated by a biocompatible material.

20. The system of claim 1, wherein the implantable device comprises two or more sensors.

21. The system of claim 1, wherein the interrogator is configured to be wearable by a subject.

22. A method of detecting a pH, comprising:
powering one or more implantable devices implanted in a subject using ultrasonic waves emitted from an interrogator comprising one or more transducers, wherein the one or more implantable devices comprise an ultrasonic transducer with a length of 5 mm or less in the longest dimension and a sensor configured to measure the pH;
converting energy from the ultrasonic waves into an electrical current;
transmitting the electrical current to the sensor;
measuring the amount of the pH using the sensor;
modulating the electrical current based on the measured pH;
transducing the modulated electrical current into an ultrasonic backscatter that encodes the measured pH;
emitting the ultrasonic backscatter to the interrogator; and
receiving the ultrasonic backscatter.

23. The method of claim 22, wherein the one or more implantable devices are implanted in a subject.

24. The method of claim 22, wherein the interrogator is worn by the subject.

25. The method of claim 22, wherein the sensor is an optical sensor that comprises a matrix comprising a fluorophore and an oscillating or pulsating light source, and the method further comprises:
determining a phase shift or time delay between light emitted from the light source and fluorescence emitted by the fluorophore, wherein the phase shift or time delay is based on the pH.

26. A method of detecting a pH, comprising:
powering one or more implantable devices implanted in a subject using ultrasonic waves emitted from an interrogator comprising one or more transducers, wherein the one or more implantable devices each comprise an ultrasonic transducer with a length of 5 mm or less in the longest dimension and a sensor configured to measure the pH;
converting energy from the ultrasonic waves into an electrical current;
measuring the pH using the sensor;
modulating the electrical current based on the measured pH;
transducing the modulated electrical current into an ultrasonic backscatter that encodes the measured pH; and
emitting the ultrasonic backscatter to the interrogator; and
receiving the ultrasonic backscatter.

27. The method of claim 26, wherein the one or more implantable devices are implanted in a subject.

28. The method of claim 26, wherein the interrogator is worn by the subject.

29. The method of claim 26, comprising analyzing the ultrasonic backscatter to determine the measured pH.

30. The method of claim 26, wherein the sensor is an optical sensor that comprises a matrix comprising a fluorophore and an oscillating or pulsating light source, and the method further comprises:
determining a phase shift or time delay between light emitted from the light source and fluorescence emitted by the fluorophore, wherein the phase shift or time delay is based on the pH.

* * * * *

UNITED STATES PATENT AND TRADEMARK OFFICE
CERTIFICATE OF CORRECTION

PATENT NO. : 10,300,310 B2
APPLICATION NO. : 16/141930
DATED : May 28, 2019
INVENTOR(S) : Michel M. Maharbiz et al.

Page 1 of 1

It is certified that error appears in the above-identified patent and that said Letters Patent is hereby corrected as shown below:

In the Specification

Column 1, Lines 18-21, change "This invention was made with government support under Grant Nos. HR0011-15-2-0006 awarded by the Defense Advanced Research Projects Agency (DARPA). The government has certain rights in the invention." to --This invention was made with government support under HR0011-15-2-0006 awarded by the Defense Advanced Research Projects Agency. The government has certain rights in the invention.--.

Signed and Sealed this
Eighth Day of October, 2019

Andrei Iancu
*Director of the United States Patent and Trademark Office*